(12) United States Patent
Tazi et al.

(10) Patent No.: US 9,827,237 B2
(45) Date of Patent: Nov. 28, 2017

(54) COMPOUNDS USEFUL FOR TREATING DISEASES CAUSED BY RETROVIRUSES

(71) Applicants: ABIVAX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

(72) Inventors: Jamal Tazi, Clapiers (FR); Florence Mahuteau-Betzer, Saint Remy-les-Chevreuse (FR); Romain Najman, l'Hay les Roses (FR); Didier Scherrer, Castelnau le Lez (FR); Noëlie Campos, Le Cres (FR); Aude Garcel, Le Cres (FR)

(73) Assignees: ABIVAX, Paris (FR); CENTRE NATIONAL DE LA RECHERCHE SCIENTIFIQUE, Paris (FR); UNIVERSITE DE MONTPELLIER, Montpellier (FR); INSTITUT CURIE, Paris (FR)

( * ) Notice: Subject to any disclaimer, the term of this patent is extended or adjusted under 35 U.S.C. 154(b) by 0 days.

(21) Appl. No.: 14/902,935

(22) PCT Filed: Jul. 4, 2014

(86) PCT No.: PCT/IB2014/062849
§ 371 (c)(1),
(2) Date: Jan. 5, 2016

(87) PCT Pub. No.: WO2015/001518
PCT Pub. Date: Jan. 8, 2015

(65) Prior Publication Data
US 2016/0151348 A1    Jun. 2, 2016

Related U.S. Application Data

(60) Provisional application No. 61/843,155, filed on Jul. 5, 2013.

(51) Int. Cl.
| *A61K 31/4709* | (2006.01) |
| *A61K 31/47*   | (2006.01) |
| *A61K 31/497*  | (2006.01) |
| *A61K 31/506*  | (2006.01) |
| *A61K 31/498*  | (2006.01) |

(52) U.S. Cl.
CPC .......... *A61K 31/4709* (2013.01); *A61K 31/47* (2013.01); *A61K 31/497* (2013.01); *A61K 31/498* (2013.01); *A61K 31/506* (2013.01)

(58) Field of Classification Search
CPC .. A61K 31/47; A61K 31/4709; A61K 31/497; A61K 31/498; A61K 31/506
See application file for complete search history.

(56) References Cited

U.S. PATENT DOCUMENTS

| 2,605,182 A | 7/1952 | Peterson |
| 7,019,147 B1 | 3/2006 | Barth et al. |
| 9,061,999 B2 | 6/2015 | Tazi et al. |
| 9,108,919 B2 | 8/2015 | Roux et al. |
| 9,145,367 B2 | 9/2015 | Tazi et al. |
| 2003/0207886 A1 | 11/2003 | Plucker et al. |
| 2004/0038969 A1 | 2/2004 | Doherty et al. |
| 2005/0119225 A1 | 6/2005 | Schumacher et al. |
| 2006/0089380 A1 | 4/2006 | Barnham et al. |
| 2008/0161353 A1 | 7/2008 | Barnham et al. |
| 2011/0003843 A1 | 1/2011 | Lejeune et al. |

FOREIGN PATENT DOCUMENTS

| DE | 958 647 C   | 2/1957 |
| EP | 0 394 112 A2 | 10/1990 |

(Continued)

OTHER PUBLICATIONS

Hernandez-Lopez et. al., Biochemical Journal, 2012, Biochemical Society, vol. 445, pp. 145-156.*

(Continued)

*Primary Examiner* — Sarah Pihonak
(74) *Attorney, Agent, or Firm* — Oliff PLC

(57) ABSTRACT

Methods for preventing or treating retroviral infection not HIV and/or for preventing, inhibiting or treating a disease caused by the retroviral infection include contacting a cell with compound (I)

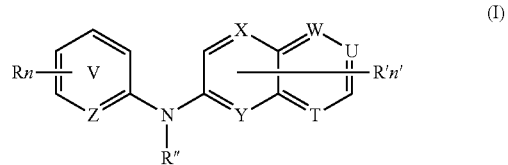

wherein:

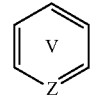

means a pyridazine, pyrimidine or pyrazine group, R independently represent a hydrogen atom, halogen atom or group chosen among a —CN, hydroxyl, —COOR$_1$, (C$_1$-C$_3$) fluoroalkyl, (C$_1$-C$_3$)fluoroalkoxy, —NO$_2$, —NR$_1$R$_2$, (C$_1$-C$_4$)alkoxy, phenoxy and (C$_1$-C$_3$)alkyl group, the alkyl being optionally mono-substituted by hydroxyl group, n is 1, 2 or 3, n' is 1 or 2, R' is a hydrogen atom, halogen atom or group chosen among (C$_1$-C$_3$)alkyl group, hydroxyl group, —COOR$_1$ group, —NO$_2$ group, —NR$_1$R$_2$ group, morpholinyl or morpholino group, N-methylpiperazinyl group, (C$_1$-C$_3$)fluoroalkyl group, (C$_1$-C$_4$)alkoxy group and —CN group, Z is N or C, Y is N or C, X is N or C, W is N or C, T is N or C, U is N or C.

12 Claims, No Drawings

(56) References Cited

FOREIGN PATENT DOCUMENTS

| | | | |
|---|---|---|---|
| EP | 2 266 972 A1 | 12/2010 | |
| EP | 2 465 502 A1 | 6/2012 | |
| EP | 2 757 161 A1 | 7/2014 | |
| FR | 2 387 229 A1 | 11/1978 | |
| FR | 2 436 786 A1 | 4/1980 | |
| FR | 2 627 493 A1 | 8/1989 | |
| FR | 2 645 861 A1 | 10/1990 | |
| FR | 2 849 474 A3 | 7/2004 | |
| FR | 2 859 474 A1 | 3/2005 | |
| FR | 2 859 475 A1 | 3/2005 | |
| FR | WO 2010143169 A2 * | 12/2010 | ........... C07D 213/74 |
| GB | 585362 A | 2/1947 | |
| JP | H09-508642 A | 9/1997 | |
| JP | 2005-507365 A | 3/2005 | |
| WO | 95-21613 A1 | 8/1995 | |
| WO | 00/59875 A2 | 10/2000 | |
| WO | 02/074726 A2 | 9/2002 | |
| WO | 2004/007461 A1 | 1/2004 | |
| WO | 2004/078731 A1 | 9/2004 | |
| WO | 2005/023255 A2 | 3/2005 | |
| WO | 2005/051302 A2 | 6/2005 | |
| WO | 2006/081444 A2 | 8/2006 | |
| WO | 2008/003864 A1 | 1/2008 | |
| WO | 2008/008234 A1 | 1/2008 | |
| WO | 2008/089459 A1 | 7/2008 | |
| WO | 2008/101935 A2 | 8/2008 | |
| WO | 2008/115870 A2 | 9/2008 | |
| WO | 2008/143440 A1 | 11/2008 | |
| WO | 2009/023844 A2 | 2/2009 | |
| WO | 2009/029617 A1 | 3/2009 | |
| WO | 2009/087238 A2 | 7/2009 | |
| WO | 2010/143168 A2 | 12/2010 | |
| WO | 2010/143169 A2 | 12/2010 | |
| WO | 2010/143170 A2 | 12/2010 | |
| WO | 2010/151755 A2 | 12/2010 | |
| WO | 2012/080953 A1 | 6/2012 | |
| WO | 2014/055944 A1 | 4/2014 | |

OTHER PUBLICATIONS

Edwards et. al., Viruses, 2011, MDPI, vol. 3, pp. 861-885.*
Bisset et. al., Antiviral Research, 2002, Elsevier, vol. 53, pp. 35-45.*
Powell et. al., European Journal of Biochemistry, 1996, FEBS, vol. 241, pp. 664-674.*
U.S. Appl. No. 13/377,760, filed Jul. 2, 2012 in the name of Tazi et al.
Nov. 10, 2014 International Search Report issued in International Application No. PCT/IB2014/062849.
Nov. 10, 2014 Written Opinion issued in International Application No. PCT/IB2014/062849.
Jun. 10, 2015 Notice of Allowance issued in U.S. Appl. No. 13/377,760.
Jul. 18, 2014 Office Action issued in U.S. Appl. No. 13/377,760.
Nov. 21, 2013 Office Action issued in U.S. Appl. No. 13/377,760.
Jun. 27, 2014 Office Action issued in U.S. Appl. No. 13/993,990.
Manley et al. "SR Proteins and Splicing Control". Genes & Development, vol. 10, pp. 1569-1579,1996.
Graveley. "Sorting Out the Complexity of SR Protein Functions". RNA, vol. 6, pp. 1197-1211, 2000,.
Wang et al. "SC35 Plays a Role in T Cell Development and Alternative Splicing of CD45". Molecular Cell, vol. 7, pp. 331-342, 2001.
Ewing et al. "Analysis of Expressed Sequence Tags Indicates 35,000 Human Genes". Nature Genetics, vol. 25, pp. 232-234, 2000.
Cartegni et al. "Listening to Silence and Understanding Nonsense: Exonic Mutations That Affect Splicing". Nature views—Genetics, vol. 3, pp. 285-298, 2002.
Tazi et al. "The Spliceosome: A Novel Multi-Faceted Target for Therapy". Trends in Biochemical Sciences, vol. 30, No. 8, pp. 469-478, 2005.
Nissim-Rafinia et al. "Cellular and Viral Splicing Factors Can Modify the Splicing Pattern of CFTR Transcripts Carrying Splicing Mutations". Human Molecular Genetics, vol. 9, No. 12, pp. 1771-1778, 2000.
Hofmann et al. "HTRA2-.B1 Stimulates an Exonic Splicing Enhancer and Can Restore Full-Length SMN Expression to Survival Motor Neuron 2 (SMN2)". PNAS, vol. 97, No. 17, pp. 9618-9623, 2000.
Sazani et al. "Systemically Delivered Antisense Oligomers Upregulate Gene Expression in Mouse Tissues". Nature Biotechnology, vol. 20, pp. 1228-1233, 2002.
Sazani et al. "Modulation of Alternative Splicing by Antisense Oligonucleotides". Prog. Mol. Subcell. Biol., vol. 31, pp. 217-239, 2003.
Cartegini et al. "Correction of Disease-Associated Exon Skipping by Synthetic Exon-Specific Activators". Nature Structural Biology, vol. 10, No. 2, pp. 120-125, 2003.
Andreassi et al. "Aclarubicin Treatment Restores SMN Levels to Cells Derived From Type 1 Spinal Muscular Atrophy Patients". Human Molecular Genetics, vol. 10, No. 24, pp. 2841-2849, 2001.
Liu et al. "Partial Correction of Endogenous F508 CFTR in Human Cystic Fibrosis Airway Epithelia by Spliceosome-Mediated RNA Trans-Splicing". Nature Biotechnology, vol. 20, pp. 47-52, 2002.
Bakkour et al. "Small-Molecule Inhibition of HIV Pre-MRNA Splicing as a Novel Antiretroviral Theraphy to Overcome Drug Resistance". PLOS Pathogens, vol. 3, No. 10, pp. 1530-1539, 2007.
Connor et al. "VPR Is Required for Efficient Replication of Human Immunodeficiency Virus Type-1 in Mononuclear Phagocytes". Virology, vol. 206, pp. 935-944, 1995.
U.S. Appl. No. 13/377,745, filed Dec. 12, 2011 in the name of Roux et al.
U.S. Appl. No. 13/377,753, filed Dec. 12, 2011 in the name of Tazi et al.
Dec. 23, 2013 Office Action issued in U.S. Appl. No. 13/377,753.
Wang et al. "Alternative Isoform Regulation in Human Tissue Transcriptomes". Nature, vol. 456, pp. 470-476, 2008.
Pan et al. "Deep Surveying of Alternative Splicing Complexity in the Human Transcriptome by High-Throughput Sequencing". Nature Genetics, vol. 40, No. 12, pp. 1413-1415, 2008.
F. J. Leinweber. "Possible Physiological Roles of Carboxylic Ester Hydrolases". Drug Metabolism Reviews, vol. 18, No. 4, pp. 379-439, 1987.
Mar. 9, 2012 International Search Report issued in International Patent Application No. PCT/IB2011/055643.
Jun. 18, 2013 International Preliminary Report on Patentability issued in International Patent Application No. PCT/IB2011/055643.
U.S. Appl. No. 13/377,753, filed Jul. 4, 2012 in the name of Tazi et al.
U.S. Appl. No. 13/377,745, filed Jul. 5, 2012 in the name of Roux et al.
U.S. Appl. No. 13/993,990, filed Jul. 13, 2012 in the name of Tazi et al.
Johnson et al. "Genome-Wide Survey of Human Alternative Pre-MRNA Splicing With Exon Junction Microarrays". Science, vol. 302, pp. 2141-2144, 2003.
Aug. 15, 2014 Office Action issued in U.S. Appl. No. 13/377,753.
El-Sayed et al. "Synthesis of Some Novel Quinoline-3-Carboxylic Acids and Pyrimidoquinoline Derivatives As Potential Antimicrobial Agents". Archiv der Pharmize, vol. 335, No. 9, pp. 403-410, 2002.
Silberg et al. "N-Acyl-N, N-Dipyridyl and N-Acyl-N-Pyridyl-N-Quinoyl Amine Based Palladium Complexes. Synthesis, X-Ray Structures, Heterogenization and Use in Heck Couplings". Journal of Organmetallic Chemistry, vol. 622, pp. 6-18, 2001.
File Registry on STN, 195876-33-6/RN, entered on Oct. 23, 1997.
File Registry on STN, 70125-24-5/RN, entered on Nov. 16, 1984.
Dec. 5, 2014 Office Action issued in U.S. Appl. No. 14/087,762.
CAS Registry No. 215589-34-7 added on STN on Dec. 15, 1998.
CAS Registry No. 208661-32-9 added on STN on Jul. 19, 1998.
CAS Registry No. 204851-25-2 added on STN on Apr. 30, 1998.
CAS Registry No. 138386-77-3 added on STN on Jan. 17, 1992.
CAS Registry No. 70682-97-2 added on STN on Nov. 16, 1984.
CAS Registry No. 10562-04-6 added on STN on Nov. 16, 1984.

CAS Registry No. 5468-85-9 added on STN on Nov. 16, 1984.
CAS Registry No. 313266-85-2 added on STN on Jan. 9, 2001.
CAS Registry No. 294668-01-2 added on STN on Oct. 11, 2000.
CAS Registry No. 342653-87-6 added on STN on Jun. 20, 2001.
CAS Registry No. 449780-95-4 added on STN on Sep. 12, 2002.
CAS Registry No. 449780-94-3 added on STN on Sep. 12, 2002.
CAS Registry No. 324526-73-0 added on STN on Feb. 27, 2001.
Jan. 13, 2015 Russian Office Action issued in Russian Application No. 2011149572/04(074427).
Brandt et al. "Uncoupling Activity and Physicochemical Properties of Derivatives of Fluazinam". Biochimica et Biophysica Acta, Protein Structure and Molecular Enzymology, 1101(1): 41-7, abstract only CA 117:82915, 1992.
Dekker, Marcel. Ullmann's Encyclopedia of Industrial Chemistry, 6th Edition, 1989-1998.
Ansel et al. "Pharmaceutical Dosage Forms and Drugs Delivery Systems", 1994.
Gordon et al., "Hutchinson-Gilford Progeria Syndrome," NCBI Bookshelf, 2003, accessed Http://www.ncbi.nlm.gov/books/NBK1121/on Jan. 26, 2016,21 pages.
Feb. 16, 2016 Office Action Issued in U.S. Appl. No. 13/377,753.
Mar. 25, 2016 Office Action issued in U.S. Appl. No. 14/256,334.
Aug. 24, 2016 Office Action issued in U.S. Appl. No. 14/789,250.
Molina et al., "C=C-Conjugated Carbodiimides as 2-Azadienes in Intramolecular [4+2] Cycloadditions. One-Pot Preparation of Quinoline, alpha-Carboline, and Quinindoline Derivatives," J. Org. Chem., 1992, 57, 929-939.
Desai et al., "Some Quinoline, Quinazoilne and Pyrazine Derivatives as Antitubercular-Antibacterial Agents," Asian Journal of Chemistry, vol. 10, No. 4 (1998), 993-994.
Desai et al., "2-Methyl 4-quinoline-hydrazide Derivatives as Antitubercular/Antibacterial Agents—Part I," Asian Journal of Chemistry, vol. 10, No. 2 (1998), 370-372.
Oct. 3, 2015 Office Action issued in U.S. Appl. No. 13/377,753.
Sep. 27, 2016 Office Action issued in Chinese Application No. 201510023109.1.
Lin Min et al., "Nonsense-mediated mRNA decay and tumors," Journal of International Pathology and Clinical Medicine, vol. 26, No. 4, pp. 291-294.
Aug. 3, 2016 Office Action Issued in U.S. Appl. No. 14/256,334.
Jun. 21, 2016 Office Action issued in U.S. Appl. No. 14/789,149.
Dec. 5, 2016 Office Action Issued in U.S. Appl. No. 14/256,334.
Oct. 27, 2014 Office Action issued in U.S. Appl. No. 13/993,990.
Katoh et al. "Isolation of the intermediates and improved synthesis of pyrido[1',2':1 ,2]imidazo[4,5b]pyrazines and -quinoxalines", Heterocycles, 1992, 34(10), p. 1965-1972).
Carter et al., "Quinoxalines and related compounds-X1", Tetrahedron, 34(7), p. 981-988, 1978.
Lombardino, "Some 3-Arylaminoquinoxaline-2-carboxylic Acids", Journal of Medicinal Chemistry, 9(5), p. 770-771, 1996.
CAS Registry No. 1004363-48-7 added on STN on Feb. 19, 2008.
CAS Registry No. 438481-24-4 added on STN on Jul. 12, 2002.
CAS Registry No. 933238-11-0 added on STN on Apr. 29, 2007.
CAS Registry No. 1011408-51-7 added on STN on Apr. 1, 2008.
CAS Registry No. 1135230-99-7 added on STN on Apr. 16, 2009.
CAS Registry No. 374598-11-5 added on STN on Dec. 10, 2001.
Dudash et al., "Synthesis and Evaluation of 3-anilio-quinoxalinones as glycogen phosphorlyase inhibitors", Bioorganic & Medicinal Chemistry Letters, 15(21), p. 4790-4793, 2005.
Nov. 17, 2016 Office Action issued in Japanese Patent Application No. 2016-006105.
Nov. 16, 2016 Office Action issued in Japanese Patent Application No. 2016-006102.
Nov. 17, 2016 Office Action issued in Japanese Patent Application No. 2016-006104.
Loriga et al. "Quinoxaline Chemistry. Part 8. 2-[Anilino]-3-[Carboxy]-6(7)-Substituted Quinoxalines as Non Classical Antifolate Agents. Synthesis and Evaluation of Invitro Anticancer, Anti-HIV and Antifungal Activity". Farmaco, vol. 52, pp. 531-537, 1997.
CAPLUS Record for Loriga et al. "Part 8." (retrieved Nov. 2013).
Loriga et al. "Quinoxaline Chemistry. Part 7. 2-[Aminobenzoates]- and 2-[Aminobenzoylglutamate]-Quinoxalines as Classical Antifolate Agents. Synthesis and Evaluation of in Vitro Anticancer, Anti-HIV and Antifungal Activity." Farmaco, vol. 52, pp. 157-166, (pubMed Abstract No. 9212450), 1997.
CAPLUS Record for Loriga et al. "Part 7." (retrieved Nov. 2013).
Boganyi et al. "Syntheses of New Quinoline-Containing Heterocyclic Scaffolds Using Inter- and Intramolecular PD-Catalyzed Amination". J. Heterocyclic Chem., vol. 46, pp. 33-38, 2009.
Loones et al. "Synthesis of Pyrido[2, 1:2,3]Imidazo[4,5-B]Quinoline and Pyrido[1,2:1,2]Imidazo[4,5-B] Quinoline and Their Benzo and Aza Analogs Via Tandem Catalysis". Tetrahedron, vol. 63, pp. 8954-8961, 2007.
Perry et al. "AIDS dementia: a review of the literature". Alzheimer Dis. Assoc. Disord. 1, pp. 221-235, (PubMed Abstract 3331119), 1987.
Pauwels. "Aspects of Successful Drug Discovery and Development". Antiviral Res. vol. 71, pp. 77-89, 2006.
Respess et al. "Evaluation of an Ultrasensitive P24 Antigen Assay as a Potential Alternative to Human Immunodeficiency Virus Type 1 RNA Viral Load Assay in Resource-Limited Settings". J. Clin. Microbiol., vol. 43, pp. 506-508, 2005.
Jun. 27, 2011 International Search Report issued in International Patent Application No. PCT/IB2010/052652.
Jun. 27, 2011 Written Opinion of the International Searching Authority issued in International Patent Application No. PCT/IB2010/052652.
Aug. 9, 2011 International Search Report issued in International Patent Application No. PCT/IB2010/052651.
Aug. 9, 2011 Written Opinion of the International Searching Authority issued in International Patent Application No. PCT/IB2010/052651.
Apr. 13, 2011 International Search Report issued in International Patent Application No. PCT/IB2010/052650.
Apr. 13, 2011 Written Opinion of the International Searching Authority issued in International Patent Application No. PCT/IB2010/052650.
Dec. 10, 2009 Partial European Search Report issued in European Patent Application No. 09162630.9.
Nov. 19, 2009 European Search Report issued in European Patent Application No. 09305540.
Vulliamy et al. "Mutations in the Telomerase Component NHP2 Cause the Premature Ageing Syndrome Dyskeratosis Congenita". PNAS, vol. 105, No. 23, pp. 8073-8078, 2008.
Brune et al. "Progeria: A New Kind of Laminopathy—Clinical and Molecular Update of the Hutchinson-Gilford Syndrome". 1.sup.st European Symposium, 2003.
Park et al. "Efficient Palladium-Catalyzed Amination of Aryl Chlorides Using Dicyclo-Hexylamino[2,6-Dimethyl)Morpholino]Phenylphosphine as a PN.Sub.2 Ligand". Synthesis, No. 5, pp. 0815-0823, 2009.
Loones et al. "Examination of the Mechanism of the Intramolecular Amination of N-(3-Bromopyridin-2-Yl)Azaheteroarylamines and N-(2-Chloropyridin-3-Yl)Azaheteroarylamines: a Pd-Catalyzed Amination and/or a Base-Assisted Nucleophilic; Aromatic Substitution?". Tetrahedron, vol. 63, pp. 3818-3825, 2007.
Dhanabal et al. "Heteroatom Directed Photoannulation: Synthesis of Indoloquinoline Alkaloids: Cryptolepine, Cryptotackieine, Cryptosanguinolentine, and Their Methyl Derivatives". Tetrahedron, vol. 62, pp. 6258-6263, 2006.
Fors et al. "An Efficient Process for Pd-Catalyzed C—N Cross-Coupling Reactions of Aryl Iodides: Insight Into Controlling Factors," Journal of the American Chemical Society, 2009, vol. 131, No. 16, 5766-5768.
Jonckers et al. "Selective Palladium-Catalyzed Aminations of Dicholoropyridines," Tetrahedron, 2001, vol. 57, pp. 7027-7034.
Kaczmarek et al. "Synthesis and Antineoplastic Properties of Some Benzoiso-.Alpha.-Carbolines". Archiv Der Pharmazie, Weinheim, Germany, vol. 321, No. 8, pp. 463-467, 1988.
Solekhova et al. "Reductive Amination of Quinoline N-Oxide With Aminopyridines and Their N-Tosyl Derivatives". Russian Journal of Organic Chemistry, vol. 38, No. 8, pp. 1192-1194, 2002.
Nguyen et al. "Synthesis and Biological Evaluation of Amino-Substituted Benzo [F]Pyrido[4,3-B] and Pyrido[3,4-

B]Quinoxalines: A New Class of Antineoplastic Agents". Anti-Cancer Drug Design, vol. 10, No. 4, pp. 277-297, (abstract only). 1995.

Baklanov et al. "Photocyclization of (O-Haloary)Hetarylamines". Zhurnal Organicheskoi Khimii, vol. 27, No. 3, pp. 638-649 (abstract only), 1991.

Ducrocq et al. "Synthesis of 10-Substituted 5H-Pyrido[3',4':4,5]Pyrrolo[2,3-]Isoquinolines". Journal of the Chemical Society, Perkin Transactions 1: Organic and Bio-Organic Chemistry (1972-1999), vol. 1, pp. 142-145, 1979.

Prostakov et al. "Schiff Bases in Syntheses of Substituted Naphthylamines, Napthyridines, Azophenanthrenes, and Benzocarbazole". Khimiya Geterotsiklicheskikh Soedinenii, vol. 10, pp. 1400-1403 (abstract only), 1972.

Grout et al. "Polyazabenzo [A] Pyrenes". Journal of the Chemical Society [Section] C: Organic, vol. 21, pp. 2689-2693, 1968.

Talik et al. "2-Chloro-3, 5-Dinitropyridine. 1. Exchange Reactions of the Chlorine Atom". Bulletin de L'Academie Polonaise des Sciences, Serie Des Sciences Chimiques, vol. 8, No. 5, pp. 219-222 (abstract only), 1960.

Deuerleine, "Dipryridyl-, Diquinolyl-, and Pyridylquinolylamines". Journal fuer Praktische Chemie (Liepzig), vol. 106, pp. 53-65 (abstract only), 1923.

Kondratenko et al. "Bactericidal Activity of Some Derivatives of N-Heteroaromatic Compounds". Mikrobiologichnii Zhurnal, 1934-1977, vol. 40, No. 3, pp. 368-370 (abstract only), 1978.

Gritsenko et al. "Synthesis in Phenothiazines. XXXIX. Dimethylpyridophenothiazines". Khimiya Geterotsiklicheskikh Soedinenii, vol. 1, pp. 50-54 (abstract only),1975.

Buchmann et al. "The Preparation and Reactivity of 4-Hydroxy-7-Chloroquinaldine". Journal fuer Praktische Chemie, vol. 17, pp. 135-146 (abstract only), 1962.

Khalifa. "Hutchinson-Gilford Progeria Syndrome: Report of a Libyan Family and Evidence of Autosomal Recessive Inheritance". Clinical Genetics, vol. 35, pp. 125-132, 1989.

De Sandre-Giovannoli et al. "Lamin A Truncation in Hutchinson-Gilford Progeria". Science, vol. 300, p. 2055, 2003.

Pendas et al. "Defective Prelamin A Processing and Muscular and Adipocyte Alterations in ZMPSTE24 Metalloproteinsase-Deficient Mice". Nature Genetics, vol. 31, pp. 94-99, 2002.

De Sandre-Giovannoli et al. "Altered Splicing in Prelamin A-Associated Premature Aging Phenotypes". Progress in Molecular and Subcellular Biology, pp. 199-232, 2006.

Fong et al. "A Protein Farnesyltransferase Inhibitor Ameliorates Disease in a Mouse Model of Progeria". Science, vol. 311, pp. 1621-1623, 2006.

Varela et al. "Combined Treatment With Statins and Aminobisphosphonates Extends Longevity a Mouse Model of Human Premature Aging". Nature Medicine, vol. 14, No. 7, pp. 767-772, 2008.

Labourier et al. "Recognition of Exonic Splicing Enhancer Sequences by the *Drosophila* Splicing Repressor RSF1". Nucleic Acids Research, vol. 27, No. 11, pp. 2377-2386, 1999.

Dignam et al. "Eukaryotic Gene Transcription With Purified Components". Methods in Enzymology, vol. 101, pp. 582-598, 1983.

Tazi et al. "A Protein That Specifically Recognizes the 3' Splice Site of Mammalian Pre-MRNA Introns Is Associated With a Small Nuclear Ribonucleoprotein" Cell, vol. 47, pp. 755-766, 1986.

Sanchez-Martin et al. "Symmetrical Bis-Quinolinium Compounds: New Human Choline Kinase Inhibitors with Antiproliferative Activity against the HT-29 Cell Line". Journal of Medicinal Chemistry, vol. 48, No. 9, pp. 3354-3363, 2005.

Cottet et al. "Recommendable Routes to Trifluoromethyl-Substituted Pyridine-and Quinolinecarboxylic Acids". Eur. J. Org. Chem., pp. 1559-1568, 2003.

Balkau et al. "Syntheis of Ellipticine Intermediates: 6-Amino-, 6-Hydroxy-, and 6-Methoxy-5,8-Dimethylisoquinoline". Australian. J. Chem., vol. 22, pp. 2489-2492, 1969.

Sharp. "Split Genes and RNA Splicing". Cell, vol. 77, pp. 805-815, 1994.

Black. "Mechanisms of Alternative Pre-Messenger RNA Splicing". Annu. Rev. Biochem., vol. 72, pp. 291-336, 2003.

Oct. 3, 2016 Office Action issued in U.S. Appl. No. 13/377,753.

CAS Registry No. 330663-16-6 added on STN on Apr. 10, 2001.

Jul. 15, 2016 Office Action issued in Japanese Application No. 2015-120567.

U.S. Appl. No. 15/326,698, filed Jan. 17, 2017 in the name of Tazi et al.

Jan. 17, 2017 International Preliminary Report on Patentability issued in International Patent Application No. PCT/EP2015/066462.

Sep. 22, 2015 International Search Report issued in International Patent Application No. PCT/EP2015/066462.

Ex Parte Gerard Marguierie and Eric Malaud, PTAB 2016, Appeal 2013-004606, U.S. Appl. No. 10/587,697, 7 pages.

Apr. 6, 2017 Office Action Issued in U.S. Appl. No. 13/377,751.

Oct. 3, 2017 Office Action issued in U.S. Appl. No. 14/789,250.

Jun. 27, 2017 Office Action Issued in U.S. Appl. No. 14/789,250.

May 5, 2017 Office Action issued in Chinese Application No. 201510023124.6.

* cited by examiner

COMPOUNDS USEFUL FOR TREATING DISEASES CAUSED BY RETROVIRUSES

The compounds described herein are useful for the treatment of diseases resulting from changes in splicing processes.

Viruses, in particular from the retroviral family, are one of the major causes of diseases around the world. Three subfamilies can be distinguished within the retroviral family: the oncoviruses, the lentiviruses and the spumaviruses.

The oncoviruses are thus termed because they can be associated with cancers and malignant infections. There may be mentioned, for example, leukemogenic viruses such as the avian leukemia virus (ALV), the murine leukemia virus (MULV), also called Moloney virus, the Abelson leukemia virus, the murine mammary tumor virus, the Mason-Pfizer monkey virus (or MPMV), the feline leukemia virus (FELV), human leukemia viruses such as HTLV1 (also, named HTLV-I) and HTLV2 (also named HTLV-II), the simian leukemia virus or STLV, the bovine leukemia virus or BLV, the primate type D oncoviruses, the type B oncoviruses which are inducers of mammary tumors, or oncoviruses which cause a rapid cancer (such as the Rous sarcoma virus or RSV).

Although the term oncovirus is still commonly used, other terms can also be used such as Alpharetrovirus for avian leukosis virus and Rous sarcoma virus; Betaretrovirus for mouse mammary tumor virus; Gammaretrovirus for murine leukemia virus and feline leukemia virus; Deltaretrovirus for bovine leukemia virus and human T-lymphotropic virus; and Epsilonretrovirus for Walleye dermal sarcoma virus.

The spumaviruses manifest fairly low specificity for a given cell type or a given species, and they are sometimes associated with immunosuppressive phenomena; that is the case, for example, for the simian foamy virus (or SFV), also named chimpanzee simian virus, the human foamy virus (or HFV), bovine syncytial virus (or BSV), feline syncytial virus (FSV) and the feline immunodeficiency virus.

The lentiviruses, such as Human Immunodeficiency Virus (HIV, also known as HTLV-III or LAV for lymphotrophic adenovirus and which can be distinguished within HIV-1 and HIV-2), are thus named because they are responsible for slow-progressing pathological conditions which very frequently involve immunosuppressive phenomena, including AIDS. Among the lentiviruses, the visna/maedi virus (or MVV/Visna), equine infectious anemia virus (EIAV), caprine arthritis encephalitis virus (CAEV), simian immunodeficiency virus (SIV) can also be cited. Certain indole derivative compounds such as ellipticine derivatives and aza-ellipticine derivatives are already known as intercalating molecules for correcting dysfunctions in gene expression, notably in DNA replication. They have been more specifically described for treating diseases such as cancer, leukemia or AIDS (see in particular patents FR 2 627 493, FR 2 645 861, FR 2 436 786).

Intracellular splicing consists of eliminating introns in pre-messenger RNAs to produce mature messenger RNAs that can be used by the translation mechanism of the cell (SHARP, *Cell*, vol. 77, p. 805-815, 1994). In the case of alternative splicing, the same precursor can be the source of messenger RNAs coding for proteins with distinct functions (BLACK, *Annu. Rev. Biochem.* vol. 72, p. 291-336, 2003). The precise selection of 5' and 3' splicing sites is thus a mechanism that generates diversity and that can lead to the regulation of gene expression according to the type of tissue or during the development of an organism. The factors involved in this selection include a family of proteins called SR, characterized by the presence of one or two RNA recognition motifs (RRM) and a domain rich in arginine and serine residues called an RS domain (MANLEY & TACKE, *Genes Dev.*, vol. 10, p. 1569-1579, 1996). By binding to short exon or intron sequences of the pre-mRNA, called ESE (exonic splicing enhancer) or ISE (intronic splicing enhancer), SR proteins are able to activate, in a dose-dependent manner, sub-optimal splicing sites and to enable the inclusion of exons (GRAVELEY, *RNA*, vol. 6, p. 1197-1211, 2000). The activity of an SR protein in alternative splicing is specific insofar as the inactivation of the corresponding gene is lethal (WANG et al., *Mol. Cell*, vol. 7, p. 331-342, 2001).

Sequencing of the human genome and analysis of EST (expressed sequence tag) banks has revealed that 65% of genes are expressed in the form of alternatively spliced variants (EWING & GREEN, *Nat. Genet.*, vol. 25, p. 232-234, 2000; JOHNSON et al., *Science*, vol. 302, p. 2141-2144, 2003). This mechanism is thus a favored target of modifications that can affect the factors involved in regulating splicing and of mutations that affect the sequences necessary for this regulation. At present, it is estimated that roughly 50% of the point mutations responsible for genetic diseases induce aberrant splicing. These mutations can interfere with splicing by inactivating or creating splicing sites, but also by modifying or generating regulating elements such as splicing enhancers or splicing silencers in a particular gene (CARTEGNI et al., *Nat. Rev. Genet.*, vol. 3, p. 285-298, 2002; TAZI et al., *TIBS*, vol. 40, p. 469-478, 2005).

The strategies currently developed to correct these splicing defects rest on the use of various types of molecules (TAZI et al., cited above, 2005).

One strategy aimed at developing novel molecules to correct or eliminate abnormal splicing, for example, rests on the overexpression of proteins that interfere with this type of splicing (NISSIM-RAFINIA et al., *Hum. Mol. Genet.*, vol. 9, p. 1771-1778, 2000; HOFINANN et al., *Proc. Natl. Acad. Sci. U.S.A.*, vol. 97, p. 9618-9623, 2000).

Other strategies rest on the use of antisense oligonucleotides (SAZANI et al., *Nat. Biotechnol.*, vol. 20, p. 1228-1233, 2002; SAZANI & KOLE, *Prog. Mol. Subcell. Biol.*, vol. 31, p. 217-239, 2003) or of PNA (CARTEGNI et al., *Nat. Struct. Biol.*, vol. 10, p. 120-125, 2003) enabling, respectively, the inhibition or activation of a splicing event.

Yet another strategy rests on the identification of compounds that influence the splicing efficiency of the pre-mRNA of interest (ANDREASSI et al., *Hum. Mol. Genet.*, vol. 10, p. 2841-2849, 2001).

Lastly, a strategy based on the use of trans-splicing to replace mutant exons has been described (LIU et al., *Nat. Biotechnol.*, vol. 20, p. 47-52, 2002).

One of the disadvantages of the developed strategies cited above to correct or eliminate abnormal splicing is their production cost. Indeed, the cost of producing antisense oligonucleotides that must be modified to improve their stability, and that of PNA molecules, is high.

Another disadvantage of the developed strategies cited above is that they require the use of expression vectors, such as, for example, for the strategy based on the use of trans-splicing.

International application WO05023255, under French priority of applications FR0310460 and FR0400973, filed by the Applicant, disclosed the use of indole derivatives to treat diseases related to the pre-messenger RNA splicing process in the cell.

Thus it was recently shown that certain indole derivatives prove particularly effective in treating metastatic cancer and in treating AIDS (BAKKOUR et al., *PLoS Pathogens*, vol. 3, p. 1530-1539, 2007).

However, the compounds described have a flat structure with four rings that have the disadvantage of intercalating between DNA bases and can thus lead to cellular toxicity.

In order to minimize the risk that these indole derivatives intercalate between DNA bases, the inventors developed novel compounds that are particularly effective in treating diseases related to the splicing process, but which, in a surprising manner, have a cellular toxicity that is clearly less than the indole derivatives of the prior art. In addition, these compounds are able to selectively inhibit certain splicing events.

In certain aspects, the methods described herein include contacting a cell having a retroviral infection with at least one of the compounds described below, wherein the retroviral infection does not include HIV. In another aspect, the methods described herein include inhibiting RNA splicing of a retrovirus by administering a compound to a subject in need thereof, wherein the compound includes at least one compound described below and the retrovirus does not include HIV. In yet another aspect, the methods described herein include methods for treating a retroviral infection or a disease caused by the retroviral infection comprising administering an effective amount of a pharmaceutical composition to a subject in need thereof, wherein the pharmaceutical composition includes at least one compound described herein and the retroviral infection does not include HIV and the disease caused by the retroviral infection does not include AIDS.

According to a first aspect, the compound of formula (I)

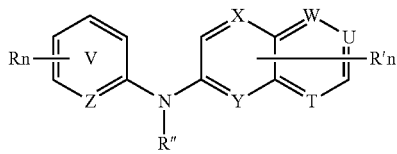

(I)

wherein:

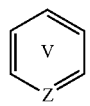

means an aromatic ring wherein V is C or N and when V is N, V is in ortho, meta or para of Z, i.e. forms respectively a pyridazine, a pyrimidine or a pyrazine group, R independently represent a hydrogen atom, a halogen atom or a group chosen among a —CN group, a hydroxyl group, a —COOR$_1$ group, a (C$_1$-C$_3$)fluoroalkyl group, a (C$_1$-C$_3$)fluoroalkoxy group, a —NO$_2$ group, a —NR$_1$R$_2$ group, a (C$_1$-C$_4$)alkoxy group, a phenoxy group and a (C$_1$-C$_3$)alkyl group, said alkyl being optionally mono-substituted by a hydroxyl group, R$_1$ and R$_2$ are independently a hydrogen atom or a (C$_1$-C$_3$)alkyl group, n is 1, 2 or 3, n' is 1 or 2, R' is a hydrogen atom or a group chosen among a (C$_1$-C$_3$)alkyl group, a halogen atom, a hydroxyl group, a —COOR$_1$ group, a —NO$_2$ group, a —NR$_1$R$_2$ group, a morpholinyl or a morpholino group, a N-methylpiperazinyl group, a (C$_1$-C$_3$)fluoroalkyl group, a (C$_1$-C$_4$)alkoxy group and a —CN group, R" is a hydrogen atom or a (C$_1$-C$_4$)alkyl group, Z is N or C, Y is N or C, X is N or C, W is N or C, T is N or C, U is N or C, and wherein at most four of the groups V, T, U, Z, Y, X and W are N, and at least one of the groups T, U, Y, X and W is N, or anyone of its pharmaceutically acceptable salt, can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to one aspect, the compound of formula (I) as defined above, wherein Z is N, V is C, Y is N, X is C, T is C, U is C and W is C, for use as an agent for preventing or treating the infection of a cell and/or an individual, preferably a human, in need thereof by a retrovirus and/or for preventing retrovirus and/or for preventing, inhibiting or treating a disease caused by retroviruses.

According to another aspect, the compound of formula (I) as defined above, wherein Z is C, V is C, Y is N, X is C, T is C, U is C and W is C, for use as an agent for preventing or treating the infection of a cell and/or an individual, preferably a human, in need thereof by a retrovirus and/or for preventing retrovirus and/or for preventing, inhibiting or treating a disease caused by retroviruses.

According to another aspect, the compound of formula (I) as defined above, wherein Z is N, V is C, Y is C, X is N, T is C, U is C and W is C, for use as an agent for preventing or treating the infection of a cell and/or an individual, preferably a human, in need thereof by a retrovirus and/or for preventing retrovirus and/or for preventing, inhibiting or treating a disease caused by retroviruses.

According to another aspect, the compound of formula (I) as defined above, wherein Z is N, V is C, Y is C, X is C, T is C, U is C and W is N, for use as an agent for preventing or treating the infection of a cell and/or an individual, preferably a human, in need thereof by a retrovirus and/or for preventing retrovirus and/or for preventing, inhibiting or treating a disease caused by retroviruses.

According to another aspect, the compound of formula (I) as defined above, wherein Z is N, V is N and is in para of Z, Y is N, X is C, T is C, U is C and W is C, for use as an agent for preventing or treating the infection of a cell and/or an individual, preferably a human, in need thereof by a retrovirus and/or for preventing, inhibiting or treating a disease caused by retroviruses.

According to another aspect, the compound of formula (I) as defined above, wherein Z is C, V is N and is in para of Z, Y is C, X is N, T is C, U is C and W is C, for use as an agent for preventing or treating the infection of a cell and/or an individual, preferably a human, in need thereof by a retrovirus and/or for preventing, inhibiting or treating a disease caused by retroviruses.

According to another aspect, the compound of formula (I) as defined above, wherein Z is C, V is N and is in meta of Z and is in para of the bond linked to NR", Y is N, X is C, T is C, U is C and W is C, for use as an agent for preventing or treating the infection of a cell and/or an individual, preferably a human, in need thereof by a retrovirus and/or for preventing, inhibiting or treating a disease caused by retroviruses.

According to another aspect, the compound of formula (I) as defined above, wherein Z is C, V is N and is in meta of Z and is in para of the bond linked to NR", Y is C, X is N, T is C, U is C and W is C, for use as an agent for preventing or treating the infection of a cell and/or an individual, preferably a human, in need thereof by a retrovirus and/or for preventing, inhibiting or treating a disease caused by retroviruses.

According to another aspect, the compound of formula (I) as defined above, wherein Z is C, V is C, Y is C, X is N, T is C, U is C and W is C, for use as an agent for preventing or treating the infection of a cell and/or an individual, preferably a human, in need thereof by a retrovirus and/or for preventing, inhibiting or treating a disease caused by retroviruses.

According to another aspect, the compound of formula (I) as defined above, wherein Z is C, V is C, Y is N, X is N, T is C, U is C and W is C, for use as an agent for preventing or treating the infection of a cell and/or an individual, preferably a human, in need thereof by a retrovirus and/or for preventing, inhibiting or treating a disease caused by retroviruses.

According to another aspect, the compound of formula (I) as defined above, wherein Z is N, V is N and is in meta of Z and in ortho of the bond linked to NR", Y is N, X is C, T is C, U is C and W is C, for use as an agent for preventing or treating the infection of a cell and/or an individual, preferably a human, in need thereof by a retrovirus and/or for preventing, inhibiting or treating a disease caused by retroviruses.

According to another aspect, the compound of formula (I) as defined above, wherein Z is N, V is N and is in para of Z, Y is C, X is C, T is C, U is C and W is N, for use as an agent for preventing or treating the infection of a cell and/or an individual, preferably a human, in need thereof by a retrovirus and/or for preventing, inhibiting or treating a disease caused by retroviruses.

According to another aspect, the compound of formula (I) as defined above, wherein Z is N, V is N and is in para of Z, Y is C, X is N, T is C, U is C and W is C, for use as an agent for preventing or treating the infection of a cell and/or an individual, preferably a human, in need thereof by a retrovirus and/or for preventing, inhibiting or treating a disease caused by retroviruses.

According to another aspect, the compound of formula (I) as defined above, wherein Z is N, V is C, Y is N, X is N, T is C, U is C and W is C, for use as an agent for preventing or treating the infection of a cell and/or an individual, preferably a human, in need thereof by a retrovirus and/or for preventing, inhibiting or treating a disease caused by retroviruses.

According to another aspect, the compound of formula (I) as defined above, wherein Z is N, V is N and is in meta of Z and is in ortho of the bond linked to NR", Y is N, X is N, T is C, U is C and W is C, for use as an agent for preventing or treating the infection of a cell and/or an individual, preferably a human, in need thereof by a retrovirus and/or for preventing, inhibiting or treating a disease caused by retroviruses.

According to another aspect, the compound of formula (I) as defined above, wherein Z is C, V is C, Y is C, X is C, T is N, U is C and W is C, for use as an agent for preventing or treating the infection of a cell and/or an individual, preferably a human, in need thereof by a retrovirus and/or for preventing, inhibiting or treating a disease caused by retroviruses.

According to another aspect, the compound of formula (I) as defined above, wherein Z is N, V is C, Y is C, X is C, T is N, U is C and W is C, for use as an agent for preventing or treating the infection of a cell and/or an individual, preferably a human, in need thereof by a retrovirus and/or for preventing, inhibiting or treating a disease caused by retroviruses.

According to another aspect, the compound of formula (I) as defined above, wherein Z is N, V is C, Y is C, X is C, T is C, U is N and W is C, for use as an agent for preventing or treating the infection of a cell and/or an individual, preferably a human, in need thereof by a retrovirus and/or for preventing, inhibiting or treating a disease caused by retroviruses.

The compounds described herein may exist in the form of free bases or of addition salts with pharmaceutically acceptable acids.

Suitable physiologically acceptable acid addition salts of compounds of formula (I) include hydrobromide, tartrate, citrate, trifluoroacetate, ascorbate, hydrochloride, tartrate, triflate, maleate, mesylate, formate, acetate and fumarate.

The compounds of formula (I) and or salts thereof may form solvates (e.g. hydrates).

As disclosed herein, the term:

"halogen" is understood to mean chlorine, fluorine, bromine, or iodine, and in particular denotes chlorine, fluorine or bromine, "($C_1$-$C_3$)alkyl" as used herein respectively refers to $C_1$-$C_3$ normal, secondary or tertiary saturated hydrocarbon. Examples are, but are not limited to, methyl, ethyl, 1-propyl, 2-propyl, "($C_1$-$C_3$)alkoxy" as used herein respectively refers to O—($C_1$-$C_3$)alkyl moiety, wherein alkyl is as defined above. Examples are, but are not limited to, methoxy, ethoxy, 1-propoxy, 2-propoxy, "fluoroalkyl group" and "fluoroalkoxy group" refers respectively to alkyl group and alkoxy group as above-defined, said groups being substituted by at least one fluorine atom. Examples are perfluoroalkyl groups, such as trifluoromethyl or perfluoropropyl, and "individual" and "patient" may extend to humans or mammals, such as cats or dogs.

According to one preferred aspect, the compound of formula (I) as defined above, wherein Z is N, V is C, Y is N, X is C, T is C, U is C and W is C, for use as an agent for preventing or treating the infection of a cell and/or an individual, preferably a human, in need thereof by a retrovirus and/or for preventing, inhibiting or treating a disease caused by retroviruses.

According to another preferred aspect, the compound of formula (I) as defined above, wherein Z is C, V is C, Y is N, X is C, T is C, U is C and W is C, for use as an agent for preventing or treating the infection of a cell and/or an individual, preferably a human, in need thereof by a retrovirus and/or for preventing, inhibiting or treating a disease caused by retroviruses.

According to another preferred aspect, the compound of formula (I) as defined above, wherein Z is N, V is C, Y is C, X is N, T is C, U is C and W is C, for use as an agent for preventing or treating the infection of a cell and/or an individual, preferably a human, in need thereof by a retrovirus and/or for preventing, inhibiting or treating a disease caused by retroviruses.

According to another preferred aspect, the compound of formula (I) as defined above, wherein Z is N, V is N and is in para of Z, Y is N, X is C, T is C, U is C and W is C, for use as an agent for preventing or treating the infection of a cell and/or an individual, preferably a human, in need thereof by a retrovirus and/or for preventing, inhibiting or treating a disease caused by retroviruses.

According to another preferred aspect, the compound of formula (I) as defined above, wherein Z is N, V is C, Y is N, X is N, T is C, U is C and W is C, for use as an agent for preventing or treating the infection of cell and/or an individual, preferably a human, in need thereof by a retrovirus and/or for preventing, inhibiting or treating a disease caused by retroviruses.

Another object described herein relates to a compound of the following formula (I'):

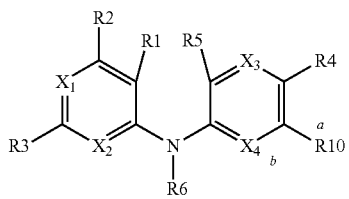

wherein:
X1, X2 and X3 independently represent a nitrogen atom, or a CR8 group, at least one of X1 and X2 being a nitrogen atom;
R8 represents a hydrogen atom or a halogen atom, a hydroxyl, alkyl, trifluoroalkyl, ester, ether, such as a methoxy or trifluoromethoxy group, or benzyl, optionally substituted, a nitro or a cyano group, preferably R8 represents a hydrogen atom,
when a ring A, defined below, is in position a, X4 represents a nitrogen atom or a CR8 group, and when a ring A is in position b, X4 represents a carbon atom part of the ring A,
R1, R2, R3 and R5 independently represent a hydrogen or a halogen atom, an alkyl, a trifluoroalkylgroup, ether, such as a methoxy or trifluoromethoxy group, or benzyl, optionally substituted, a nitro or a cyano group.

when the ring A is at position b, R4 represents a hydrogen atom, a halogen atom or an alkyl, a trifluoroalkyl, ester, ether group, such as a methoxy or trifluoromethoxy group, or benzyl, optionally substituted, and when the ring A is at position a, R4 is a carbon atom part of the ring A,
R10 represents a carbon atom part of ring A,
R6 represents a hydrogen atom or an alkyl group,
A represents a ring at position a or b of formula I, said ring A corresponding to:

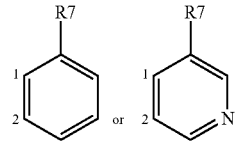

wherein:
R7 represents a hydrogen, or halogen atom or an alkyl, hydroxyl or amine group which can be linear or branched and/or unsaturated and optionally substituted, pharmaceutically acceptable salts of said compounds, isomers thereof and/or mixtures of the same can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

with the exception of the following compound:

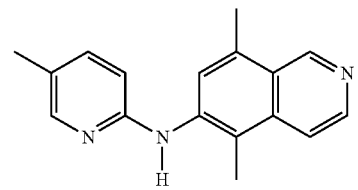

"Halogen atom" means the group comprising F, Cl, Br and I, preferably said halogen atom is a chlorine atom.

"Unsaturated" means that the group comprises at least one double bond.

Preferably, X1 represents a CR8 group when X2 represents a nitrogen group, and

X2 represents a CR8 group when X1 represents a nitrogen group.

Preferably, at least one of X3 and X4 is a nitrogen atom when the cycle A is in position a.

Preferably X3 and X4 are different, and even more preferably X3 represents a CR8 group when X2 represents a nitrogen group or a and X4 represents a CR8 group when X1 represents a nitrogen group.

Preferably, R1 represents a hydrogen atom or a methoxy group.

Preferably, R2, R3, R4 and R5 independently represent a hydrogen atom or a halogen atom or an alkyl, or benzyl, optionally substituted.

Preferably, R4 represents a hydrogen atom.

Preferably, R2 represents a hydrogen atom or a C1 to C4 alkyl group, preferably a methyl.

Preferably, R3, R5 and R6 independently represent a hydrogen atom.

Preferably, R7 represents a hydrogen, or halogen atom, more preferably a hydrogen or a chlorine atom.

Preferably, the ring A is attached at position a or b of the compound of formula I via the carbons numbered 1 and 2 in ring A.

Preferably, when the ring A is at position a, R4 is the carbon atom numbered 2 of the ring A, more preferably R4 is the carbon atom numbered 2 of the ring A and R10 is the carbon numbered 1.

Preferably, when a ring A is in position b, X4 is the carbon atom numbered 1 of the ring A, more preferably, X4 is the carbon atom numbered 1 of the ring A and R10 is the carbon numbered 2.

Preferably, the compound as described above does not include the following compounds:

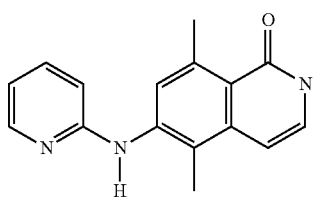 [SMILES: Cc1c(Nc2ccccn2)cc(C)c2c(=O)[nH]ccc12]

5,8-Dimethyl-6-(pyridin-2-ylamino)-2H-isoquinolin-1-one

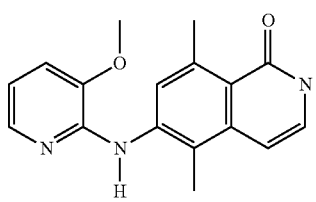 [SMILES: COc1cccnc1Nc1cc(C)c2c(=O)[nH]ccc2c1C]

5,8-dimethyl-6-(3 methoxy-pyridin-2-ylamino)-isoquinolin-1-one

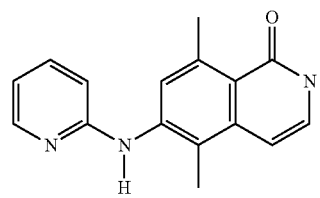 [SMILES: Cc1c(Nc2ccccn2)cc(C)c2c(=O)[nH]ccc12]

5,8-Dimethyl-6-(pyridin-2-ylamino)-2H-isoquinolin-1-one

Advantageously, the compound of formula I is chosen among the group comprising:

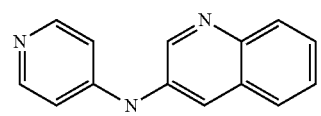 [SMILES: c1ccc2ncc(Nc3ccncc3)cc2c1]

Pyridin-4-yl-quinolin-3-yl-amine; compound (121) of table I

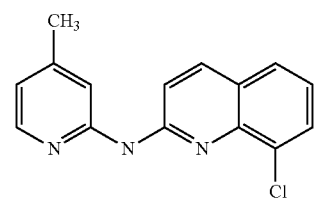 [SMILES: Cc1ccnc(Nc2ccc3cccc(Cl)c3n2)c1]

(8-Chloro-quinolin-2-yl)-(4-methyl-pyridin-2-yl)-amine; compound (6) of table I

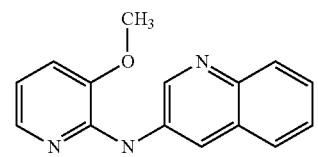 [SMILES: COc1cccnc1Nc1cnc2ccccc2c1]

(3-Methoxy-pyridin-2-yl)-quinolin-3-yl-amine; compound (10) of table I; and

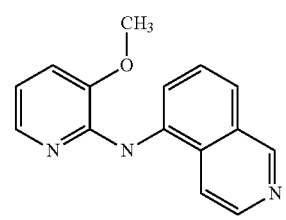 [SMILES: COc1cccnc1Nc1cccc2cnccc12]

Isoquinolin-5-yl-(3-methoxy-pyridin-2-yl)-amine.

According to a particular embodiment, compound of formula (Ia)

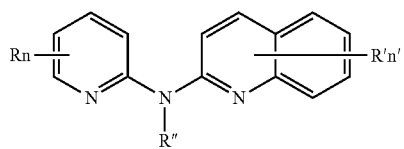

(Ia)

wherein:

R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a —NO$_2$ group, a —NR$_1$R$_2$ group and a $(C_1-C_3)$alkoxy group, R" is as defined above and is advantageously a hydrogen atom, n is as defined above and is advantageously 1, n' is as defined above and is advantageously 1, R' is a hydrogen atom, a halogen atom or a group chosen among a $(C_1-C_3)$alkyl group, a —NO$_2$ group, a $(C_1-C_3)$alkoxy group and a —NR$_1$R$_2$ group, R$_1$ and R$_2$ are a hydrogen atom or a $(C_1-C_3)$alkyl group, or one of its pharmaceutically acceptable salt, can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Ib)

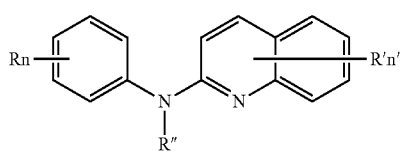

(Ib)

wherein:

R independently represent a hydrogen atom, a halogen atom or a group chosen among a $(C_1-C_3)$alkyl group, a —NR$_1$R$_2$ group, a $(C_1-C_3)$fluoroalkoxy group, a —NO$_2$ group, a phenoxy group and a $(C_1-C_4)$alkoxy group, R$_1$ and R$_2$ are independently a hydrogen atom or a $(C_1-C_3)$alkyl group, R" is as defined above and is advantageously a hydrogen atom, n is as defined above and is preferably 1 or 2, n' is as defined above and is preferably 1, R' is a hydrogen atom, a halogen atom or a group chosen among a $(C_1-C_3)$alkyl group and a $(C_1-C_4)$alkoxy group, or one of its pharmaceutically acceptable salt, can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Ic)

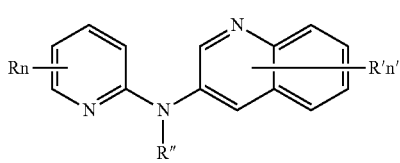

(Ic)

wherein:

R independently represent a hydrogen atom or a group chosen among a $(C_1-C_3)$alkyl group, a $(C_1-C_3)$fluoroalkyl group, a —NR$_1$R$_2$ group, a —COOR$_1$ group, a —NO$_2$ group and a $(C_1-C_3)$alkoxy group, R" is as defined above and is advantageously a hydrogen atom, n is as defined above and is advantageously 1, n' is as defined above and is advantageously 1, R' is a hydrogen atom, R$_1$ and R$_2$ are independently a hydrogen atom or a $(C_1-C_3)$alkyl group, or one of its pharmaceutically acceptable salt, can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Id)

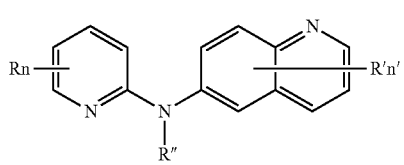

wherein:
R independently represent a hydrogen atom or a group chosen among a $(C_1-C_3)$alkyl group, a $(C_1-C_3)$fluoroalkyl group and a $(C_1-C_3)$alkoxy group,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Ie)

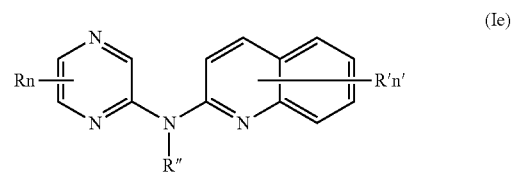

wherein:
R represents a hydrogen atom,
R" is as defined above and is advantageously a hydrogen atom,
n is as defined above and is advantageously 1,
n' is as defined above and is advantageously 1,
R' is a hydrogen atom, a halogen atom or a group chosen among a $(C_1-C_3)$alkyl group and a $(C_1-C_3)$alkoxy group,
or one of its pharmaceutically acceptable salt,
can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment compound of formula (If)

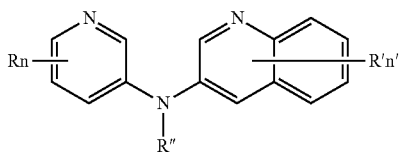

(If)

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Ig)

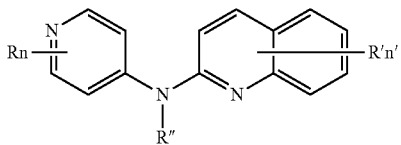

(Ig)

wherein:
R represents a hydrogen atom,
R" is as defined above and is advantageously a hydrogen atom,
n is as defined above and is advantageously 1,
n' is as defined above and is advantageously 1,
R' is a hydrogen atom or a halogen atom,
or one of its pharmaceutically acceptable salt,
can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Ih)

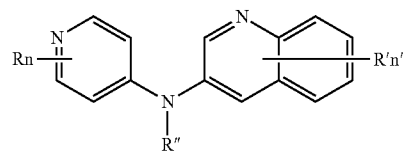

(Ih)

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Ii)

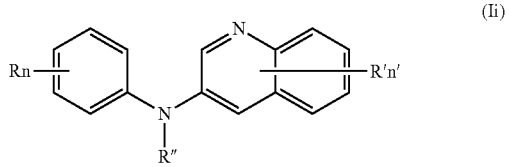

wherein:

R independently represent a hydrogen atom or a group chosen among a $(C_1-C_3)$fluoroalkoxy group and a $(C_1-C_3)$ alkoxy group, R" is as defined above and is advantageously a hydrogen atom, n is as defined above and is advantageously 1, n' is as defined above and is advantageously 1, R' is a hydrogen atom, or one of its pharmaceutically acceptable salt, can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Ij)

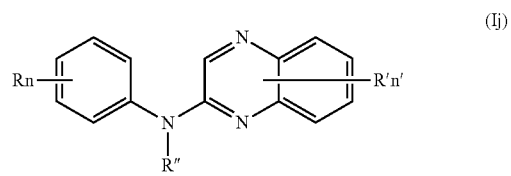

wherein:

R independently represent a hydrogen atom or a group chosen among a $(C_1-C_3)$fluoroalkoxy group and a $(C_1-C_3)$ alkyl group, R" is as defined above and is advantageously a hydrogen atom, n is as defined above and is advantageously 1, n' is as defined above and is advantageously 1, R' is a hydrogen atom, or one of its pharmaceutically acceptable salt, can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Ik)

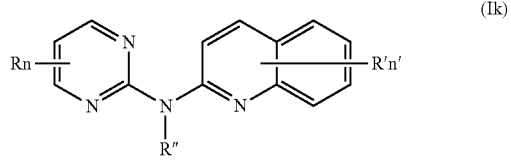

wherein:

R represents a hydrogen atom,

R" is as defined above and is advantageously a hydrogen atom, n is as defined above and is advantageously 1, n' is as defined above and is advantageously 1, R' is a hydrogen atom, a halogen atom or a $(C_1-C_3)$alkyl group, or one of its pharmaceutically acceptable salt, can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Il)

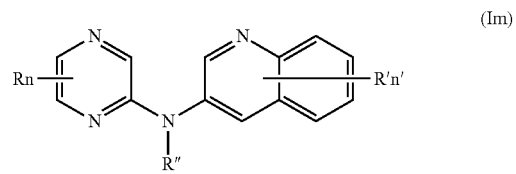

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Im)

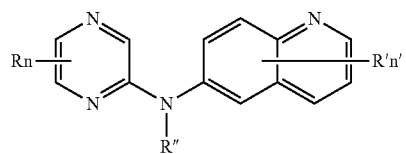

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Io)

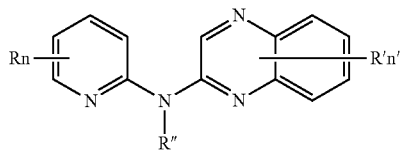

(Io)

wherein:

R independently represent a hydrogen atom or a halogen atom or a group chosen among, a —NO$_2$ group, a —CN group and a (C$_1$-C$_3$)alkyl group, said alkyl being optionally mono-substituted by a hydroxyl group, R″ is as defined above and is advantageously a hydrogen atom, n is as defined above and is advantageously 1, n' is as defined above and is advantageously 1, R' is a hydrogen atom, a halogen atom or a (C$_1$-C$_3$) fluoroalkyl group, or one of its pharmaceutically acceptable salt, can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Ip)

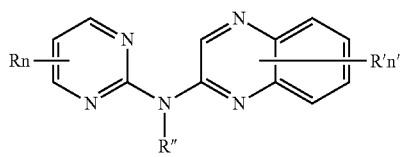

(Ip)

wherein:

R represents a hydrogen atom,

R″ is as defined above and is advantageously a hydrogen atom, n is as defined above and is advantageously 1, n' is as defined above and is advantageously 1, R' is a hydrogen atom, or one of its pharmaceutically acceptable salt, can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Iq)

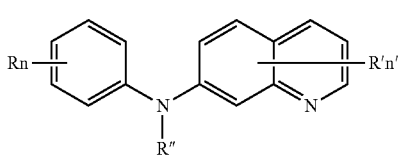

(Iq)

wherein:

R independently represent a hydrogen atom, a (C$_1$-C$_3$) alkoxy group or a (C$_1$-C$_3$)fluoroalkoxy group, R″ is as defined above and is advantageously a hydrogen atom, n is as defined above and is advantageously 1, n' is as defined above and is advantageously 1, R' is a hydrogen atom or a group chosen among a —NR$_1$R$_2$ group, a N-methylpiperazinyl group, a (C$_1$-C$_3$) alkoxy group and a morpholino group, R$_1$ and R$_2$ are independently a hydrogen atom or a (C$_1$-C$_3$)alkyl group, or one of its pharmaceutically acceptable salt, can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Ir)

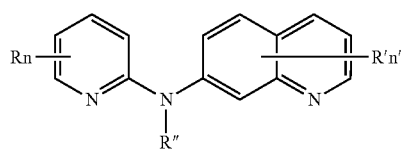

wherein:
R independently represent a hydrogen atom or a ($C_1$-$C_3$) alkyl group,
R" is as defined above and is advantageously a hydrogen atom,
n is as defined above and is advantageously 1,
n' is as defined above and is advantageously 1,
R' is a hydrogen atom or a group chosen among a —$NR_1R_2$ group, a morpholino group and a ($C_1$-$C_3$)alkoxy group,
$R_1$ and $R_2$ are independently a hydrogen atom or a ($C_1$-$C_3$)alkyl group,
or one of its pharmaceutically acceptable salt,
can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

According to another particular embodiment, compound of formula (Iee)

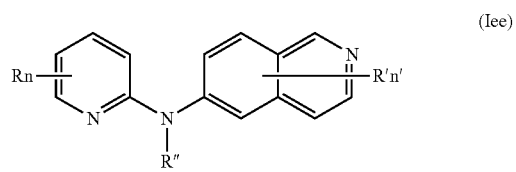

wherein:
R independently represent a hydrogen atom, a ($C_1$-$C_3$) alkyl group or a ($C_1$-$C_3$)fluoroalkyl group,
R" is as defined above and is advantageously a hydrogen atom,
n is as defined above and is advantageously 1,
n' is as defined above and is advantageously 2,
R' is a hydrogen atom or a ($C_1$-$C_3$)alkyl group,
or one of its pharmaceutically acceptable salt,
can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS. Among the previous defined families of compounds of formulae (Ia) to (Iee), some are more particularly preferred for their use as an agent for preventing or treating the infection of a cell and/or an individual, preferably a human, by a retrovirus and/or for preventing, inhibiting or treating a disease caused by retroviruses. These preferred compounds particularly belong to formulae (Ia), (Ib), (Ic), (Ie) and (Io), as defined above or one of its pharmaceutically acceptable salts.

Accordingly compounds of formula (Ia), (Ib), (Ic), (Ie) and (Io), as defined above, can be used as an agent for preventing or treating the infection of an individual, preferably a human, by a retrovirus and/or for preventing, inhibiting or treating a disease caused by retroviruses.

Thus, according to a more particular embodiment, compound of formula (Ia)
wherein:
R independently represent a hydrogen atom, a halogen atom or a group chosen among a ($C_1$-$C_3$)alkyl group, a ($C_1$-$C_3$)fluoroalkyl group, a hydroxyl group, a —CN group, a-COOH group and a ($C_1$-$C_3$)alkoxy group,
R" is as defined above and more preferably is a hydrogen atom,
n is as defined above and more preferably is 1,
n' is as defined above,
R' is a hydrogen atom, a halogen atom, a —$NO_2$ group or a ($C_1$-$C_3$)alkyl group,
or one of its pharmaceutically acceptable salt can be used for the methods described herein. Still according to this more particular embodiment, compounds of formula (Ia'),

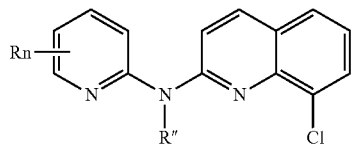

(Ia')

wherein,
R independently represent a hydrogen atom, a —CN group, a ($C_1$-$C_3$)alkyl group, a ($C_1$-$C_3$)fluoroalkyl group, a halogen atom or a hydroxyl group,
R' is as defined in formula (Ia) and is preferably a halogen, a ($C_1$-$C_3$)alkyl group or a $NO_2$ group,
R" is a hydrogen atom,
n is 1 or 2
or one of its pharmaceutically acceptable salt can be used for the methods described herein. According to another more particular embodiment, a compound of formula (Ib)
wherein:
R independently represent a hydrogen atom, a halogen atom, a group chosen among a ($C_1$-$C_4$)alkyl group, a —$NR_1R_2$ group, a ($C_1$-$C_3$)alkoxy group and a ($C_1$-$C_3$)fluoroalkoxy group,
$R_1$ and $R_2$ are independently a hydrogen atom or a ($C_1$-$C_3$)alkyl group,
R" is as defined above and more preferably is a hydrogen atom,
n is as defined above,
n' is as defined above,
R' is a hydrogen atom, halogen atom or a ($C_1$-$C_3$)alkyl group,
or one of its pharmaceutically acceptable salt can be used for the methods described herein.

Still according to this more particular embodiment, compounds of formula (Ib'),

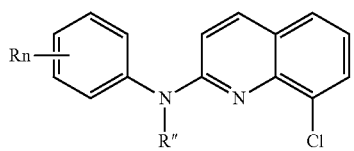

(Ib')

wherein:
R independently represent a hydrogen atom, a halogen atom, a group chosen among a ($C_1$-$C_3$)alkoxy group, a ($C_1$-$C_3$)fluoroalkoxy group,
R" is as defined above and more preferably is a hydrogen atom,
n is as defined above and more preferably is 1,
or one of its pharmaceutically acceptable salt can be used for the methods described herein. According to another more particular embodiment, a compound of formula (Ic)
wherein:
R independently represent a hydrogen atom or a group chosen among a ($C_1$-$C_3$)fluoroalkyl group, a —$NO_2$ group, a —$NR_1R_2$ group and a ($C_1$-$C_3$)alkoxy group,
$R_1$ and $R_2$ are independently a hydrogen atom or a ($C_1$-$C_3$)alkyl group,
R" is as defined above and more preferably is a hydrogen atom,
n is as defined above and more preferably is 1,
n' is as defined above,
R' is a hydrogen atom,
or one of its pharmaceutically acceptable salt can be used for the methods described herein. According to another more particular embodiment, the present disclosure particularly focuses on a compound of formula (Ie)
wherein:
R represents a hydrogen atom,
R" is as defined above and more preferably is a hydrogen atom,
n is as defined above and more preferably is 1,
n' is as defined above,
R' is a hydrogen atom or a halogen atom,
or one of its pharmaceutically acceptable salt,
for use as an agent for preventing, inhibiting or treating retroviral infection.

According to another more particular embodiment, the present disclosure particularly focuses on a compound of formula (Io)
wherein:
R independently represent a hydrogen atom, a halogen atom or a group chosen among a ($C_1$-$C_3$)alkyl group and a —$NO_2$ group,
R" is as defined above and more preferably is a hydrogen atom,
n is 1, 2 or 3,
n' is as defined above,
R' is a hydrogen atom or a ($C_1$-$C_3$)fluoroalkyl group,
or one of its pharmaceutically acceptable salt. In a particular embodiment, the present disclosure relates to a compound of formula (Ia), (Ic) or (Io) as defined above or one of its pharmaceutically acceptable salts, for use as an agent for preventing or treating the infection of a cell and/or an individual, preferably a human, by a retrovirus and/or for preventing, inhibiting or treating a disease caused by retroviruses.

According to a preferred embodiment, the compound for use as an agent for preventing, inhibiting or treating the retroviruses described herein is chosen from:
(1) (8-Chloro-quinolin-2-yl)-pyridin-2-yl-amine
(2) 2-(Quinolin-2-ylamino)-isonicotinic acid
(3) (4-Methyl-pyridin-2-yl)-quinolin-2-yl-amine
(4) Pyridin-2-yl-quinolin-2-yl-amine
(5) 2-(8-Chloro-quinolin-2-ylamino)-isonicotinic acid
(6) (8-Chloro-quinolin-2-yl)-(4-methyl-pyridin-2-yl)-amine
(7) 6-(Quinolin-2-ylamino)-nicotinonitrile
(8) Quinolin-2-yl-(4-trifluoromethoxy-phenyl)-amine
(9) Pyridin-2-yl-quinolin-3-yl-amine
(10) (3-Methoxy-pyridin-2-yl)-quinolin-3-yl-amine

(11) Quinolin-3-yl-(5-trifluoromethyl-pyridin-2-yl)-amine
(12) (5-Nitro-pyridin-2-yl)-quinolin-3-yl-amine
(13) (5-Methyl-pyridin-2-yl)-quinolin-3-yl-amine
(14) 2-(Quinolin-3-ylamino)-isonicotinic acid
(15) Quinolin-6-yl-(5-trifluoromethyl-pyridin-2-yl)-amine
(16) (6-Methyl-pyridin-2-yl)-quinolin-6-yl-amine
(17) N-(6-methylpyridin-2-yl)quinolin-2-amine
(18) 8-chloro-N-(6-methylpyridin-2-yl)quinolin-2-amine
(19) 4-methyl-N-(pyridin-2-yl)quinolin-2-amine
(20) 4-methyl-N-(4-methylpyridin-2-yl)quinolin-2-amine
(21) 3-methyl-N-(4-methylpyridin-2-yl)quinolin-2-amine
(22) 3-methyl-N-(pyridin-2-yl)quinolin-2-amine
(23) 6-((4-methylquinolin-2-yl)amino)nicotinonitrile
(24) 6-((3-methylquinolin-2-yl)amino)nicotinonitrile
(25) 6-chloro-N-(4-methylpyridin-2-yl)quinolin-2-amine
(26) 6-chloro-N-(6-methylpyridin-2-yl)quinolin-2-amine
(27) 4-methyl-N-(5-nitropyridin-2-yl)quinolin-2-amine
(28) N-(3-nitropyridin-2-yl)quinolin-2-amine
(29) 8-chloro-N-(3-nitropyridin-2-yl)quinolin-2-amine
(30) 2-((4-methylquinolin-2-yl)amino)nicotinonitrile
(31) N-(3-methylpyridin-2-yl)quinolin-2-amine
(32) N-(5-methylpyridin-2-yl)quinolin-2-amine
(33) 2-(quinolin-2-ylamino)isonicotinonitrile
(34) N-(5-(trifluoromethyl)pyridin-2-yl)quinolin-2-amine
(35) 8-chloro-N-(3-methylpyridin-2-yl)quinolin-2-amine
(36) 8-chloro-N-(5-methylpyridin-2-yl)quinolin-2-amine
(37) 8-chloro-N-(5-(trifluoromethyl)pyridin-2-yl)quinolin-2-amine
(38) N-(3-methoxypyridin-2-yl)quinolin-2-amine
(39) N-(5-nitropyridin-2-yl)quinolin-2-amine
(40) 6-((8-chloroquinolin-2-yl)amino)nicotinonitrile
(41) N-(5-fluoropyridin-2-yl)quinolin-2-amine
(42) N-(6-(trifluoromethyl)pyridin-2-yl)quinolin-2-amine
(43) 8-chloro-N-(5-fluoropyridin-2-yl)quinolin-2-amine
(44) 2-((8-chloroquinolin-2-yl)amino)nicotinic acid
(45) 4-methyl-N-(6-methylpyridin-2-yl)quinolin-2-amine
(46) 3-methyl-N-(6-methylpyridin-2-yl)quinolin-2-amine
(47) 5-cyano-2-(quinolin-2-ylamino)pyridin-1-ium chloride
(48) 2-((8-chloroquinolin-2-yl)amino)-4-methylpyridin-1-ium chloride
(49) 8-chloro-N-(4-ethylpyridin-2-yl)quinolin-2-amine
(50) 8-chloro-N-(6-ethylpyridin-2-yl)quinolin-2-amine
(51) 8-chloro-N-(4,6-dimethylpyridin-2-yl)quinolin-2-amine
(52) 6-((8-chloroquinolin-2-yl)amino)-2-methylnicotinonitrile
(53) 8-chloro-N-(4-chloropyridin-2-yl)quinolin-2-amine
(54) 8-methyl-N-(4-methylpyridin-2-yl)quinolin-2-amine
(55) N-(5-bromo-4-methylpyridin-2-yl)-8-chloroquinolin-2-amine
(56) 8-chloro-N-(3-ethyl-6-methylpyridin-2-yl)quinolin-2-amine
(57) 8-fluoro-N-(4-methylpyridin-2-yl)quinolin-2-amine
(58) 8-bromo-N-(4-methylpyridin-2-yl)quinolin-2-amine
(59) methyl 6-(quinolin-2-ylamino)nicotinate
(60) methyl 6-[(8-chloroquinolin-2-yl)amino]pyridine-3-carboxylate
(61) methyl 6-[(3-methylquinolin-2-yl)amino]pyridine-3-carboxylate
(62) methyl 2-[(8-chloroquinolin-2-yl)amino]pyridine-3-carboxylate
(63) 8-methoxy-N-(4-methylpyridin-2-yl)quinolin-2-amine
(64) N-(4-methylpyridin-2-yl)-5-nitroquinolin-2-amine
(65) 2-N-(4-methylpyridin-2-yl)quinoline-2,8-diamine
(66) N-(4-methylpyridin-2-yl)-5-aminoquinolin-2-amine
(67) methyl 6-[(4-methylquinolin-2-yl)amino]pyridine-3-carboxylate
(68) 8-chloro-N-[4-(trifluoromethyl)pyridin-2-yl]quinolin-2-amine
(69) 2-[(8-chloroquinolin-2-yl)amino]pyridin-3-ol
(70) 8-chloro-N-[6-(trifluoromethyl)pyridin-2-yl]quinolin-2-amine
(71) 6-chloro-N-(5-fluoropyridin-2-yl)quinolin-2-amine
(72) N-(6-ethylpyridin-2-yl)-3-methylquinolin-2-amine
(73) N-(5-fluoropyridin-2-yl)-3-methylquinolin-2-amine
(74) 3-methyl-N-[5-(trifluoromethyl)pyridin-2-yl]quinolin-2-amine
(75) 4-N-(8-chloroquinolin-2-yl)-1-N,1-N-dimethylbenzene-1,4-diamine
(76) N-(4-methoxyphenyl)quinolin-2-amine
(77) 8-chloro-N-(4-methoxyphenyl)quinolin-2-amine
(78) 4-methyl-N-[4-(trifluoromethoxy)phenyl]quinolin-2-amine
(79) N-(4-methoxyphenyl)-3-methylquinolin-2-amine
(80) 3-methyl-N-[4-(trifluoromethoxy)phenyl]quinolin-2-amine
(81) 1-N,1-N-dimethyl-4-N-(3-methylquinolin-2-yl)benzene-1,4-diamine
(82) N-[2-methyl-4-(trifluoromethoxy)phenyl]quinolin-2-amine
(83) N-[3-(trifluoromethoxy)phenyl]quinolin-2-amine
(84) N-[2-(trifluoromethoxy)phenyl]quinolin-2-amine
(85) N-(4-nitrophenyl)quinolin-2-amine
(86) N-(3-fluorophenyl)quinolin-2-amine
(87) 8-chloro-N-[3-(trifluoromethoxy)phenyl]quinolin-2-amine
(88) 8-chloro-N-(3-fluorophenyl)quinolin-2-amine
(89) 2-{[4-(trifluoromethoxy)phenyl]amino}quinolin-1-ium chloride
(90) 8-chloro-N-[4-(trifluoromethoxy)phenyl]quinolin-2-amine
(91) 3-methyl-N-[2-methyl-4-(trifluoromethoxy)phenyl]quinolin-2-amine
(92) 3-methyl-N-[3-(trifluoromethoxy)phenyl]quinolin-2-amine
(93) 3-methyl-N-[2-(trifluoromethoxy)phenyl]quinolin-2-amine
(94) 8-chloro-N-[2-methyl-4-(trifluoromethoxy)phenyl]quinolin-2-amine
(95) 3-methyl-2-{[4-(trifluoromethoxy)phenyl]amino}quinolin-1-ium chloride
(96) 6-chloro-N-(4-(trifluoromethoxy)phenyl)quinolin-2-amine
(97) 4-methyl-2-{[4-(trifluoromethoxy)phenyl]amino}quinolin-1-ium chloride
(98) 8-bromo-N-[4-(trifluoromethoxy)phenyl]quinolin-2-amine
(99) 8-fluoro-N-[4-(trifluoromethoxy)phenyl]quinolin-2-amine
(100) 8-methyl-N-[4-(trifluoromethoxy)phenyl]quinolin-2-amine
(101) N-(4-butoxyphenyl)-8-chloroquinolin-2-amine
(102) N-(4-phenoxyphenyl)quinolin-2-amine
(103) 8-methoxy-N-[4-(trifluoromethoxy)phenyl]quinolin-2-amine
(104) 8-chloro-N-[3-chloro-4-(trifluoromethoxy)phenyl]quinolin-2-amine
(105) N-(6-methylpyridin-2-yl)quinolin-3-amine
(106) N-(3-nitropyridin-2-yl)quinolin-3-amine
(107) N-(5-methylpyridin-2-yl)quinolin-6-amine
(108) N-(3-methoxypyridin-2-yl)quinolin-6-amine
(109) 6-chloro-N-(pyrazin-2-yl)quinolin-2-amine
(110) 8-bromo-N-(pyrazin-2-yl)quinolin-2-amine
(111) 8-methyl-N-(pyrazin-2-yl)quinolin-2-amine (112) 8-chloro-N-(pyrazin-2-yl)quinolin-2-amine
(113) N-(pyrazin-2-yl)quinolin-2-amine
(114) 4-methyl-N-(pyrazin-2-yl)quinolin-2-amine
(115) 3-methyl-N-(pyrazin-2-yl)quinolin-2-amine
(116) 8-fluoro-N-(pyrazin-2-yl)quinolin-2-amine
(117) 8-methoxy-N-(pyrazin-2-yl)quinolin-2-amine
(118) N-(pyridin-3-yl)quinolin-3-amine
(119) 8-chloro-N-(pyridin-4-yl)quinolin-2-amine
(120) N-(pyridin-4-yl)quinolin-2-amine
(121) N-(pyridin-4-yl)quinolin-3-amine
(122) N-[4-(trifluoromethoxy)phenyl]quinolin-3-amine
(123) N-(4-methoxyphenyl)quinolin-3-amine
(124) N-[4-(trifluoromethoxy)phenyl]quinoxalin-2-amine
(125) N-[2-methyl-4-(trifluoromethoxy)phenyl]quinoxalin-2-amine
(126) N-[3-(trifluoromethoxy)phenyl]quinoxalin-2-amine
(127) N-[2-(trifluoromethoxy)phenyl]quinoxalin-2-amine
(128) N-(pyrimidin-2-yl)quinolin-2-amine
(129) 8-chloro-N-(pyrimidin-2-yl)quinolin-2-amine
(130) 4-methyl-N-(pyrimidin-2-yl)quinolin-2-amine
(131) N-(pyrazin-2-yl)quinolin-6-amine
(132) N-(pyrazin-2-yl)quinolin-3-amine
(133) 6-methyl-N-(naphthalen-2-yl)pyridin-2-amine
(134) N-(naphthalen-2-yl)pyridin-2-amine
(135) N-(pyridin-2-yl)quinoxalin-2-amine
(136) N-(4-methylpyridin-2-yl)quinoxalin-2-amine
(137) 6-(quinoxalin-2-ylamino)pyridine-3-carbonitrile
(138) N-(6-methylpyridin-2-yl)quinoxalin-2-amine
(139) N-(4-methylpyridin-2-yl)-3-(trifluoromethyl)quinoxalin-2-amine
(140) N-(3,5-dichloro-4-methylpyridin-2-yl)quinoxalin-2-amine
(141) N-(4-methyl-3-nitropyridin-2-yl)quinoxalin-2-amine
(142) N-(pyrimidin-2-yl)quinoxalin-2-amine
(143) 4-N,4-N-dimethyl-7-N-[4-(trifluoromethoxy)phenyl]quinoline-4,7-diamine
(144) 4-(morpholin-4-yl)-N-[4-(trifluoromethoxy)phenyl]quinolin-7-amine
(145) 4-methoxy-N-(pyridin-2-yl)quinolin-7-amine
(146) 4-methoxy-N-(4-methylpyridin-2-yl)quinolin-7-amine
(147) 4-N,4-N-dimethyl-7-N-(4-methylpyridin-2-yl)quinoline-4,7-diamine
(148) 5,8-dimethyl-N-(5-methylpyridin-2-yl)isoquinolin-6-amine
(149) 5,8-dimethyl-N-(5-trifluoromethylpyridin-2-yl)isoquinolin-6-amine
(150) N-(4-methylpyridin-2-yl)-8-nitroquinolin-2-amine
(151) 6-chloro-N-(6-ethylpyridin-2-yl)quinolin-2-amine
(152) 6-chloro-N-(5-methylpyridin-2-yl)quinolin-2-amine
(153) 6-chloro-N-[5-(trifluoromethyl)pyridin-2-yl]quinolin-2-amine
(154) N2-(8-chloroquinolin-2-yl)-4-methylpyridine-2,3-diamine
(155) N-(4-butoxyphenyl)-3-methylquinolin-2-amine
(156) 4-N-(6-chloroquinolin-2-yl)-1-N,1-N-dimethylbenzene-1,4-diamine
(157) 8-chloro-N-(3-chloro-4-methoxyphenyl)quinolin-2-amine
(158) N1-(8-chloroquinolin-2-yl)-4-(trifluoromethoxy)benzene-1,2-diamine
(159) N-(3-aminopyridin-2-yl)quinolin-3-amine
(160) 6-chloro-N-(4-methylpyridin-2-yl)quinoxalin-2-amine
(161) N-(4-ethylpyridin-2-yl)quinoxalin-2-amine
(162) N-(5-bromo-4-methylpyridin-2-yl)quinoxalin-2-amine
(163) N-(4,6-dimethylpyridin-2-yl)quinoxalin-2-amine
(164) [2-(quinoxalin-2-ylamino)pyridin-4-yl]methanol
(165) N-(4-methyl-5-nitropyridin-2-yl)quinoxalin-2-amine
(166) N-(4-methoxyphenyl)-4-(4-methylpiperazin-1-yl)quinolin-7-amine
(167) 4-methoxy-N-[4-(trifluoromethoxy)phenyl]quinolin-7-amine
(168) N-(4-methylpyridin-2-yl)-4-(morpholin-4-yl)quinolin-7-amine and their pharmaceutically acceptable salts.

Among said compounds, compounds (1), (6), (33), (34), (35), (36), (37), (38), (42), (43), (44), (45), (46), (48), (50), (64), (68), (69), (70), (71), (72), (73), (74), (75), (77), (78), (79), (80), (81), (82), (86), (87), (88), (90), (92), (96), (104), (106), (109), (112), (136), (139), (140) and (141) are of particular interest.

As described herein, compounds (1), (6), (33), (34), (35), (36), (37), (38), (42), (43), (44), (45), (46), (48), (50), (64), (68), (69), (70), (71), (72), (73), (74), (75), (77), (78), (79), (80), (81), (82), (86), (87), (88), (90), (92), (96), (104), (106), (109), (112), (136), (139), (140) and (141) or one of its pharmaceutically acceptable salts can be used for for preventing or treating the infection of a cell and/or an individual, preferably a human, in need thereof by a retrovirus and/or for preventing retrovirus and/or for preventing, inhibiting or treating a disease caused by retroviruses, wherein the retroviruses include visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, bovine leukemia virus or BLV, primate type D oncoviruses, type B oncoviruses, Rous sarcoma virus or RSV, simian foamy virus or SFV or chimpanzee simian virus, human foamy virus, and feline immunodeficiency virus, the human foamy virus or HFV, bovine syncytial virus or BSV, feline syncytial virus FSV, the feline immunodeficiency virus, avian leukosis virus, Walleye dermal sarcoma virus, T-cell lymphoma, acute ATL, lymphomatous ATL, chronic ATL, smoldering ATL, neurologic diseases, Tropical spastic paraparesis or HTLV-associated myelopathy, inflammatory and autoimmune diseases such as uveitis, dermatitis, pneumonitis, rheumatoid arthritis, and polymyositis hematologic and dermatologic diseases, lung diseases, brain diseases, and/or immunodeficiency and the retrovirus does not include HIV and the disease caused by the retroviral infection is not AIDS.

The compounds of formulae (I), (Ia), (Ib), (Ic), (Id), (Ie), (If), (Ig), (Ih), (Ii), (Ij), (Ik), (Il), (Im), (Io), (Ip), (Iq), (Ir) and (Iee) can comprise one or more asymmetric carbon atoms. They can thus exist in the form of enantiomers or of diastereoisomers. These enantiomers, diastereoisomers and their mixtures, including the racemic mixtures, are encompassed within the scope of the present disclosure.

According to a particular embodiment, the present disclosure encompasses compounds of formula (Ig)
wherein:
R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group, and a $(C_1-C_3)$alkoxy group, n is 1 or 2, n' is 1 or 2, R' is a hydrogen atom or a group chosen among a $(C_1\text{-}C_3)$alkyl group, a halogen atom, a hydroxyl group, a —$COOR_1$ group, a —$NO_2$ group, a —$NR_1R_2$ group, a $(C_1\text{-}C_3)$alkoxy group and a —CN group, R" is a hydrogen atom or a $(C_1\text{-}C_4)$alkyl group, $R_1$ and $R_2$ are independently a hydrogen atom or a $(C_1\text{-}C_3)$alkyl group, with the proviso that R and R' are not simultaneously a hydrogen atom, and when n and n' are 1 and R is a hydrogen atom then R' is not a —COOH group, or anyone of its pharmaceutically acceptable salt.

According to another particular embodiment, the present disclosure encompasses compounds of formula (If) wherein:

R independently represent a hydrogen atom, a halogen atom or a group chosen among a $(C_1\text{-}C_3)$alkyl group, a —CN group, a hydroxyl group, a —$COOR_1$ group, a $(C_1\text{-}C_3)$fluoroalkyl group, a $(C_1\text{-}C_3)$fluoroalkoxy group, a —$NO_2$ group, a —$NR_1R_2$ group, and a $(C_1\text{-}C_3)$alkoxy group, n is 1 or 2, n' is 1 or 2, R' is a hydrogen atom or a group chosen among a $(C_1\text{-}C_3)$alkyl group, a halogen atom, a hydroxyl group, a —$COOR_1$ group, a —$NO_2$ group, a —$NR_1R_2$ group, a $(C_1\text{-}C_3)$alkoxy group and a —CN group, R" is a hydrogen atom or a $(C_1\text{-}C_4)$alkyl group, $R_1$ and $R_2$ are independently a hydrogen atom or a $(C_1\text{-}C_3)$alkyl group, or anyone of its pharmaceutically acceptable salt.

According to another particular embodiment, the present disclosure encompasses compounds of formula (Ih) wherein:

R independently represent a hydrogen atom, a halogen atom or a group chosen among a $(C_1\text{-}C_3)$alkyl group, a —CN group, a hydroxyl group, a —$COOR_1$ group, a $(C_1\text{-}C_3)$fluoroalkyl group, a $(C_1\text{-}C_3)$fluoroalkoxy group, a —$NO_2$ group, a —$NR_1R_2$ group, and a $(C_1\text{-}C_3)$alkoxy group, n is 1 or 2, n' is 1 or 2, R' is a hydrogen atom or a group chosen among a $(C_1\text{-}C_3)$alkyl group, a halogen atom, a hydroxyl group, a —$COOR_1$ group, a —$NO_2$ group, a —$NR_1R_2$ group, a $(C_1\text{-}C_3)$alkoxy group and a —CN group, R" is a hydrogen atom or a $(C_1\text{-}C_4)$alkyl group, $R_1$ and $R_2$ are independently a hydrogen atom or a $(C_1\text{-}C_3)$alkyl group, or anyone of its pharmaceutically acceptable salt.

According to another particular embodiment, the present disclosure encompasses compounds of formula (Il) wherein:

R independently represent a hydrogen atom, a halogen atom or a group chosen among a $(C_1\text{-}C_3)$alkyl group, a —CN group, a hydroxyl group, a —$COOR_1$ group, a $(C_1\text{-}C_3)$fluoroalkyl group, a $(C_1\text{-}C_3)$fluoroalkoxy group, a —$NO_2$ group, a —$NR_1R_2$ group, and a $(C_1\text{-}C_3)$alkoxy group, n is 1 or 2, n' is 1 or 2, R' is a hydrogen atom or a group chosen among a $(C_1\text{-}C_3)$alkyl group, a halogen atom, a hydroxyl group, a —$COOR_1$ group, a —$NO_2$ group, a —$NR_1R_2$ group, a $(C_1\text{-}C_3)$alkoxy group and a —CN group, R" is a hydrogen atom or a $(C_1\text{-}C_4)$alkyl group, $R_1$ and $R_2$ are independently a hydrogen atom or a $(C_1\text{-}C_3)$alkyl group, with the proviso that R and R' are not simultaneously a hydrogen atom, or anyone of its pharmaceutically acceptable salt.

According to another particular embodiment, the present disclosure encompasses compounds of formula (Im) wherein:

R independently represent a hydrogen atom, a halogen atom or a group chosen among a $(C_1\text{-}C_3)$alkyl group, a —CN group, a hydroxyl group, a —$COOR_1$ group, a $(C_1\text{-}C_3)$fluoroalkyl group, a $(C_1\text{-}C_3)$fluoroalkoxy group, a —$NO_2$ group, a —$NR_1R_2$ group, and a $(C_1\text{-}C_3)$alkoxy group, n is 1 or 2, n' is 1 or 2, R' is a hydrogen atom or a group chosen among a $(C_1\text{-}C_3)$alkyl group, a halogen atom, a hydroxyl group, a —$COOR_1$ group, a —$NO_2$ group, a —$NR_1R_2$ group, a $(C_1\text{-}C_3)$alkoxy group and a —CN group, R" is a hydrogen atom or a $(C_1\text{-}C_4)$alkyl group, $R_1$ and $R_2$ are independently a hydrogen atom or a $(C_1\text{-}C_3)$alkyl group, with the proviso that when n and n' are 1 and R is a hydrogen atom, R' is not a chlorine atom, or anyone of its pharmaceutically acceptable salt.

According to another particular embodiment, the present disclosure encompasses compounds of formula (Ia), as such, wherein:

R" and n are as defined in formula (Ia), n' is 1,

R independently represent a hydrogen atom, a halogen atom or a group chosen among a $(C_1\text{-}C_3)$alkyl group, a —CN group, a hydroxyl group, a —$COOR_1$ group, a $(C_1\text{-}C_3)$fluoroalkyl group, a —$NO_2$ group, a $(C_1\text{-}C_3)$fluoroalkoxy group and a $(C_1\text{-}C_3)$alkoxy group, R' is a hydrogen atom or a halogen atom or a group chosen among a $(C_1\text{-}C_3)$alkyl group, a —$COOR_1$ group, and a —CN group, and wherein:

with the proviso that when R and R' are not simultaneously a hydrogen atom, when n is 1, R is not a methyl group in ortho or para position with respect to Z, Z being N, when R' is a hydrogen atom, R is not a bromine atom or a chlorine atom, when R is a hydrogen atom, R' is not a methyl or ethyl group, a —COOH group, a $COOC_2H_5$ group or a bromine atom, said bromine atom being in ortho position of the bond linked to NR", or one of its pharmaceutically acceptable salt.

Still according to this particular embodiment, the present disclosure more particularly focuses on compounds of formula (Ia), as such, wherein, R independently represent a hydrogen atom, a $(C_1\text{-}C_3)$ fluoroalkyl group, a halogen atom, a —CN group or a $(C_1\text{-}C_3)$alkyl group, R" is as defined in formula (Ia), R' is a hydrogen atom, a halogen atom or a —$NO_2$ group, n' is 1, n is 1, with the proviso that when n is 1, R is not a methyl group in ortho or para position with respect to Z, Z being N, R is not a bromine atom or a chlorine atom when R' is a hydrogen atom, or one of its pharmaceutically acceptable salt.

Still according to this particular embodiment, the present disclosure more preferably focuses on compounds of formula (Ia'), as such,

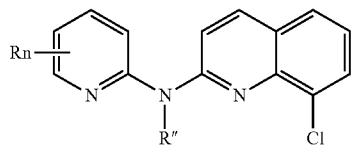

(Ia')

wherein,
R independently represent a hydrogen atom, a $(C_1-C_3)$ alkyl group, a $(C_1-C_3)$fluoroalkyl group, a halogen atom or a hydroxyl group,
R" is as defined in formula (Ia),
n is 1 or 2, and preferably 1,
or one of its pharmaceutically acceptable salt.

The present disclosure further relates to a compound of formula (Ib) as defined above, as such

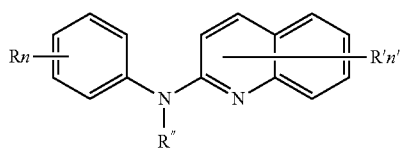

(Ib)

wherein:
R' and R" are as defined in formula (Ib),
n is 1, and
R is a hydrogen atom or a $(C_1-C_3)$fluoroalkoxy group,
or one of its pharmaceutically acceptable salt.

Still according to this particular embodiment, the present disclosure more particularly focuses on compounds of formula (Ib)
wherein:
R is a hydrogen atom or a $(C_1-C_3)$fluoroalkoxy group,
R' is a hydrogen atom, a halogen atom or a $(C_1-C_4)$alkyl group,
R" is as defined in the formula (Ib),
n' is 1 or 2 and is preferably 1,
n is 1 or 2 and is preferably 1,
or one of its pharmaceutically acceptable salt.

Still according to this particular embodiment, the present disclosure more particularly focuses on compounds of formula (Ib')

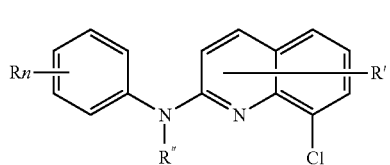

(Ib')

wherein:
R, R" and n are as defined in formula (Ib),
R' is as defined in formula (Ib),
with the proviso that R' is different from a methyl group in position 4 on the quinoline,
or one of its pharmaceutically acceptable salt.

Still according to this particular embodiment, the present disclosure more particularly focuses on compounds of formula (Ib")

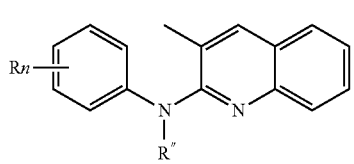

(Ib")

wherein:
R, R" and n are as defined in formula (Ib),
with the proviso that when n is 1, R is not a hydrogen atom, a methyl group in para of the bond linked to NR", a ethoxy group in para of the bond linked to NR", nor a fluorine atom in para of the bond linked to NR",
or one of its pharmaceutically acceptable salt.

According to another particular embodiment, the present disclosure encompasses compounds of formula (Ic), as such,
wherein:
R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a —NO$_2$ group, a —NR$_1$R$_2$ group and a $(C_1-C_3)$alkoxy group,
R$_1$ and R$_2$ are independently a hydrogen atom or a $(C_1-C_3)$alkyl group,
n is 1 or 2, and advantageously 1,
n' is 1 or 2,
R" is as defined in formula (Ic),
R' is a hydrogen atom or a group chosen among a $(C_1-C_3)$alkyl group, a —NO$_2$ group, a —NR$_1$R$_2$ group and a $(C_1-C_3)$alkoxy group,
with the proviso that
R and R' are not simultaneously a hydrogen atom,
R is not a bromine atom when R' is a hydrogen atom,
or one of its pharmaceutically acceptable salt.

Still according to this particular embodiment, the present disclosure more particularly focuses on compounds of formula (Ic), as such, wherein,
R is a hydrogen atom or a —NO$_2$ group,
n is 1,
R', R" and n' are as defined in formula (Ic), and
R' is preferably a $(C_1-C_3)$alkyl group or a hydrogen atom,
or one of its pharmaceutically acceptable salt.

The present disclosure further relates to a compound of formula (Ie) as defined above, as such

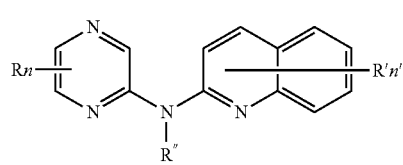

(Ie)

wherein:
R, R', R" n and n' are as defined in formula (I),
with the proviso that
when R is a hydrogen atom, R' is not a bromine atom,
or one of its pharmaceutically acceptable salt.

According to another particular embodiment, the present disclosure encompasses compounds of formula (Io), as such, wherein:

R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group and a $(C_1-C_3)$alkoxy group, R$_1$ and R$_2$ are independently a hydrogen atom or a $(C_1-C_3)$alkyl group, n is 1, 2 or 3, n' is 1 or 2, R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group, R" is a hydrogen atom or a $(C_1-C_4)$alkyl group, with the proviso that when R is a hydrogen atom and n' is 1, R' is not a hydroxyl group, or one of its pharmaceutically acceptable salt.

Still according to this particular embodiment, the present disclosure more particularly focuses on compounds of formula (Io'), as such, wherein

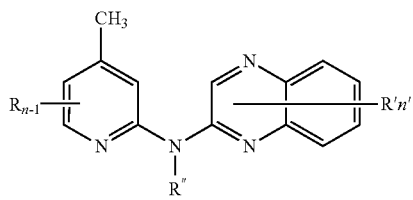

(Io')

wherein:

n is 1, 2 or 3, n' is 1 or 2,

R independently represent a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a $(C_1-C_3)$fluoroalkoxy group, a —NO$_2$ group, a —NR$_1$R$_2$ group and a $(C_1-C_3)$alkoxy group, and is preferably a —NO$_2$ group, a hydrogen atom or a halogen atom, R' is a hydrogen atom or a group chosen among a $(C_1-C_3)$alkyl group, a halogen atom, a hydroxyl group, a —COOR$_1$ group, a —NO$_2$ group, a —NR$_1$R$_2$ group, a $(C_1-C_3)$alkoxy group and a —CN group, a $(C_1-C_3)$fluoralkyl group, and preferably is a hydrogen atom or a $(C_1-C_3)$fluoroalkyl group, R$_1$ and R$_2$ are as defined in formula (Io), R" is a hydrogen atom or a $(C_1-C_4)$alkyl group, or one of its pharmaceutically acceptable salt.

Among said compounds as such, compounds (1), (2), (5)-(8), (10)-(16), (18), (21)-(44), (46)-(75), (77)-(84), (86)-(119), (121), (124)-(130), (132), (135)-(141), (143)-(147), (149)-(168) and their pharmaceutically acceptable salts are of particular interest.

The present disclosure therefore extends to compounds (1), (2), (5)-(8), (10)-(16), (18), (21)-(44), (46)-(75), (77)-(84), (86)-(119), (121), (124)-(130), (132), (135)-(141), (143)-(147), (149)-(168) and their pharmaceutically acceptable salts, as such.

More preferably, compounds (8), (75), (77)-(84), (86)-(104), (109)-(117), (155)-(158) and their pharmaceutically acceptable salts are of particular interest.

The present disclosure therefore extends more preferably to compounds (8), (75), (77)-(84), (86)-(104), (109)-(117), (155)-(158) and their pharmaceutically acceptable salts, such as hydrobromide, tartrate, citrate, trifluoroacetate, ascorbate, hydrochloride, tartrate, triflate, maleate, mesylate, formate, acetate and fumarate.

Still more preferably, the present disclosure extends to compounds (75), (77), (78), (79), (80), (81), (82), (86), (87), (88), (90), (92), (96), (104), (109), (112), and their pharmaceutically acceptable salts, such as hydrobromide, tartrate, citrate, trifluoroacetate, ascorbate, hydrochloride, tartrate, triflate, maleate, mesylate, formate, acetate and fumarate.

The compounds of formulae (Ia), (Ic), (Io), (Ib), (Ib'), (Ib") and (Ie) and the specific compounds as listed above are thus useful for preventing or treating the infection of cell and/or an individual, preferably a human, by a retrovirus and/or for inhibiting, preventing or treating a disease caused by retroviruses, such retroviruses being oncoviruses, lentiviruses and/or spumaviruses.

As described herein, the term oncovirus can include Alpharetrovirus (for example, avian leukosis virus and Rous sarcoma virus); Betaretrovirus (for example, mouse mammary tumor virus); Gammaretrovirus (for example, murine leukemia virus and feline leukemia virus); Deltaretrovirus (for example bovine leukemia virus and human T-lymphotropic virus); and Epsilonretrovirus (for example, Walleye dermal sarcoma virus).

More generally, the retroviruses described herein may be, for example, visna/maedi virus or MVV/visna, equine infectious anemia virus or EIAV, caprine arthritis encephalitis virus or CAEV, simian immunodeficiency virus or SIV, avian leukemia virus or ALV, murine leukemia virus also called Moloney virus or MULV, Abelson leukemia virus, murine mammary tumor virus, Mason-Pfizer monkey virus or MPMV, feline leukemia virus or FELV, human leukemia viruses HTLV-I, human leukemia viruses HTLV-II, simian leukemia virus or STLV, the bovine leukemia virus or BLV, primate type D oncoviruses, type B oncoviruses, Rous sarcoma virus or RSV, and/or simian foamy virus or SFV or chimpanzee simian virus, human foamy virus, and feline immunodeficiency virus, the human foamy virus (or HFV), bovine syncytial virus (or BSV), feline syncytial virus (FSV) and the feline immunodeficiency virus.

More particularly, HTLV-I causes T-cell lymphoma (ATL for Adult T-cell leukemia/lymphoma, including the different forms of ATL such as acute ATL, lymphomatous ATL, chronic ATL and smoldering ATL), neurologic disease, Tropical spastic paraparesis (TSP) (also known as HTLV-associated myelopathy (HAM) or chronic progressive myelopathy), and diverse inflammatory and autoimmune diseases such as uveitis, dermatitis, pneumonitis, rheumatoid arthritis, and polymyositis (Harrison's Infections diseases, Kasper and Fauci, 2010, section V, part 4, chapter 89, Longo and Fauci, 785-792); HTLV-II may play a role in certain neurologic, hematologic and dermatologic diseases (Harrison's Infections diseases, Kasper and Fauci, 2010, section V, part 4, chapter 89, Longo and Fauci, 785-792); HIV (HIV1 and HIV2) causes AIDS; the visna virus causes lung and brain diseases in sheep; the feline immunodeficiency virus causes immunodeficiency in cat; Rous sarcoma virus and mouse mammary tumor virus causes tumor growth and cancer.

In certain aspects, the methods described herein include contacting a cell having a retroviral infection with at least one of the compounds described herein, wherein the retroviral infection does not include HIV. In another aspect, the methods described herein include inhibiting RNA splicing of a retrovirus by administering a compound to a subject in need thereof, wherein the compound includes at least one compound described herein and the retrovirus does not include HIV. In yet another aspect, the methods described herein include methods for treating a retroviral infection or a disease caused by the retroviral infection comprising administering an effective amount of a pharmaceutical composition to a subject in need thereof, wherein the pharmaceutical composition includes at least one compound described herein and the retroviral infection does not include HIV and the disease caused by the retroviral infection does not include AIDS.

The compounds of the present disclosure can be prepared by conventional methods of organic synthesis practiced by those skilled in the art. The general reaction sequences outlined below represent a general method useful for preparing the compounds of the present disclosure and are not meant to be limiting in scope or utility.

The compounds of general formula (I) can be prepared according to scheme 1 below.

Scheme 1

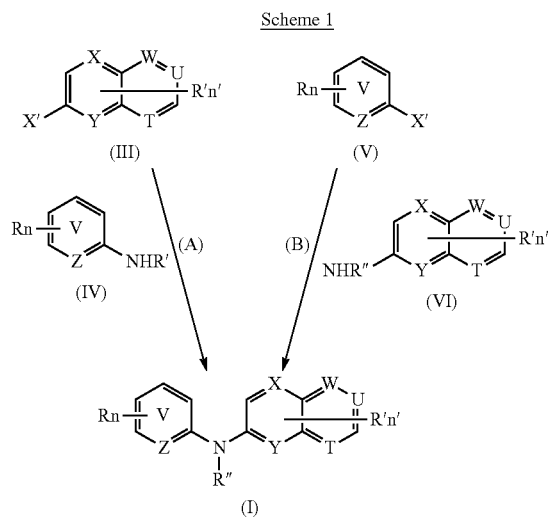

As appears in said scheme two routes are available for recovering a compound of formula (I) according to the present disclosure.

The synthesis is based on a coupling reaction alternatively starting from a halogeno-bicycle of formula (III), wherein X, Y, W, T, U, n', R' and R'' are as defined above and X' is a chlorine atom or a bromine atom or from a chloro-monocycle of formula (V), wherein Z, V, n and R are as defined above and X' is a chlorine atom or a bromine atom.

According to route (A), the compound of formula (III) is placed in a protic solvent such as tert-butanol. The compound of formula (IV) is then added in a molar ratio ranging from 1 to 1.5 with respect to the compound of formula (III) in presence of an inorganic base, such as $Cs_2CO_3$ or $K_2CO_3$ in a molar ratio ranging from 1 and 2, in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) in an amount ranging from 2 mol % to 10 mol % relative to the total amount of compound of formula (III), and in the presence of a catalyst, such as $Pd(OAc)_2$ or $Pd_2dba_3$ in an amount ranging from 2 mol % to 10 mol % relative to the total amount of compound of formula (III). The reaction mixture can then be heated at a temperature ranging from 80 to 120° C., for example at 90° C. and stirred for a time ranging from 15 to 25 hours, for example during 20 hours under inert gas and for example argon. The reaction mixture can be concentrated under reduced pressure.

According to route (B) the compound of formula (V) is placed in a protic solvent such as tert-butanol. The compound of formula (VI) is then added in a molar ratio ranging from 1 to 1.5 with respect to the compound of formula (V) in presence of an inorganic base, such as $Cs_2CO_3$ or $K_2CO_3$ in a molar ratio ranging from 1 to 2, in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) in an amount ranging from 2 mol % to 10 mol % relative to the total amount of compound of formula (V), and in the presence of a catalyst, such as $Pd(OAc)_2$ or $Pd_2dba_3$ in an amount ranging from 2 mol % to 10 mol % relative to the total amount of compound of formula (V). The reaction mixture can then be heated at a temperature ranging from 80 to 120° C., for example at 90° C. and stirred for a time ranging from 15 to 25 hours, for example during 20 hours under inert gas and for example argon. The reaction mixture can be concentrated under reduced pressure.

The starting compounds of formula (III), (IV), (V) and (VI) are commercially available or can be prepared according to methods known to the person skilled in the art.

The chemical structures and spectroscopic data of some compounds of formula (I) of the disclosure are illustrated respectively in the following Table I and Table II.

TABLE I

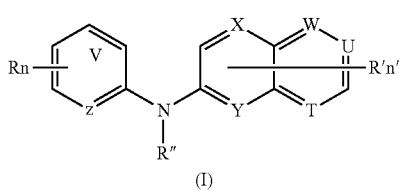

| | Formula (Ia) |
|---|---|
| 1 | 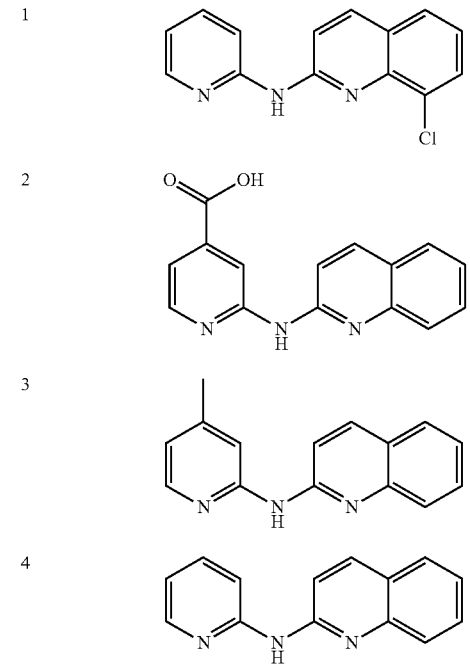 |
| 2 | |
| 3 | |
| 4 | |

TABLE I-continued
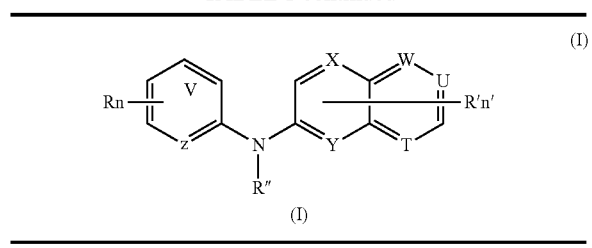
(I)
| 5 | 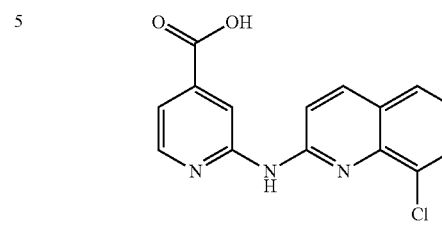 |
| --- | --- |
| 6 | 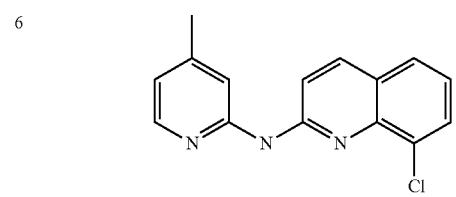 |
| 7 | 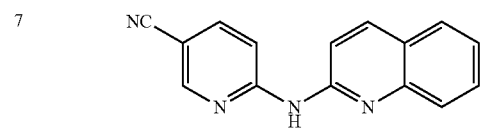 |
| 17 | 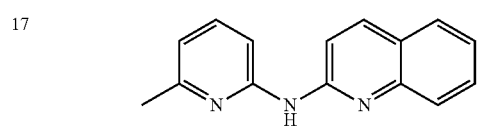 |
| 18 | 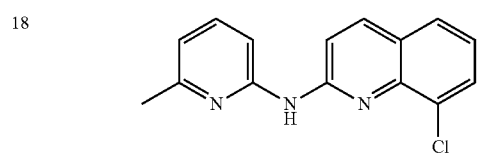 |
| 19 | 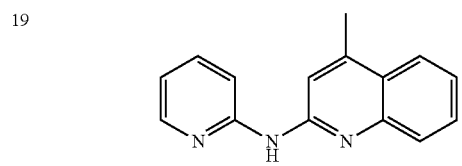 |
| 20 | 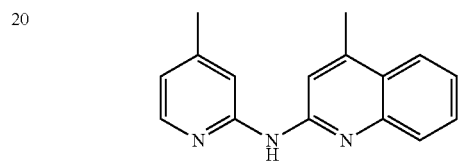 |
| 21 | 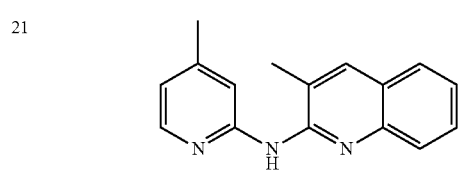 |
TABLE I-continued
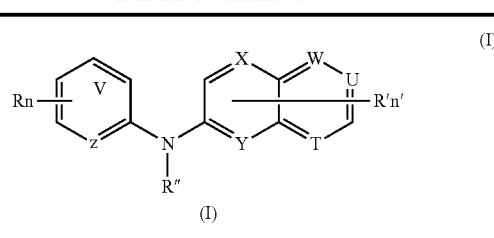
(I)
| 22 | 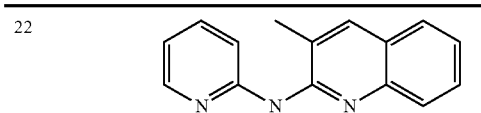 |
| --- | --- |
| 23 | 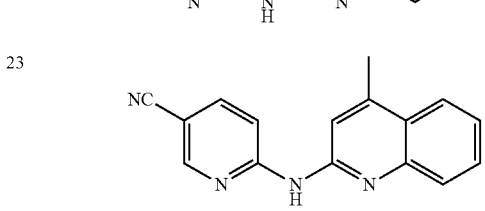 |
| 24 | 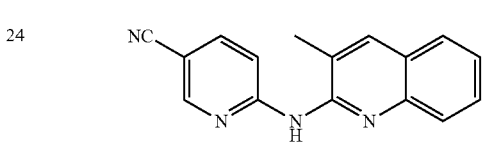 |
| 25 | 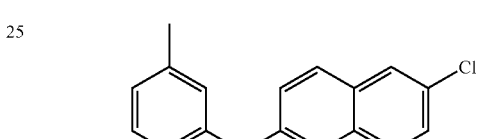 |
| 26 | 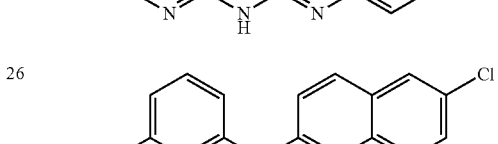 |
| 27 | 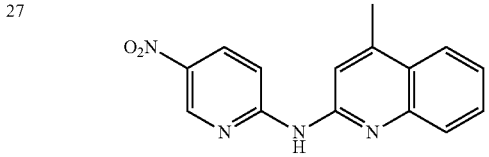 |
| 28 | 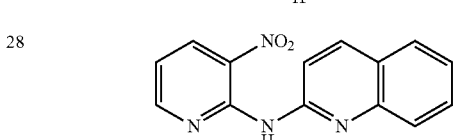 |
| 29 | 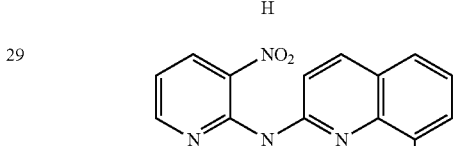 |
| 30 | 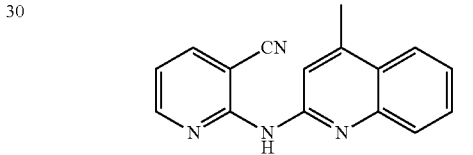 |

TABLE I-continued
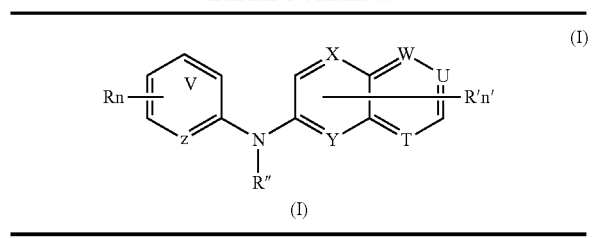
| 31 | 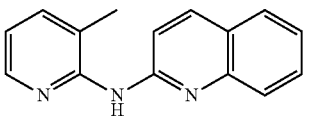 [SMILES: Cc1cccnc1Nc1ccc2ccccc2n1] |
| --- | --- |
| 32 | 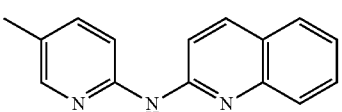 |
| 33 | 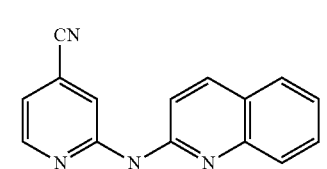 |
| 34 | 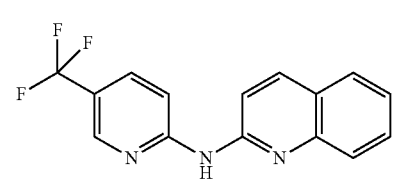 [SMILES: FC(F)(F)c1ccc(Nc2ccc3ccccc3n2)nc1] |
| 35 | 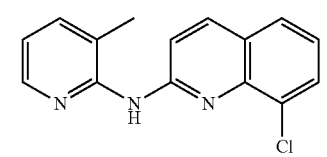 [SMILES: Cc1cccnc1Nc1ccc2cccc(Cl)c2n1] |
| 36 | 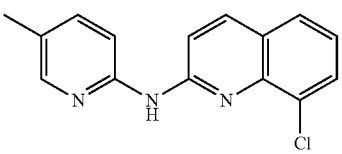 [SMILES: Cc1ccc(Nc2ccc3cccc(Cl)c3n2)nc1] |
| 37 | 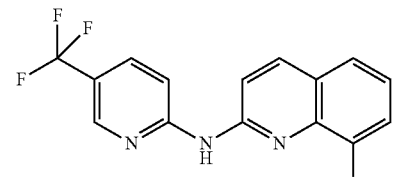 |
| 38 | 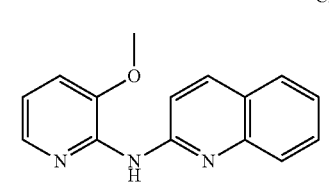 |
| 39 | 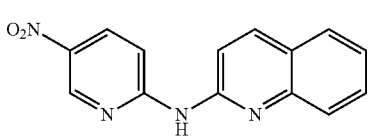 [SMILES: O=[N+]([O-])c1ccc(Nc2ccc3ccccc3n2)nc1] |
TABLE I-continued
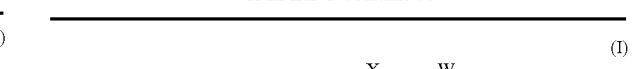
| 40 | 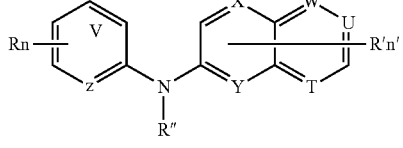 |
| --- | --- |
| 41 | 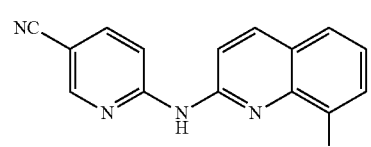 |
| 42 | 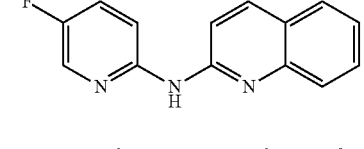 |
| 43 | 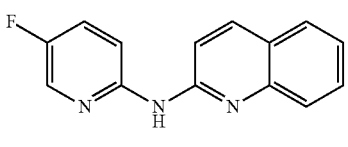 [SMILES: Fc1ccc(Nc2ccc3ccccc3n2)nc1] |
| 44 | 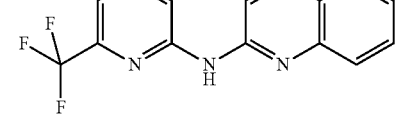 |
| 45 | 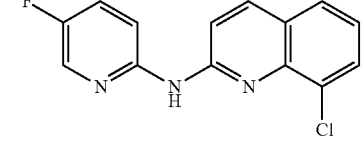 |
| 46 | 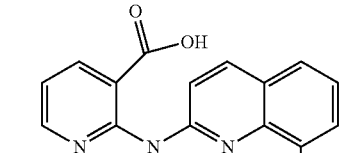 |
| 47 | 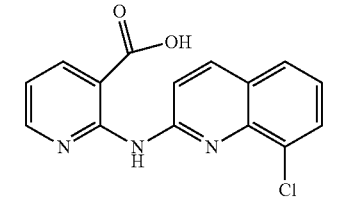 [SMILES: O=C(O)c1cccnc1Nc1ccc2cccc(Cl)c2n1] |

TABLE I-continued
(I)
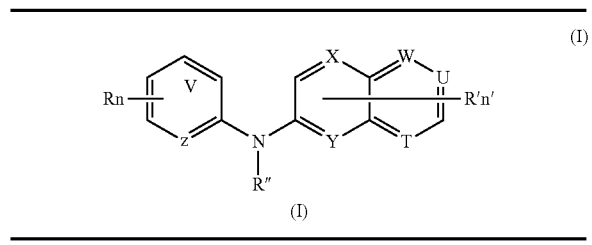
| 48 | 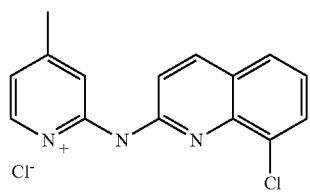 [SMILES: Cc1ccnc(Nc2ccc3cccc(Cl)c3n2)c1 ; [Cl-]] |
|---|---|
| 49 | 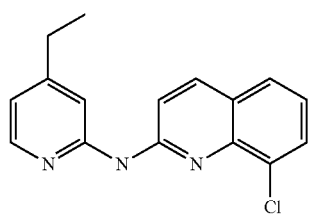 [SMILES: CCc1ccnc(Nc2ccc3cccc(Cl)c3n2)c1] |
| 50 | 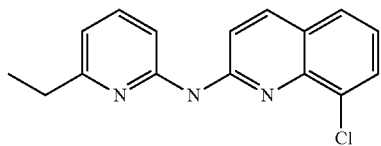 [SMILES: CCc1cccc(Nc2ccc3cccc(Cl)c3n2)n1] |
| 51 | 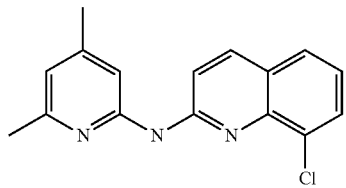 [SMILES: Cc1cc(C)nc(Nc2ccc3cccc(Cl)c3n2)c1] |
| 52 | 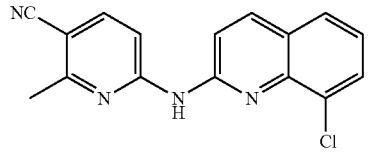 [SMILES: Cc1nc(Nc2ccc3cccc(Cl)c3n2)ccc1C#N] |
| 53 | 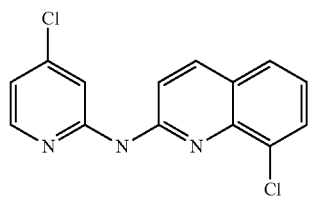 |
| 54 | 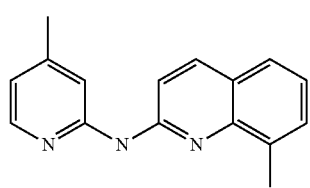 [SMILES: Cc1ccnc(Nc2ccc3cccc(C)c3n2)c1] |
| 55 | 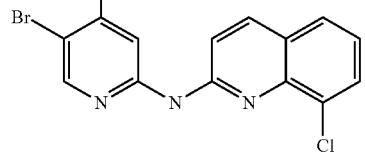 |
| 56 | 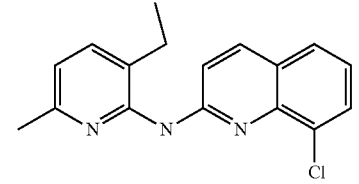 [SMILES: CCc1ccc(C)nc1Nc1ccc2cccc(Cl)c2n1] |
| 57 | 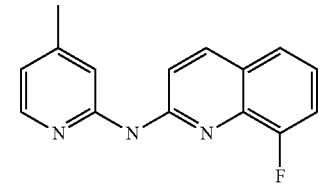 [SMILES: Cc1ccnc(Nc2ccc3cccc(F)c3n2)c1] |
| 58 | 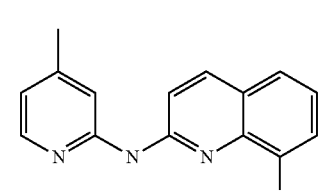 |
| 59 | 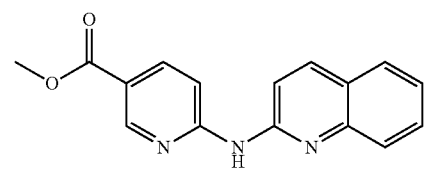 [SMILES: COC(=O)c1ccc(Nc2ccc3ccccc3n2)nc1] |
| 60 | 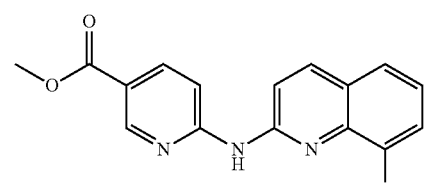 |
| 61 | 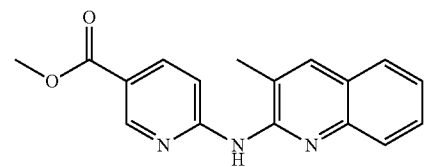 [SMILES: COC(=O)c1ccc(Nc2nc3ccccc3cc2C)nc1] |

TABLE I-continued
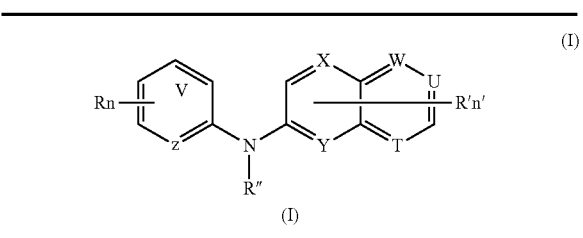
| 62 | 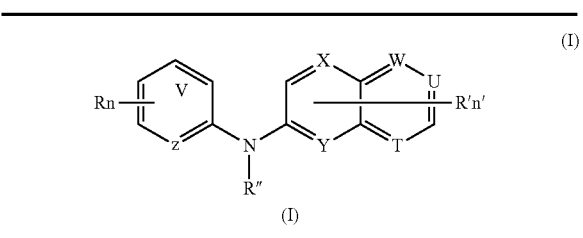 |
|---|---|
| 63 | 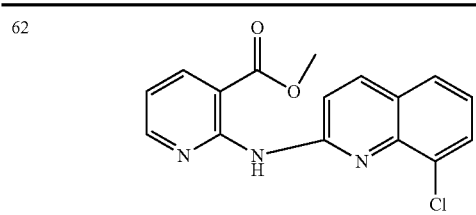 |
| 64 | 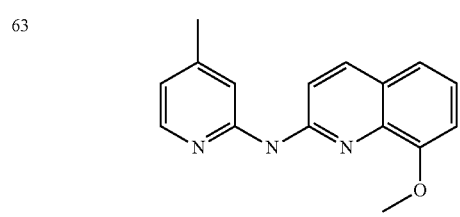 |
| 65 | 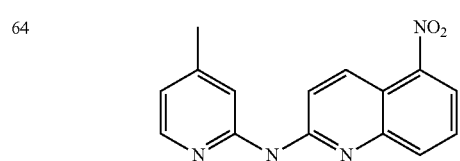 |
| 66 | 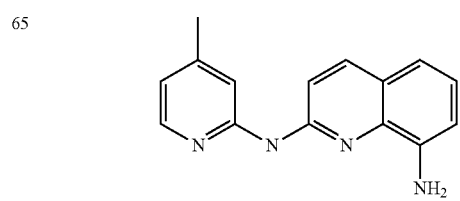 |
| 67 | 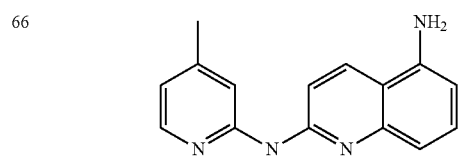 |
| 68 |  |
| 69 | 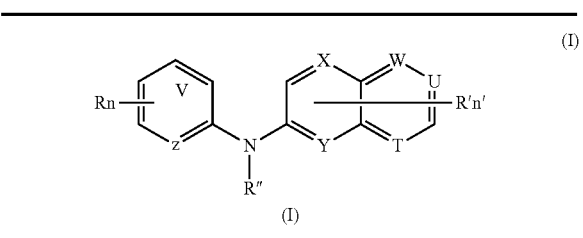 |
|---|---|
| 70 | 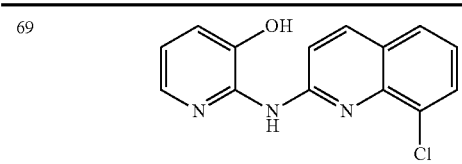 |
| 71 | 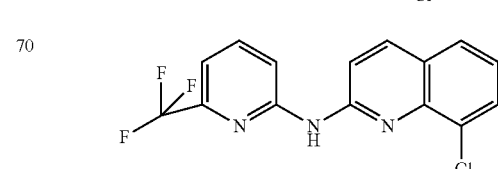 |
| 72 | 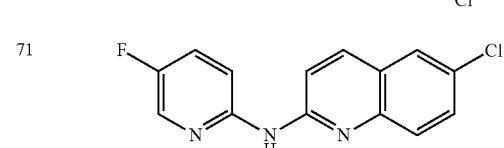 |
| 73 | 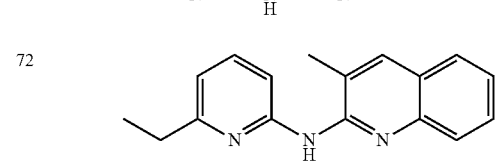 |
| 74 |  |
| 150 | 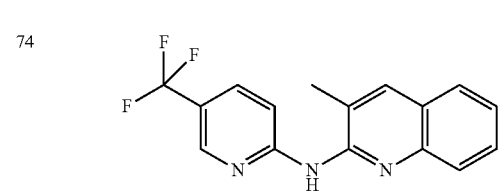 |
| 151 | 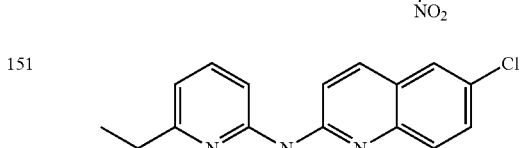 |
| 152 | 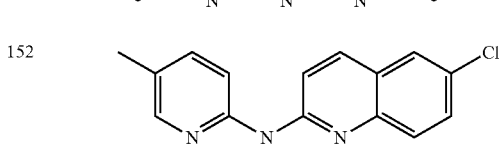 |

TABLE I-continued

Structure (I): Rn-[V-Z ring]-N(R")-[Y=X-W-U-T ring]-R'n'

| # | Structure description |
|---|---|
| 153 | 5-(trifluoromethyl)pyridin-2-yl / 6-chloroquinolin-2-yl amine |
| 154 | 3-amino-4-methylpyridin-2-yl / 8-chloroquinolin-2-yl amine |

Formula (Ib)

| # | Structure description |
|---|---|
| 8 | 4-(trifluoromethoxy)phenyl / quinolin-2-yl amine |
| 75 | 4-(dimethylamino)phenyl / 8-chloroquinolin-2-yl amine |
| 76 | 4-methoxyphenyl / quinolin-2-yl amine |
| 77 | 4-methoxyphenyl / 8-chloroquinolin-2-yl amine |
| 78 | 4-(trifluoromethoxy)phenyl / 4-methylquinolin-2-yl amine |
| 79 | 4-methoxyphenyl / 3-methylquinolin-2-yl amine |
| 80 | 4-(trifluoromethoxy)phenyl / 3-methylquinolin-2-yl amine |
| 81 | 4-(dimethylamino)phenyl / 3-methylquinolin-2-yl amine |
| 82 | 4-(trifluoromethoxy)-2-methylphenyl / quinolin-2-yl amine |
| 83 | 3-(trifluoromethoxy)phenyl / quinolin-2-yl amine |
| 84 | 2-(trifluoromethoxy)phenyl / quinolin-2-yl amine |
| 85 | 4-nitrophenyl / quinolin-2-yl amine |
| 86 | 3-fluorophenyl / quinolin-2-yl amine |
| 87 | 3-(trifluoromethoxy)phenyl / 8-chloroquinolin-2-yl amine |

TABLE I-continued
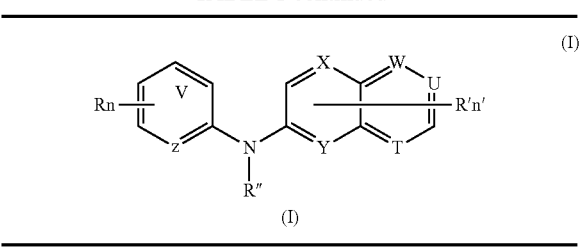
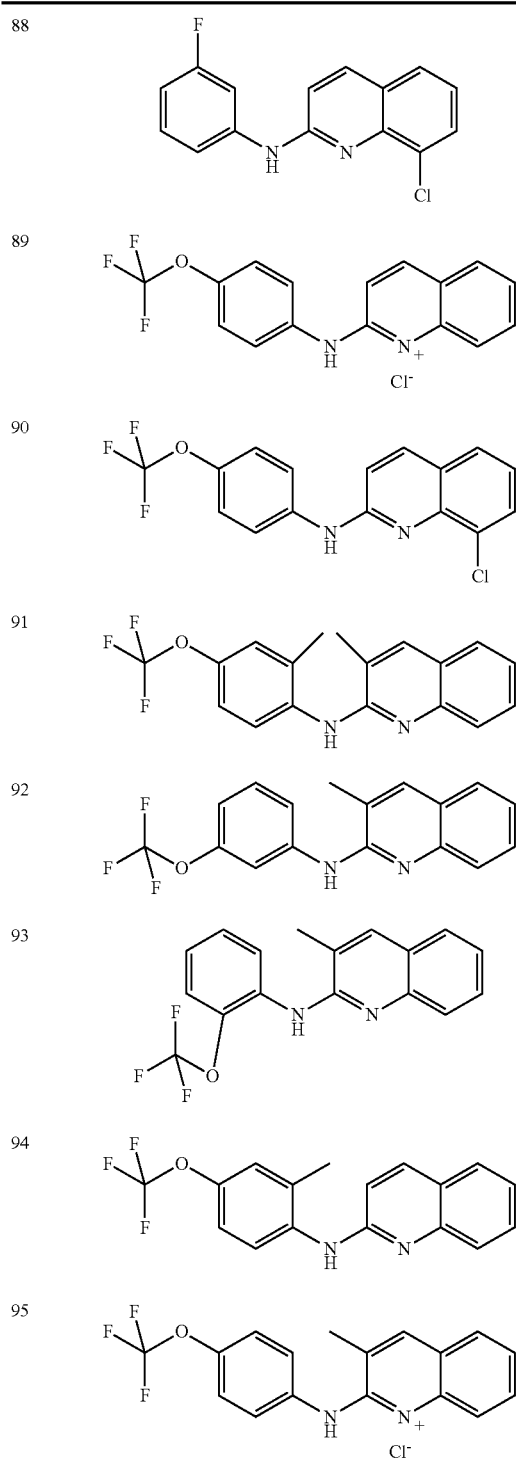
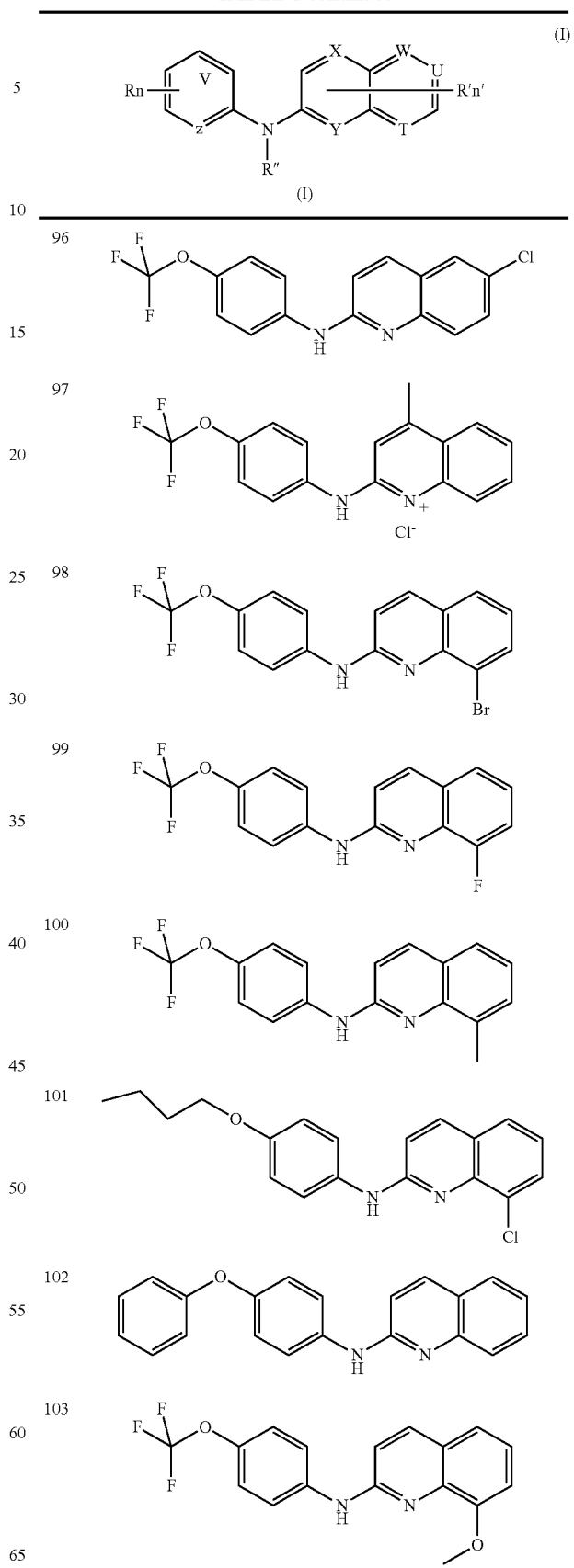

TABLE I-continued

Structure (I): Rn—[V/Z ring]—N(R")—[X,W,U,Y,T ring]—R'n'

| # | Compound description |
|---|---|
| 104 | 3-Cl, 4-OCF3-phenyl-NH-(8-Cl-quinolin-2-yl) |
| 155 | 4-butoxy-phenyl-N=(3-methyl-quinolin-2-yl) |
| 156 | 4-(dimethylamino)-phenyl-N=(6-Cl-quinolin-2-yl) |
| 157 | 3-Cl, 4-OMe-phenyl-NH-(8-Cl-quinolin-2-yl) |
| 158 | 2-NH2, 4-OCF3-phenyl-NH-(8-Cl-quinolin-2-yl) |

Formula (Ic)

| # | Compound description |
|---|---|
| 9 | pyridin-2-yl-NH-quinolin-3-yl |
| 10 | 3-methoxy-pyridin-2-yl-NH-quinolin-3-yl |
| 11 | 5-CF3-pyridin-2-yl-NH-quinolin-3-yl |
| 12 | 5-NO2-pyridin-2-yl-NH-quinolin-3-yl |
| 13 | 5-methyl-pyridin-2-yl-NH-quinolin-3-yl |
| 14 | 2-(quinolin-3-ylamino)isonicotinic acid |
| 105 | 6-methyl-pyridin-2-yl-NH-quinolin-3-yl |
| 106 | 3-NO2-pyridin-2-yl-NH-quinolin-3-yl |
| 159 | 3-NH2-pyridin-2-yl-N=quinolin-3-yl |

Formula (Id)

| # | Compound description |
|---|---|
| 15 | 5-CF3-pyridin-2-yl-NH-quinolin-6-yl |
| 16 | 6-methyl-pyridin-2-yl-NH-quinolin-6-yl |
| 107 | 5-methyl-pyridin-2-yl-NH-quinolin-6-yl |

TABLE I-continued (I)

| No. | Structure |
|---|---|
| 108 | 3-methoxypyridin-2-yl-NH-quinolin-6-yl |
| | Formula (Ie) |
| 109 | pyrazin-2-yl-NH-(6-chloroquinolin-2-yl) |
| 110 | pyrazin-2-yl-NH-(8-bromoquinolin-2-yl) |
| 111 | pyrazin-2-yl-NH-(8-methylquinolin-2-yl) |
| 112 | pyrazin-2-yl-NH-(8-chloroquinolin-2-yl) |
| 113 | pyrazin-2-yl-NH-quinolin-2-yl |
| 114 | pyrazin-2-yl-NH-(4-methylquinolin-2-yl) |
| 115 | pyrazin-2-yl-NH-(3-methylquinolin-2-yl) |
| 116 | pyrazin-2-yl-NH-(8-fluoroquinolin-2-yl) |
| 117 | pyrazin-2-yl-NH-(8-methoxyquinolin-2-yl) |
| | Formula (If) |
| 118 | pyridin-3-yl-NH-quinolin-3-yl |
| | Formula (Ig) |
| 119 | pyridin-4-yl-NH-(8-chloroquinolin-2-yl) |
| 120 | pyridin-4-yl-NH-quinolin-2-yl |
| | Formula (Ih) |
| 121 | pyridin-4-yl-NH-quinolin-3-yl |
| | Formula (Ii) |
| 122 | 4-(trifluoromethoxy)phenyl-NH-quinolin-3-yl |
| 123 | 4-methoxyphenyl-NH-quinolin-3-yl |
| | Formula (Ij) |
| 124 | 4-(trifluoromethoxy)phenyl-N=quinoxalin-2-yl |

TABLE I-continued

| | |
|---|---|
| 125 | 4-(trifluoromethoxy)-2-methylphenyl-quinoxalin-2-amine |
| 126 | 3-(trifluoromethoxy)phenyl-quinoxalin-2-amine |
| 127 | 2-(trifluoromethoxy)phenyl-quinoxalin-2-amine |

Formula (Ik)

| | |
|---|---|
| 128 | N-(pyrimidin-2-yl)quinolin-2-amine |
| 129 | 8-chloro-N-(pyrimidin-2-yl)quinolin-2-amine |
| 130 | 4-methyl-N-(pyrimidin-2-yl)quinolin-2-amine |

Formula (Il)

| | |
|---|---|
| 131 | N-(pyrazin-2-yl)quinolin-6-amine |

Formula (Im)

| | |
|---|---|
| 132 | N-(pyrazin-2-yl)quinolin-3-amine |

Formula (Io)

| | |
|---|---|
| 135 | N-(pyridin-2-yl)quinoxalin-2-amine |
| 136 | 4-methyl-N-(pyridin-2-yl)quinoxalin-2-amine |
| 137 | 6-(quinoxalin-2-ylamino)nicotinonitrile |
| 138 | 6-methyl-N-(pyridin-2-yl)quinoxalin-2-amine |
| 139 | 4-methyl-N-(3-(trifluoromethyl)quinoxalin-2-yl)pyridin-2-amine |
| 140 | 3,5-dichloro-4-methyl-N-(quinoxalin-2-yl)pyridin-2-amine |
| 141 | 4-methyl-3-nitro-N-(quinoxalin-2-yl)pyridin-2-amine |
| 160 | 6-chloro-N-(4-methylpyridin-2-yl)quinoxalin-2-amine |

TABLE I-continued
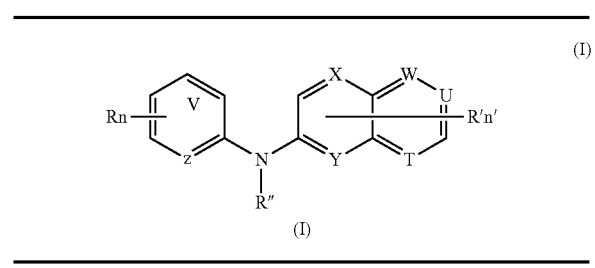
| 161 | 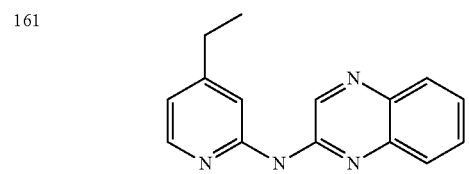 |
| 162 | 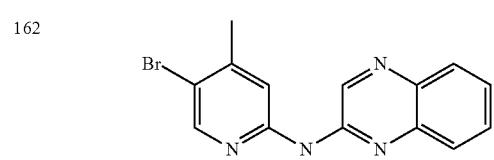 |
| 163 | 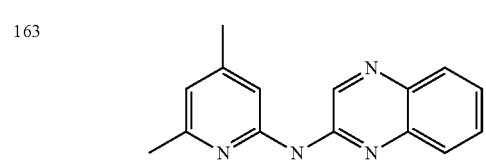 |
| 164 | 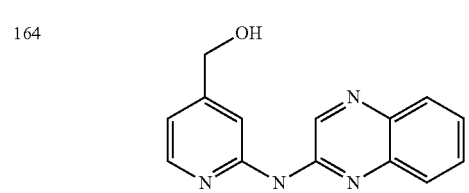 |
| 165 | 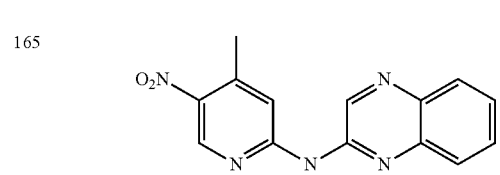 |
Formula (Ip)
| 142 | 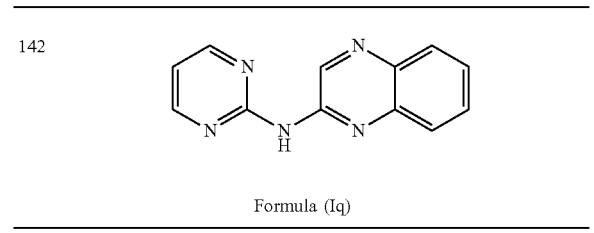 |
Formula (Iq)
| 143 | 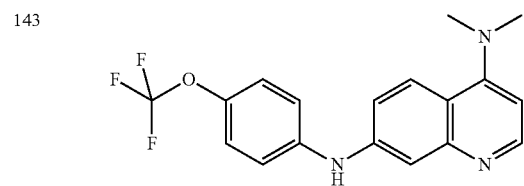 |
TABLE I-continued
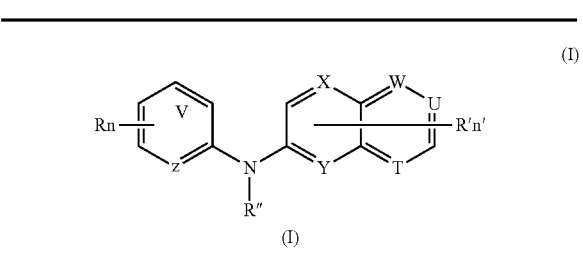
| 144 | 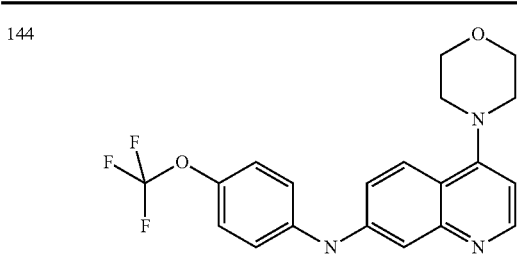 |
| 166 | 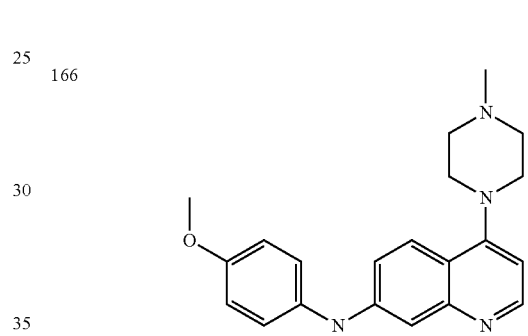 |
| 167 | 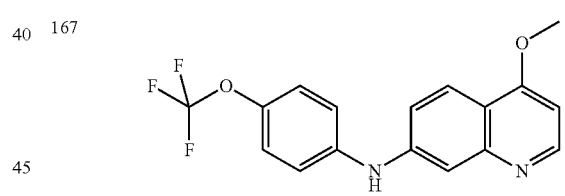 |
Formula (Ir)
| 145 | 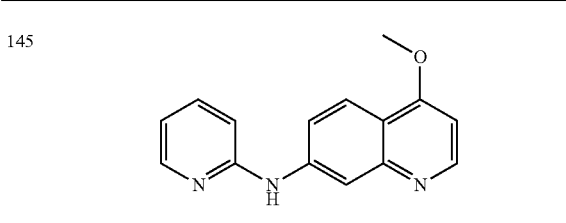 |
| 146 | 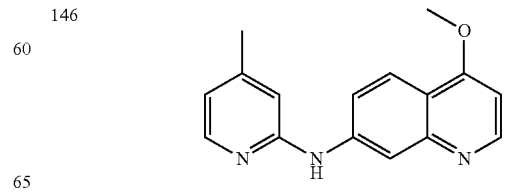 |

TABLE I-continued (I)

[Structure showing Rn-V-Z-N(R")-Y-T-U-R'n' with X-W framework]

| | |
|---|---|
| 147 | [4-methylpyridin-2-yl]-NH-[quinolin-7-yl with 4-N(CH₃)₂] |
| 168 | [4-methylpyridin-2-yl]-NH-[quinolin-7-yl with 4-morpholino] |

TABLE I-continued (I)

[Structure showing Rn-V-Z-N(R")-Y-T-U-R'n' with X-W framework]

Formula (Iee)

| | |
|---|---|
| 148 | [5-methylpyridin-2-yl]-N-[5-methylisoquinolin-6-yl] (with 8-methyl) |
| 149 | [5-(trifluoromethyl)pyridin-2-yl]-N-[5-methylisoquinolin-6-yl] (with 8-methyl) |

TABLE II

| Ex | Characterizations |
|---|---|
| 1 | MS (ESI) [M + H]⁺ = 256 |
| 2 | ¹H NMR (300 MHz, D₂O) δ 8.31 (d, J = 5.1, 1H), 8.21 (d, J = 9.3, 1H), 7.60 (d, J = 7.5, 3H), 7.34 (dd, J = 6.2, 15.6, 2H), 7.18 (s, 1H), 6.99 (d, J = 9.1, 1H) MS (ESI) [M + H]⁺ = 266 |
| 5 | MS (ESI) [M + H]⁺ = 300 |
| 6 | ¹H NMR (300 MHz, DMSO) δ 10.23 (s, 1H), 8.96 (s, 1H), 8.18 (d, J = 8.8, 2H), 7.78 (dd, J = 7.7, 13.7, 2H), 7.46 (d, J = 8.9, 1H), 7.31 (t, J = 7.8, 1H), 6.86 (d, J = 4.3, 1H), 2.37 (s, 3H). ¹³C NMR (75 MHz, DMSO) δ 153.63, 153.61, 148.37, 147.32, 142.65, 137.52, 129.68, 129.47, 126.82, 125.06, 123.26, 118.36, 115.10, 113.31, 21.24. MS (ESI) [M + H]⁺ = 270 |
| 7 | ¹H NMR (300 MHz, DMSO) δ 10.71 (s, 1H), 8.71 (d, J = 1.4, 1H), 8.62 (d, J = 8.9, 1H), 8.24 (d, J = 8.9, 1H), 8.17 (dd, J = 1.9, 8.9, 1H), 7.89-7.74 (m, 2H), 7.66 (dd, J = 7.9, 14.2, 2H), 7.42 (t, J = 7.3, 1H). ¹³C NMR (75 MHz, DMSO) δ 156.09, 152.40, 152.11, 146.24, 141.07, 137.83, 129.87, 127.67, 126.78, 124.50, 124.21, 118.04, 114.49, 111.67, 100.12. MS (ESI) [M + H]⁺ = 247 |
| 8 | ¹H NMR (300 MHz, CDCl₃) δ 7.92 (d, J = 8.9, 1H), 7.79 (d, J = 8.4, 1H), 7.65 (t, J = 7.7, 3H), 7.59 (dd, J = 7.1, 8.3, 1H), 7.31 (t, J = 7.0, 1H), 7.20 (d, J = 8.5, 2H), 6.88 (d, J = 8.9, 1H), 6.80 (s, 1H) ¹³C NMR (75 MHz, CDCl₃) δ 153.88, 147.62, 144.35, 139.26, 138.11, 130.13, 127.65, 127.12, 124.43, 123.70, 122.20, 120.95, 112.25. MS (ESI) [M + H]⁺ = 305 |
| 10 | ¹H NMR (300 MHz, CDCl₃) δ 9.10 (d, J = 2.5, 1H), 8.83 (d, J = 2.6, 1H), 8.02 (d, J = 7.9, 1H), 7.94 (dd, J = 1.3, 5.0, 1H), 7.85-7.79 (m, 1H), 7.52 (pd, J = 1.5, 6.9, 2H), 7.33 (s, 1H), 7.04 (dd, J = 1.2, 7.9, 1H), 6.81 (dd, J = 5.1, 7.9, 1H), 3.95 (s, 3H) |
| 11 | MS (ESI) [M + H]⁺ = 290 |
| 12 | ¹H NMR (300 MHz, CDCl₃) δ 9.18 (d, J = 2.7, 1H), 8.86 (d, J = 2.5, 1H), 8.56 (d, J = 2.3, 1H), 8.33 (dd, J = 2.7, 9.2, 1H), 8.08 (d, J = 8.5, 1H), 7.83 (d, J = 8.5, 1H), 7.71-7.63 (m, 2H), 7.57 (t, J = 7.4, 2H), 6.82 (d, J = 9.1, 1H) |
| 13 | ¹H NMR (300 MHz, CDCl₃) δ 8.83 (d, J = 2.6, 1H), 8.37 (d, J = 2.3, 1H), 8.00 (d, J = 8.2, 1H), 7.71 (d, J = 7.7, 1H), 7.59-7.51 (m, 1H), 7.46 (dd, J = 7.3, 15.1, 2H), 6.71 (d, J = 8.3, 1H), 6.67 (d, J = 7.4, 1H), 2.49 (s, 3H) ¹³C NMR (75 MHz, CDCl₃) δ 157.13, 154.59, 145.81, 144.43, 138.78, 134.54, 129.22, 128.86, 127.41, 127.27, 121.48, 115.41, 106.50, 24.18. MS (ESI) [M + H]⁺ = 236 |
| 14 | MS (ESI) [M + H]⁺ = 266 |
| 15 | MS (ESI) [M + H]⁺ = 290 |
| 16 | ¹H NMR (300 MHz, CDCl₃) δ 8.77 (dd, J = 1.5, 4.2, 1H), 8.04 (dd, J = 4.7, 8.7, 2H), 7.92 (d, J = 2.4, 1H), 7.59 (dd, J = 2.5, 9.1, 1H), 7.47 (t, J = 7.8, 1H), |

TABLE II-continued

| Ex | Characterizations |
|---|---|
| | 7.35 (dd, J = 4.2, 8.3, 1H), 6.87 (s, 1H), 6.81 (d, J = 8.2, 1H), 6.70 (d, J = 7.4, 1H), 2.50 (s, 3H)<br>MS (ESI) [M + H]$^+$ = 236 |
| 18 | $^1$H NMR (300 MHz, CDCl$_3$) δ 8.53 (d, J = 59.9, 2H), 7.76 (d, J = 8.6, 1H), 7.58 (t, J = 8.3, 2H), 7.42 (d, J = 7.8, 1H), 7.09 (t, J = 7.7, 1H), 6.95 (d, J = 8.7, 1H), 6.71 (d, J = 7.3, 1H), 2.38 (s, 3H) |
| 21 | $^1$H NMR (300 MHz, CDCl$_3$) δ 8.78 (s, 1H), 8.13 (d, J = 5.1, 1H), 7.89 (d, J = 8.3, 1H), 7.79 (s, 1H), 7.63 (d, J = 8.0, 1H), 7.56 (d, J = 7.3, 1H), 7.38 (s, 1H), 7.33 (t, J = 7.5, 1H), 6.79 (d, J = 4.9, 1H), 2.44 (s, 6H) |
| 22 | $^1$H NMR (300 MHz, CDCl$_3$) δ 8.95 (d, J = 8.4, 1H), 8.28 (d, J = 5.7, 1H), 7.87 (d, J = 8.3, 1H), 7.78 (s, 1H), 7.76-7.70 (m, 1H), 7.62 (d, J = 8.0, 1H), 7.60-7.52 (m, 1H), 7.42 (s, 1H), 7.32 (t, J = 7.4, 1H), 6.95 (dd, J = 5.1, 6.5, 1H), 2.45 (s, 3H) |
| 23 | $^1$H NMR (300 MHz, CDCl$_3$) δ 8.64 (d, J = 8.4, 1H), 8.55 (d, J = 2.1, 1H), 8.03 (s, 1H), 7.90 (d, J = 8.5, 4H), 7.66 (t, J = 7.6, 1H), 7.44 (t, J = 7.6, 1H), 7.06 (s, 1H), 2.67 (s, 4H) |
| 24 | $^1$H NMR (300 MHz, CDCl$_3$) δ 9.09 (d, J = 8.9, 1H), 8.53 (d, J = 1.7, 1H), 7.94 (dd, J = 2.2, 8.9, 1H), 7.92-7.84 (m, 2H), 7.67 (d, J = 8.6, 2H), 7.65-7.58 (m, 1H), 7.40 (t, J = 7.4, 1H), 2.49 (s, 3H) |
| 25 | $^1$H NMR (300 MHz, CDCl$_3$) δ 8.16 (d, J = 5.2, 1H), 8.10 (s, 1H), 7.90 (d, J = 8.8, 1H), 7.79 (d, J = 9.0, 1H), 7.66 (d, J = 2.2, 1H), 7.55 (dd, J = 2.3, 8.9, 1H), 7.39 (d, J = 9.0, 1H), 6.79 (d, J = 5.2, 1H), 2.42 (s, 3H)<br>MS (ESI) [M + H]$^+$ = 270 |
| 26 | $^1$H NMR (300 MHz, CDCl$_3$) δ 8.06 (d, J = 8.3, 1H), 7.70 (d, J = 9.0, 1H), 7.64 (d, J = 8.9, 1H), 7.49 (t, J = 7.9, 2H), 7.40 (dd, J = 2.3, 8.9, 1H), 7.18 (d, J = 8.9, 1H), 6.68 (d, J = 7.4, 1H), 2.38 (s, 3H)<br>MS (ESI) [M + H]$^+$ = 270 |
| 27 | $^1$H NMR (300 MHz, CDCl$_3$) δ 9.17 (d, J = 2.5, 1H), 8.71 (s, 1H), 8.49 (dd, J = 2.6, 9.0, 1H), 7.99 (s, 1H), 7.93 (d, J = 8.9, 2H), 7.74-7.64 (m, 1H), 7.48 (dd, J = 4.2, 11.4, 1H), 7.09 (s, 1H), 2.71 (s, 3H) |
| 28 | $^1$H NMR (300 MHz, CDCl$_3$) δ 8.64-8.51 (m, 3H), 8.18 (d, J = 9.0, 1H), 7.93 (d, J = 8.4, 1H), 7.79 (d, J = 8.1, 1H), 7.73-7.64 (m, 1H), 7.51-7.41 (m, 1H), 7.00 (dd, J = 4.6, 8.2, 1H), 6.75 (dd, J = 4.6, 8.3, 0H) |
| 29 | $^1$H NMR (300 MHz, CDCl$_3$) δ 10.77 (s, 1H), 8.60 (s, 3H), 8.19 (d, J = 8.2, 1H), 7.76 (dd, J = 6.6, 25.5, 2H), 7.38 (d, J = 7.2, 1H), 7.04 (d, J = 4.4, 1H) |
| 30 | $^1$H NMR (300 MHz, CDCl$_3$) δ 8.46 (dd, J = 1.9, 5.0, 1H), 7.87 (dd, J = 2.0, 7.6, 1H), 7.82 (d, J = 7.3, 1H), 7.60 (t, J = 7.3, 2H), 7.43-7.33 (m, 1H), 6.90 (dd, J = 5.0, 7.6, 1H), 2.64 (s, 3H) |
| 31 | $^1$H NMR (300 MHz, CDCl$_3$) δ 8.44 (d, J = 9.1, 1H), 8.17 (d, J = 4.8, 1H), 8.03 (d, J = 9.1, 1H), 7.78 (d, J = 8.4, 1H), 7.68 (d, J = 8.0, 1H), 7.62-7.54 (m, 1H), 7.39 (d, J = 7.3, 1H), 7.32 (t, J = 7.5, 1H), 6.82 (dd, J = 5.0, 7.3, 1H), 2.31 (s, 3H)<br>MS (ESI) [M + H]$^+$ = 236 |
| 32 | $^1$H NMR (300 MHz, CDCl$_3$) δ 8.23 (d, J = 8.5, 1H), 8.10 (s, 1H), 7.91 (d, J = 8.9, 1H), 7.82 (d, J = 8.4, 1H), 7.62 (d, J = 8.3, 1H), 7.56 (d, J = 7.3, 1H), 7.50 (dd, J = 1.8, 8.5, 1H), 7.37-7.24 (m, 2H), 2.26 (s, 3H)<br>MS (ESI) [M + H]$^+$ = 236 |
| 33 | $^1$H NMR (300 MHz, CDCl$_3$) δ 8.87 (s, 1H), 8.32 (d, J = 5.0, 1H), 7.95 (d, J = 8.8, 1H), 7.84 (d, J = 8.3, 1H), 7.60 (dd, J = 7.4, 14.1, 2H), 7.32 (t, J = 7.5, 1H), 7.04 (dd, J = 5.0, 9.0, 2H)<br>MS (ESI) [M + H]$^+$ = 247 |
| 34 | $^1$H NMR (300 MHz, CDCl$_3$) δ 8.52 (s, 1H), 8.45 (d, J = 8.6, 1H), 8.01 (d, J = 8.8, 1H), 7.87 (dd, J = 2.5, 8.5, 2H), 7.72-7.56 (m, 2H), 7.39 (d, J = 9.0, 2H)<br>MS (ESI) [M + H]$^+$ = 290 |
| 35 | $^1$H NMR (300 MHz, CDCl$_3$) δ 8.32 (d, J = 9.1, 1H), 8.07 (d, J = 4.8, 1H), 7.93 (d, J = 9.1, 1H), 7.59 (t, J = 7.9, 1H), 7.52 (d, J = 8.0, 1H), 7.36 (d, J = 7.2, 1H), 7.14 (t, J = 7.8, 1H), 6.77 (dd, J = 5.0, 7.3, 1H), 2.29 (s, 3H)<br>MS (ESI) [M + H]$^+$ = 270 |
| 36 | $^1$H NMR (300 MHz, CDCl$_3$) δ 8.70 (d, J = 7.2, 1H), 8.01 (s, 1H), 7.82 (d, J = 8.9, 1H), 7.62 (d, J = 7.6, 1H), 7.53 (dd, J = 1.8, 8.6, 1H), 7.46 (d, J = 7.9, 1H), 7.12 (t, J = 7.8, 1H), 7.05 (d, J = 8.8, 1H), 2.21 (s, 3H)<br>MS (ESI) [M + H]$^+$ = 270 |
| 37 | $^1$H NMR (300 MHz, CDCl$_3$) δ 9.08 (d, J = 8.5, 1H), 8.55 (s, 1H), 8.36 (s, 1H), 8.02 (d, J = 8.1, 2H), 7.77 (d, J = 7.2, 1H), 7.62 (d, J = 7.6, 1H), 7.35-7.24 (m, 1H), 7.12 (d, J = 8.8, 1H)<br>MS (ESI) [M + H]$^+$ = 324 |
| 38 | $^1$H NMR (300 MHz, CDCl$_3$) δ 8.69 (d, J = 9.1, 1H), 7.97 (d, J = 9.1, 1H), 7.80-7.74 (m, 1H), 7.70 (d, J = 8.4, 1H), 7.59 (d, J = 8.0, 1H), 7.54-7.45 (m, 1H), 7.22 (t, J = 7.5, 1H), 6.87 (d, J = 7.9, 1H), 6.68 (dd, J = 5.0, 7.9, 1H), 3.73 (s, 3H)<br>MS (ESI) [M + H]$^+$ = 252 |
| 39 | $^1$H NMR (300 MHz, CDCl$_3$) δ 8.57 (d, J = 29.4, 1H), 7.80 (d, J = 8.8, 1H), 7.66 (t, J = 6.7, 2H), 7.46 (d, J = 7.9, 1H), 7.14 (t, J = 7.8, 1H), 7.06 (d, J = 8.8, 1H), 6.79 (d, J = 7.3, 1H), 2.73 (dd, J = 7.6, 15.2, 2H), 1.28 (t, J = 7.7, 3H) |
| 40 | $^1$H NMR (300 MHz, DMSO) δ 9.75 (s, 1H), 9.12 (d, J = 2.3, 1H), 8.50 (d, J = 2.2, 1H), 8.48 (s, 1H), 8.13 (s, 1H), 7.83 (s, 1H), 7.80 (s, 1H), 7.64 (t, J = 7.7, 1H), 7.45 (t, J = 7.8, 1H) |
| 41 | $^1$H NMR (300 MHz, CDCl$_3$) δ 8.52 (dd, J = 2.8, 8.6, 1H), 8.35 (s, 1H), 8.15 (d, J = 2.3, 1H), 7.94 (d, J = 8.8, 1H), 7.84 (d, J = 8.2, 1H), 7.65 (d, J = 7.8, 1H), 7.59 (d, J = 7.2, 1H), 7.50-7.40 (m, 1H), 7.33 (t, J = 7.4, 1H), 7.11 (d, J = 8.9, 1H)<br>MS (ESI) [M + H]$^+$ = 240 |

TABLE II-continued

| Ex | Characterizations |
|---|---|
| 42 | $^1$H NMR (300 MHz, CDCl$_3$) δ 8.55 (d, J = 6.8, 1H), 8.01 (d, J = 8.9, 2H), 7.82 (dd, J = 9.1, 17.3, 2H), 7.69 (d, J = 8.0, 1H), 7.63 (t, J = 7.6, 1H), 7.37 (t, J = 7.5, 1H), 7.32-7.18 (m, 2H)<br>MS (ESI) [M + H]$^+$ = 290 |
| 43 | $^1$H NMR (300 MHz, DMSO) δ 10.41 (s, 1H), 9.08 (dd, J = 4.1, 9.3, 1H), 8.31 (d, J = 2.9, 1H), 8.20 (d, J = 8.9, 1H), 7.88-7.70 (m, 3H), 7.44 (d, J = 8.9, 1H), 7.32 (t, J = 7.8, 1H)<br>$^{13}$C NMR (75 MHz, DMSO) δ 156.30, 153.32, 153.04, 150.17, 142.55, 137.73, 135.06, 134.74, 129.58, 129.49, 126.86, 125.29, 125.14, 125.04, 123.36, 114.91, 113.36.<br>MS (ESI) [M + H]$^+$ = 274 |
| 44 | $^1$H NMR (300 MHz, CDCl$_3$) δ 11.09 (s, 1H), 8.78 (d, J = 9.0, 1H), 8.42 (dd, J = 1.9, 4.7, 1H), 8.28 (dd, J = 1.9, 7.8, 1H), 8.11 (d, J = 9.1, 1H), 7.73 (d, J = 7.5, 1H), 7.65 (d, J = 8.1, 1H), 7.27 (dd, J = 6.4, 9.2, 1H), 6.88 (dd, J = 4.8, 7.8, 1H)<br>MS (ESI) [M + H]$^+$ = 300 |
| 46 | $^1$H NMR (300 MHz, CDCl$_3$) δ 8.59 (d, J = 8.3, 1H), 7.73 (d, J = 8.3, 1H), 7.57 (s, 1H), 7.51 (t, J = 7.9, 1H), 7.43 (t, J = 9.2, 2H), 7.17 (t, J = 7.4, 1H), 6.67 (d, J = 7.4, 1H), 2.36 (s, 3H), 2.28 (s, 3H) |
| 47 | $^1$H NMR (300 MHz, MeOD) δ 8.99 (s, 1H), 8.76 (d, J = 9.2, 1H), 8.32 (d, J = 8.7, 1H), 8.22 (d, J = 8.6, 1H), 8.11 (d, J = 7.8, 1H), 8.01 (t, J = 7.1, 1H), 7.76 (t, J = 7.4, 1H), 7.55-7.43 (m, 2H)<br>MS (ESI) [M + H]$^+$ = 247 |
| 48 | $^1$H NMR (300 MHz, MeOD) δ 8.48 (d, J = 9.1, 1H), 8.40 (d, J = 6.7, 1H), 7.94 (d, J = 8.4, 1H), 7.90 (d, J = 7.8, 1H), 7.54 (t, J = 8.0, 1H), 7.38 (d, J = 8.6, 1H), 7.30 (s, 2H), 2.58 (s, 3H)<br>MS (ESI) [M + H]$^+$ = 270 |
| 49 | $^1$H NMR (300 MHz, CDCl$_3$) δ 9.34 (s, 1H), 8.95 (s, 1H), 8.21 (d, J = 5.1, 1H), 7.87 (d, J = 8.9, 1H), 7.71 (d, J = 7.5, 1H), 7.52 (d, J = 7.9, 1H), 7.19 (t, J = 7.8, 1H), 7.05 (d, J = 8.9, 1H), 6.84 (d, J = 5.1, 1H), 2.76 (q, J = 7.6, 2H), 1.37 (t, J = 7.6, 3H) |
| 50 | $^1$H NMR (300 MHz, CDCl$_3$) δ 8.57 (d, J = 29.4, 1H), 7.80 (d, J = 8.8, 1H), 7.66 (t, J = 6.7, 2H), 7.46 (d, J = 7.9, 1H), 7.14 (t, J = 7.8, 1H), 7.06 (d, J = 8.8, 1H), 6.79 (d, J = 7.3, 1H), 2.73 (dd, J = 7.6, 15.2, 2H), 1.28 (t, J = 7.7, 3H) |
| 51 | $^1$H NMR (300 MHz, CDCl$_3$) δ 8.64 (s, 1H), 8.06 (s, 1H), 7.89 (d, J = 8.7, 1H), 7.71 (d, J = 7.4, 1H), 7.54 (d, J = 7.8, 1H), 7.20 (t, J = 7.7, 1H), 7.02 (d, J = 8.8, 1H), 6.67 (s, 1H), 2.43 (s, 3H), 2.39 (s, 3H)<br>$^{13}$C NMR (75 MHz, CDCl$_3$) δ 156.15, 153.17, 152.82, 150.16, 143.70, 137.92, 131.34, 129.89, 126.49, 125.47, 123.43, 118.62, 114.47, 111.02, 24.13, 21.70.<br>MS (ESI) [M + H]$^+$ = 284 |
| 52 | $^1$H NMR (300 MHz, CDCl$_3$) δ 8.89 (d, J = 8.8, 1H), 8.05 (d, J = 8.8, 1H), 8.01 (s, 1H), 7.93 (d, J = 8.8, 1H), 7.79 (d, J = 7.5, 1H), 7.64 (d, J = 8.0, 1H), 7.32 (t, J = 7.8, 1H), 7.13 (d, J = 8.8, 1H), 2.67 (s, 3H) |
| 53 | $^1$H NMR (300 MHz, CDCl$_3$) δ 9.27 (s, 1H), 8.33 (d, J = 5.7, 1H), 8.13 (d, J = 5.2, 1H), 8.00 (d, J = 8.8, 1H), 7.76 (d, J = 7.4, 1H), 7.60 (d, J = 8.0, 1H), 7.29 (d, J = 7.9, 1H), 7.07 (d, J = 8.9, 1H), 6.97 (d, J = 4.8, 1H) |
| 54 | MS (ESI) [M + H]$^+$ = 250 |
| 55 | $^1$H NMR (300 MHz, CDCl$_3$) δ 8.19 (s, 1H), 7.90 (d, J = 9.0, 1H), 7.63 (d, J = 7.5, 1H), 7.52 (d, J = 7.9, 1H), 7.33 (d, J = 7.4, 1H), 7.14 (t, J = 7.8, 1H), 6.69 (d, J = 7.5, 1H), 2.70 (dd, J = 7.3, 14.8, 2H), 2.47 (s, 3H), 1.26 (t, J = 7.7, 3H) |
| 56 | $^1$H NMR (300 MHz, CDCl$_3$) δ 8.20 (s, 1H), 7.90 (d, J = 9.0, 1H), 7.63 (d, J = 7.5, 1H), 7.52 (d, J = 7.9, 1H), 7.33 (d, J = 7.4, 1H), 7.14 (t, J = 7.8, 1H), 6.69 (d, J = 7.5, 1H), 2.70 (dd, J = 7.3, 14.8, 2H), 2.47 (s, 3H), 1.25 (dd, J = 7.5, 15.5, 3H) |
| 57 | MS (ESI) [M + H]$^+$ = 253 |
| 58 | MS (ESI) [M + H]$^+$ = 314-316 |
| 59 | $^1$H NMR (300 MHz, CDCl$_3$) δ 8.91 (d, J = 1.7, 1H), 8.46 (d, J = 8.8, 1H), 8.28 (dd, J = 2.0, 8.8, 1H), 8.23 (s, 1H), 8.03 (d, J = 8.8, 1H), 7.88 (d, J = 8.3, 1H), 7.70 (d, J = 8.0, 1H), 7.67-7.58 (m, 1H), 7.38 (t, J = 7.4, 1H), 7.32 (d, J = 8.8, 2H), 3.91 (s, 3H) |
| 60 | $^1$H NMR (300 MHz, CDCl$_3$) δ 8.94 (d, J = 8.9, 1H), 8.91 (d, J = 1.8, 1H), 8.37 (dd, J = 2.2, 8.8, 1H), 8.04 (d, J = 8.9, 2H), 7.77 (d, J = 7.5, 1H), 7.62 (d, J = 7.2, 1H), 7.30 (t, J = 7.8, 2H), 7.19 (d, J = 8.8, 2H), 3.92 (s, 3H) |
| 61 | $^1$H NMR (300 MHz, CDCl$_3$) δ 8.96 (d, J = 8.8, 1H), 8.85 (d, J = 1.3, 1H), 8.28 (d, J = 9.9, 1H), 7.84 (d, J = 8.0, 1H), 7.77 (s, 1H), 7.65 (s, 1H), 7.59 (d, J = 8.4, 2H), 7.53 (d, J = 8.4, 1H), 7.31 (t, J = 7.4, 1H), 3.88 (s, 4H), 2.42 (s, 4H)<br>MS (ESI) [M + H]$^+$ = 294 |
| 62 | $^1$H NMR (300 MHz, CDCl$_3$) δ 11.02 (s, 1H), 8.75 (d, J = 9.2, 1H), 8.44 (d, J = 3.7, 1H), 8.31 (d, J = 7.9, 1H), 8.10 (d, J = 9.0, 1H), 7.72 (d, J = 7.5, 1H), 7.64 (d, J = 8.2, 1H), 7.27 (d, J = 8.1, 1H), 6.88 (dd, J = 4.7, 7.8, 1H), 3.97 (s, 3H)<br>MS (ESI) [M + H]$^+$ = 314 |
| 63 | MS (ESI) [M + H]$^+$ = 266 |
| 64 | $^1$H NMR (300 MHz, DMSO) δ 10.38 (s, 1H), 8.56 (s, 1H), 8.28 (d, J = 9.1, 1H), 8.20-8.03 (m, 3H), 7.50 (d, J = 8.7, 1H), 7.45 (d, J = 8.0, 1H), 6.88 (d, J = 4.4, 1H), 2.37 (s, 3H) |
| 65 | MS (ESI) [M + H]$^+$ = 314-316 |
| 66 | MS (ESI) [M + H]$^+$ = 250 |

TABLE II-continued

| Ex | Characterizations |
|---|---|
| 67 | ¹H NMR (300 MHz, DMSO) δ 10.51 (s, 1H), 8.83 (d, J = 2.3, 1H), 8.62 (d, J = 9.3, 1H), 8.24 (dd, J = 2.7, 9.1, 1H), 7.96 (d, J = 8.9, 1H), 7.81 (d, J = 7.8, 1H), 7.67 (t, J = 7.6, 1H), 7.45 (d, J = 11.2, 2H), 3.86 (s, 3H), 2.62 (s, 3H)<br>MS (ESI) [M + H]⁺ = 294 |
| 68 | ¹H NMR (300 MHz, CDCl₃) δ 9.57 (s, 1H), 8.44 (d, J = 4.8, 1H), 8.05 (d, J = 8.8, 1H), 7.86 (s, 1H), 7.80 (d, J = 7.5, 1H), 7.64 (d, J = 8.0, 1H), 7.31 (t, J = 7.8, 1H), 7.19 (d, J = 4.3, 1H), 7.04 (d, J = 8.8, 1H) |
| 69 | ¹H NMR (300 MHz, CDCl₃) δ 9.12 (s, 1H), 7.94 (d, J = 8.6, 1H), 7.71 (d, J = 7.5, 1H), 7.57 (d, J = 7.8, 1H), 7.40 (s, 1H), 7.25 (d, J = 10.2, 2H), 7.17 (s, 1H), 7.05 (s, 1H) |
| 70 | ¹H NMR (300 MHz, CDCl₃) δ 9.07 (d, J = 8.5, 1H), 7.97 (d, J = 8.8, 1H), 7.90 (t, J = 8.0, 1H), 7.84 (s, 1H), 7.75 (dd, J = 1.1, 7.5, 1H), 7.62-7.55 (m, 1H), 7.31 (d, J = 7.6, 1H), 7.27 (t, J = 7.8, 1H), 7.08 (d, J = 8.8, 1H)<br>MS (ESI) [M + H]⁺ = 274 |
| 71 | MS (ESI) [M + H]⁺ = 274 |
| 72 | ¹H NMR (300 MHz, CDCl₃) δ 8.67 (d, J = 7.9, 1H), 7.83 (d, J = 8.3, 1H), 7.71 (s, 1H), 7.69-7.61 (m, 1H), 7.57 (d, J = 7.9, 2H), 7.52 (d, J = 7.1, 1H), 7.28 (t, J = 7.4, 1H), 2.74 (q, J = 7.6, 2H), 2.42 (s, 3H), 1.31 (t, J = 7.6, 3H)<br>MS (ESI) [M + H]⁺ = 264 |
| 73 | ¹H NMR (300 MHz, CDCl₃) δ 8.91 (dd, J = 3.8, 9.0, 1H), 8.11 (d, J = 2.9, 1H), 7.81 (d, J = 8.3, 1H), 7.71 (s, 1H), 7.56 (dd, J = 7.4, 14.1, 2H), 7.51-7.42 (m, 1H), 7.29 (d, J = 7.2, 1H), 2.38 (s, 3H)<br>MS (ESI) [M + H]⁺ = 254 |
| 74 | ¹H NMR (300 MHz, CDCl₃) δ 8.96 (d, J = 8.3, 1H), 8.49 (s, 1H), 7.89 (dd, J = 1.9, 9.0, 1H), 7.82 (d, J = 8.2, 1H), 7.72 (s, 1H), 7.57 (t, J = 8.7, 3H), 7.33 (t, J = 7.4, 1H), 2.37 (s, 3H)<br>MS (ESI) [M + H]⁺ = 304 |
| 75 | ¹H NMR (300 MHz, CDCl₃) δ 7.83 (d, J = 9.0, 1H), 7.69 (dd, J = 1.3, 7.6, 1H), 7.53 (dd, J = 1.2, 8.0, 1H), 7.42 (d, J = 8.9, 2H), 7.15 (t, J = 7.8, 1H), 6.89 (d, J = 8.9, 2H), 6.79 (d, J = 8.9, 2H), 2.97 (s, 6H) |
| 77 | ¹H NMR (300 MHz, CDCl₃) δ 7.83 (d, J = 8.8, 1H), 7.70 (d, J = 7.6, 1H), 7.59 (d, J = 8.6, 2H), 7.52 (d, J = 7.3, 1H), 7.16 (t, J = 7.7, 1H), 6.94 (d, J = 8.4, 3H), 6.86 (d, J = 8.8, 1H), 3.82 (s, 3H)<br>¹³C NMR (75 MHz, CDCl₃) δ 156.40, 155.54, 144.29, 138.09, 132.96, 130.44, 129.99, 126.61, 125.22, 123.29, 122.66, 114.73, 112.16, 55.74.<br>MS (ESI) [M + H]⁺ = 285 |
| 78 | ¹H NMR (300 MHz, CDCl₃) δ 7.80 (t, J = 7.6, 2H), 7.64 (d, J = 8.9, 2H), 7.61-7.55 (m, 1H), 7.33 (t, J = 7.6, 1H), 7.19 (d, J = 8.7, 2H), 2.59 (s, 3H) |
| 79 | ¹H NMR (300 MHz, CDCl₃) δ 7.78 (d, J = 8.4, 1H), 7.76-7.71 (m, 2H), 7.69 (s, 1H), 7.57 (dd, J = 1.1, 8.0, 1H), 7.51 (ddd, J = 1.5, 7.0, 8.4, 1H), 7.29-7.21 (m, 1H), 6.96-6.90 (m, 2H), 3.82 (s, 3H), 2.35 (s, 3H) |
| 80 | ¹H NMR (300 MHz, CDCl₃) δ 7.92 (d, J = 8.9 Hz, 2H), 7.84 (d, J = 8.3 Hz, 1H), 7.78 (s, 1H), 7.62 (d, J = 8.0 Hz, 1H), 7.57 (t, J = 7.7 Hz, 1H), 7.32 (t, J = 7.4 Hz, 1H), 7.24 (d, J = 8.7 Hz, 2H), 6.53 (s, 1H), 2.42 (s, 3H)<br>¹³C NMR (75 MHz, CDCl₃) δ 152.46, 146.25, 143.86, 139.33, 136.83, 128.93, 126.96, 126.71, 124.75, 123.56, 121.88, 120.44, 119.95, 17.77.<br>MS (ESI) [M + H]⁺ = 319 |
| 81 | ¹H NMR (300 MHz, CDCl₃) δ 7.75 (d, J = 8.3, 1H), 7.66 (d, J = 8.5, 3H), 7.55 (d, J = 7.8, 1H), 7.48 (t, J = 7.6, 1H), 7.20 (d, J = 7.2, 1H), 6.80 (d, J = 8.8, 2H), 6.32 (s, 1H), 2.93 (s, 7H), 2.35 (s, 3H) |
| 82 | ¹H NMR (300 MHz, CDCl₃) δ 7.92 (d, J = 8.9, 1H), 7.82-7.70 (m, 2H), 7.66 (d, J = 7.8, 1H), 7.59 (t, J = 7.6, 1H), 7.30 (dd, J = 6.0, 13.5, 1H), 7.14 (s, 1H), 7.11 (s, 1H), 6.84 (d, J = 8.9, 1H), 2.32 (s, 3H)<br>MS (ESI) [M + H]⁺ = 319 |
| 83 | ¹H NMR (300 MHz, CDCl₃) δ 7.93-7.86 (m, 1H), 7.85 (s, 1H), 7.82 (d, J = 8.4, 1H), 7.59 (dd, J = 8.2, 15.5, 2H), 7.44-7.38 (m, 1H), 7.29 (dd, J = 8.3, 16.8, 2H), 6.91 (d, J = 9.0, 1H), 6.87 (d, J = 8.3, 1H)<br>MS (ESI) [M + H]⁺ = 305 |
| 84 | ¹H NMR (300 MHz, CDCl₃) δ 8.67 (d, J = 8.1, 1H), 7.92 (d, J = 8.9, 1H), 7.85 (d, J = 8.4, 1H), 7.63 (d, J = 7.6, 1H), 7.58 (d, J = 7.3, 1H), 7.30 (dd, J = 6.8, 14.8, 3H), 7.02 (t, J = 7.8, 1H), 6.89 (d, J = 8.9, 1H)<br>MS (ESI) [M + H]⁺ = 305 |
| 86 | ¹H NMR (300 MHz, CDCl₃) δ 7.93 (d, J = 8.9, 1H), 7.83 (d, J = 8.3, 1H), 7.70 (d, J = 12.0, 1H), 7.61 (dd, J = 7.9, 18.1, 2H), 7.32 (d, J = 7.9, 1H), 7.31-7.25 (m, 1H), 7.21 (t, J = 6.5, 1H), 6.92 (d, J = 8.9, 1H), 6.79-6.68 (m, 1H)<br>MS (ESI) [M + H]⁺ = 239 |
| 87 | ¹H NMR (300 MHz, CDCl₃) δ 8.27 (s, 1H), 7.76 (d, J = 8.9, 1H), 7.67 (d, J = 7.5, 1H), 7.51 (d, J = 8.2, 1H), 7.45 (d, J = 7.9, 1H), 7.28 (d, J = 8.2, 1H), 7.14 (t, J = 7.8, 1H), 6.86 (d, J = 10.1, 1H), 6.76 (d, J = 8.9, 1H)<br>MS (ESI) [M + H]⁺ = 339 |
| 88 | ¹H NMR (300 MHz, CDCl₃) δ 8.11 (dt, J = 2.1, 12.1, 1H), 7.76 (d, J = 8.9, 1H), 7.66 (dd, J = 1.2, 7.6, 1H), 7.45 (dd, J = 1.1, 8.0, 1H), 7.22 (dd, J = 1.4, 7.2, 2H), 7.18 (d, J = 7.6, 1H), 7.12 (d, J = 7.8, 1H), 6.75 (d, J = 8.9, 1H), 6.69 (d, J = 7.9, 1H)<br>MS (ESI) [M + H]⁺ = 273 |
| 89 | ¹H NMR (300 MHz, DMSO) δ 11.38 (s, 1H), 8.41 (d, J = 9.1, 1H), 7.93 (d, J = 7.8, 1H), 7.80 (dt, J = 8.1, 20.9, 4H), 7.50 (d, J = 7.8, 3H), 7.36 (d, J = 9.3, 1H) |

TABLE II-continued

| Ex | Characterizations |
|---|---|
| 90 | $^1$H NMR (300 MHz, CDCl$_3$) δ 7.84 (d, J = 9.1, 2H), 7.79 (d, J = 8.9, 1H), 7.67 (dd, J = 1.2, 7.6, 1H), 7.48 (dd, J = 1.1, 8.0, 1H), 7.18 (s, 3H), 6.89 (s, 1H), 6.75 (d, J = 8.9, 1H)<br>$^{13}$C NMR (75 MHz, CDCl$_3$) δ 153.88, 144.30, 143.91, 139.00, 138.25, 131.13, 130.13, 126.55, 125.42, 123.45, 122.50, 122.17, 120.49, 119.10, 113.24.<br>MS (ESI) [M + H]$^+$ = 339 |
| 91 | $^1$H NMR (300 MHz, CDCl$_3$) δ 8.74 (s, 1H), 8.54 (s, 1H), 8.46 (d, J = 8.8, 1H), 7.91 (dd, J = 5.5, 14.5, 2H), 7.79 (d, J = 8.9, 1H), 7.67 (d, J = 2.1, 1H), 7.56 (dd, J = 2.3, 8.9, 1H), 7.35 (d, J = 8.9, 1H) |
| 92 | $^1$H NMR (300 MHz, CDCl$_3$) δ 8.67 (d, J = 7.9, 1H), 7.83 (d, J = 8.3, 1H), 7.71 (s, 1H), 7.69-7.61 (m, 1H), 7.55 (dd, J = 7.5, 14.4, 2H), 7.29 (d, J = 7.8, 1H), 6.80 (d, J = 7.4, 1H) |
| 93 | $^1$H NMR (300 MHz, CDCl$_3$) δ 9.21 (dd, J = 1.5, 8.4, 1H), 7.85 (d, J = 8.4, 1H), 7.73 (s, 1H), 7.58 (d, J = 7.8, 1H), 7.53 (dd, J = 1.3, 8.3, 1H), 7.40-7.35 (m, 1H), 7.32 (dd, J = 1.1, 4.6, 1H), 7.31-7.24 (m, 2H), 7.04 (s, 1H), 7.02-6.94 (m, 1H), 2.38 (s, 3H) |
| 94 | $^1$H NMR (300 MHz, CDCl$_3$) δ 8.16 (d, J = 8.7, 1H), 7.83 (d, J = 8.9, 1H), 7.63 (d, J = 7.6, 1H), 7.48 (d, J = 8.0, 1H), 7.13 (t, J = 7.8, 1H), 7.08 (s, 1H), 7.04 (s, 2H), 6.81 (d, J = 8.9, 2H), 2.27 (s, 3H)<br>MS (ESI) [M + H]$^+$ = 353 |
| 95 | $^1$H NMR (300 MHz, MeOD) δ 8.42 (s, 1H), 7.94 (d, J = 7.9, 1H), 7.83 (d, J = 8.1, 1H), 7.78 (d, J = 7.1, 1H), 7.72 (d, J = 8.7, 2H), 7.58 (d, J = 8.2, 3H), 2.60 (s, 3H)<br>MS (ESI) [M + H]$^+$ = 319 |
| 96 | $^1$H NMR (300 MHz, CDCl$_3$) δ 7.79 (d, J = 8.9, 1H), 7.70 (d, J = 8.9, 1H), 7.64 (d, J = 8.9, 2H), 7.59 (d, J = 2.1, 1H), 7.50 (dd, J = 2.3, 8.9, 1H), 7.19 (d, J = 8.6, 2H), 6.85 (d, J = 8.9, 1H)<br>MS (ESI) [M + H]$^+$ = 281 |
| 97 | $^1$H NMR (300 MHz, MeOD) δ 8.11 (d, J = 8.4, 1H), 7.81 (s, 2H), 7.62 (d, J = 8.7, 3H), 7.51 (d, J = 8.3, 2H), 7.12 (s, 1H), 2.77 (s, 3H)<br>MS (ESI) [M + H]$^+$ = 319 |
| 98 | MS (ESI) [M + H]$^+$ = 383-385 |
| 99 | MS (ESI) [M + H]$^+$ = 320 |
| 100 | MS (ESI) [M + H]$^+$ = 316 |
| 101 | $^1$H NMR (300 MHz, CDCl$_3$) δ 7.82 (d, J = 8.9, 1H), 7.70-7.63 (m, 1H), 7.51 (dd, J = 5.3, 7.6, 3H), 7.14 (t, J = 7.8, 1H), 6.91 (d, J = 8.8, 3H), 6.85 (d, J = 9.0, 2H), 3.96 (t, J = 6.5, 2H), 1.84-1.68 (m, 3H), 1.49 (dd, J = 7.4, 15.0, 3H), 0.97 (t, J = 7.4, 3H)<br>MS (ESI) [M + H]$^+$ = 327 |
| 102 | $^1$H NMR (300 MHz, CDCl$_3$) δ 7.89 (d, J = 8.9, 1H), 7.76 (d, J = 8.5, 1H), 7.63 (d, J = 8.1, 1H), 7.59 (s, 1H), 7.54 (d, J = 8.8, 2H), 7.38-7.24 (m, 3H), 7.09 (d, J = 7.4, 1H), 7.02 (dd, J = 2.4, 8.8, 4H), 6.90 (d, J = 8.9, 1H)<br>MS (ESI) [M + H]$^+$ = 313 |
| 103 | MS (ESI) [M + H]$^+$ = 334 |
| 104 | $^1$H NMR (300 MHz, CDCl$_3$) δ 8.49 (d, J = 2.5, 1H), 7.89 (d, J = 8.8, 1H), 7.72 (d, J = 7.6, 1H), 7.63 (dd, J = 2.5, 8.9, 1H), 7.53 (d, J = 8.0, 1H), 7.23 (dd, J = 6.2, 14.0, 2H), 7.04 (s, 1H), 6.81 (d, J = 8.8, 1H)<br>MS (ESI) [M + H]$^+$ = 373 |
| 105 | $^1$H NMR (300 MHz, CDCl$_3$) δ 8.85 (d, J = 2.6, 1H), 8.45 (d, J = 2.3, 1H), 8.01 (d, J = 8.1, 1H), 7.71 (d, J = 7.8, 1H), 7.58 (s, 1H), 7.53 (d, J = 7.6, 1H), 7.51-7.45 (m, 2H), 7.45-7.36 (m, 1H), 6.72-6.62 (m, 2H), 2.48 (s, 3H)<br>13C NMR (75 MHz, CDCl$_3$) δ 157.18, 154.80, 145.42, 143.80, 138.17, 135.04, 128.88, 128.76, 127.17, 127.04, 120.69, 115.22, 106.73, 24.38 |
| 106 | $^1$H NMR (300 MHz, DMSO) δ 10.24 (s, 1H), 9.06 (d, J = 2.3, 1H), 8.65 (d, J = 1.8, 1H), 8.60 (d, J = 8.3, 1H), 8.56 (d, J = 4.5, 1H), 7.97 (dd, J = 8.2, 14.4, 2H), 7.69 (t, J = 6.9, 1H), 7.59 (t, J = 7.4, 1H), 7.08 (dd, J = 4.6, 8.3, 1H)<br>MS (ESI) [M + H]$^+$ = 267 |
| 107 | $^1$H NMR (300 MHz, CDCl$_3$) δ 8.77 (dd, J = 1.5, 4.3, 1H), 8.06 (dd, J = 10.8, 18.4, 3H), 7.93 (d, J = 2.4, 1H), 7.57 (dd, J = 2.4, 9.0, 1H), 7.39 (ddd, J = 3.1, 8.3, 12.5, 3H), 6.93 (d, J = 8.4, 1H), 6.89 (s, 1H), 2.29 (s, 3H) |
| 108 | $^1$H NMR (300 MHz, CDCl$_3$) δ 8.72 (dd, J = 1.6, 4.2, 1H), 8.61 (d, J = 2.4, 1H), 8.11 (d, J = 8.3, 1H), 8.00 (d, J = 9.0, 1H), 7.91 (dd, J = 1.2, 5.0, 1H), 7.69 (dd, J = 2.4, 9.1, 1H), 7.35-7.26 (m, 2H), 7.01 (dd, J = 1.2, 7.9, 1H), 6.77 (dd, J = 5.1, 7.8, 1H), 3.93 (s, 3H) |
| 109 | $^1$H NMR (300 MHz, CDCl$_3$) δ 9.68 (s, 1H), 8.21 (s, 2H), 7.94 (d, J = 8.9, 1H), 7.79 (d, J = 9.2, 1H), 7.67 (d, J = 2.3, 1H), 7.56 (dd, J = 2.3, 8.9, 1H), 7.34 (d, J = 8.9, 1H)<br>MS (ESI) [M + H]$^+$ = 257 |
| 110 | 1H NMR (300 MHz, CDCl$_3$) δ 10.32 (s, 1H), 8.33-8.21 (m, 2H), 8.05 (d, J = 8.9, 1H), 8.00 (dd, J = 1.2, 7.6, 1H), 7.69 (dd, J = 1.1, 7.8, 1H), 7.61 (s, 1H), 7.30-7.22 (m, 3H), 7.16 (d, J = 8.8, 1H).<br>MS (ESI) [M + H]$^+$ = 301-303 |
| 111 | $^1$H NMR (300 MHz, CDCl$_3$) δ 7.82 (d, J = 8.9, 1H), 7.70-7.63 (m, 1H), 7.51 (dd, J = 5.3, 7.6, 3H), 7.14 (t, J = 7.8, 1H), 6.91 (d, J = 8.8, 3H), 6.85 (d, J = 9.0, 2H), 3.96 (t, J = 6.5, 2H), 1.84-1.68 (m, 3H), 1.49 (dd, J = 7.4, 15.0, 3H), 0.97 (t, J = 7.4, 3H) |
| 112 | $^1$H NMR (300 MHz, CDCl$_3$) δ 7.89 (d, J = 8.9, 1H), 7.76 (d, J = 8.5, 1H), 7.63 (d, J = 8.1, 1H), 7.59 (s, 1H), 7.54 (d, J = 8.8, 2H), 7.38-7.24 (m, 3H), 7.09 (d, J = 7.4, 1H), 7.02 (dd, J = 2.4, 8.8, 4H), 6.90 (d, J = 8.9, 1H) |

TABLE II-continued

| Ex | Characterizations |
|---|---|
| | $^{13}$C NMR (75 MHz, DMSO) δ 152.94, 150.19, 142.48, 142.18, 138.20, 137.55, 135.74, 129.71, 126.99, 125.35, 123.84, 114.75.<br>MS (ESI) [M + H]$^+$ = 255 |
| 113 | $^1$H NMR (300 MHz, CDCl$_3$) δ 9.74 (s, 1H), 8.20 (s, 2H), 8.03 (d, J = 8.6, 1H), 7.87 (d, J = 7.6, 1H), 7.80 (s, 1H), 7.70 (d, J = 8.0, 1H), 7.63 (t, J = 7.7, 1H), 7.37 (t, J = 7.4, 1H), 7.30 (d, J = 8.7, 1H) |
| 114 | $^1$H NMR (300 MHz, CDCl$_3$) δ 9.67 (s, 1H), 8.34-8.12 (m, 2H), 7.84 (d, J = 8.0, 2H), 7.70-7.54 (m, 1H), 7.38 (t, J = 7.6, 1H), 7.17 (s, 1H), 2.61 (s, 3H)<br>MS (ESI) [M + H]$^+$ = 237 |
| 115 | $^1$H NMR (300 MHz, CDCl$_3$) δ 10.15 (s, 1H), 8.24-8.12 (m, 2H), 7.79 (s, 1H), 7.71 (s, 1H), 7.55 (t, J = 8.3, 2H), 7.30 (t, J = 7.9, 1H), 2.38 (s, 3H)<br>MS (ESI) [M + H]$^+$ = 237 |
| 116 | MS (ESI) [M + H]$^+$ = 240 |
| 117 | MS (ESI) [M + H]$^+$ = 253 |
| 118 | MS (ESI) [M + H]$^+$ = 222 |
| 119 | MS (ESI) [M + H]$^+$ = 256 |
| 121 | MS (ESI) [M + H]$^+$ = 222 |
| 124 | $^1$H NMR (300 MHz, CDCl$_3$) δ 8.42 (s, 1H), 7.95 (dd, J = 1.3, 8.2, 1H), 7.87-7.78 (m, 3H), 7.70-7.61 (m, 1H), 7.55-7.47 (m, 1H), 7.26 (dd, J = 2.4, 6.5, 3H), 6.90 (s, 1H)<br>MS (ESI) [M + H]$^+$ = 306 |
| 125 | $^1$H NMR (300 MHz, CDCl$_3$) δ 8.42 (s, 1H), 8.03 (d, J = 9.5, 1H), 7.92 (d, J = 8.2, 1H), 7.73 (d, J = 8.2, 1H), 7.61 (t, J = 7.3, 1H), 7.46 (t, J = 7.2, 1H), 7.13 (s, 2H), 6.84 (s, 1H), 2.35 (s, 3H) |
| 126 | $^1$H NMR (300 MHz, CDCl$_3$) δ 8.40 (s, 1H), 8.03 (s, 1H), 7.94 (d, J = 8.2, 1H), 7.84 (d, J = 8.2, 1H), 7.65 (t, J = 7.4, 1H), 7.53 (d, J = 7.1, 1H), 7.48 (d, J = 7.2, 1H), 7.35 (t, J = 8.2, 1H), 7.22 (s, 1H), 6.94 (d, J = 8.1, 1H) |
| 127 | $^1$H NMR (300 MHz, CDCl$_3$) δ 8.85 (dd, J = 1.0, 8.3, 1H), 8.47 (s, 1H), 7.96 (d, J = 8.2, 1H), 7.85 (d, J = 8.3, 1H), 7.72-7.61 (m, 1H), 7.57-7.47 (m, 1H), 7.42-7.36 (m, 1H), 7.33 (d, J = 10.0, 1H), 7.14 (s, 1H), 7.13-7.04 (m, 1H) |
| 128 | $^1$H NMR (300 MHz, CDCl$_3$) δ 9.17 (s, 1H), 8.68 (d, J = 9.1, 1H), 8.64 (d, J = 4.8, 2H), 8.15 (d, J = 9.1, 1H), 7.87 (d, J = 8.4, 1H), 7.76 (d, J = 8.1, 1H), 7.64 (t, J = 7.7, 1H), 7.39 (t, J = 7.5, 1H), 6.87 (t, J = 4.8, 1H)<br>$^{13}$C NMR (75 MHz, CDCl3) δ 158.34, 138.07, 129.85, 127.63, 127.31, 124.34, 114.20, 113.90. |
| 129 | $^1$H NMR (300 MHz, CDCl$_3$) δ 9.14 (s, 1H), 8.73 (d, J = 21.2, 3H), 8.17 (s, 1H), 7.73 (d, J = 20.3, 2H), 7.28 (d, J = 9.6, 2H), 6.91 (s, 1H) |
| 130 | $^1$H NMR (300 MHz, CDCl$_3$) δ 9.05 (s, 1H), 8.64 (d, J = 4.8, 2H), 8.52 (s, 1H), 7.89 (dd, J = 8.5, 14.6, 2H), 7.63 (t, J = 7.5, 1H), 7.41 (t, J = 7.4, 1H), 6.86 (t, J = 4.8, 1H), 2.74 (s, 3H)<br>MS (ESI) [M + H]$^+$ = 237 |
| 132 | $^1$H NMR (300 MHz, CDCl$_3$) δ 8.86 (d, J = 2.6, 1H), 8.70 (d, J = 2.5, 1H), 8.32 (d, J = 1.1, 1H), 8.25-8.21 (m, 1H), 8.10 (d, J = 2.7, 1H), 8.06 (d, J = 8.3, 1H), 7.82 (dd, J = 1.2, 7.9, 1H), 7.66-7.51 (m, 3H), 6.89 (s, 1H) |
| 135 | $^1$H NMR (300 MHz, CDCl$_3$) δ 9.09 (s, 1H), 8.71 (s, 1H), 8.54 (d, J = 8.4, 1H), 8.37 (dd, J = 1.0, 4.9, 1H), 7.96 (d, J = 8.2, 1H), 7.85 (d, J = 8.3, 1H), 7.82-7.74 (m, 1H), 7.66 (t, J = 7.6, 1H), 7.52 (dd, J = 7.0, 8.1, 1H), 7.02 (dd, J = 5.0, 7.2, 1H)<br>MS (ESI) [M + H]$^+$ = 223 |
| 136 | $^1$H NMR (300 MHz, CDCl$_3$) δ 9.02 (s, 1H), 8.70 (s, 1H), 8.30 (s, 1H), 8.20 (d, J = 5.1, 1H), 7.94 (d, J = 8.1, 1H), 7.84 (d, J = 8.2, 1H), 7.64 (t, J = 7.6, 1H), 7.49 (t, J = 8.1, 1H), 6.83 (d, J = 5.0, 1H), 2.43 (s, 3H)<br>$^{13}$C NMR (75 MHz, CDCl$_3$) δ 153.28, 150.20, 148.55, 147.40, 140.93, 139.83, 138.35, 130.44, 129.16, 127.18, 126.28, 119.70, 113.75, 21.87.<br>MS (ESI) [M + H]$^+$ = 237 |
| 137 | $^1$H NMR (300 MHz, DMSO) δ 11.10 (s, 1H), 9.03 (s, 1H), 8.82-8.75 (m, 1H), 8.56 (d, J = 8.9, 1H), 8.24 (dd, J = 2.3, 8.9, 1H), 7.96 (dd, J = 1.2, 8.2, 1H), 7.87 (dd, J = 1.0, 8.3, 1H), 7.79-7.71 (m, 1H), 7.61 (ddd, J = 1.4, 7.0, 8.3, 1H)<br>MS (ESI) [M + H]$^+$ = 248 |
| 138 | $^1$H NMR (300 MHz, CDCl$_3$) δ 8.72 (s, 1H), 8.53 (s, 1H), 8.20 (d, J = 8.3, 1H), 7.93 (d, J = 8.2, 1H), 7.81 (d, J = 8.3, 1H), 7.62 (td, J = 3.4, 8.1, 2H), 7.53-7.43 (m, 1H), 6.83 (d, J = 7.4, 1H), 2.48 (s, 3H)<br>$^{13}$C NMR (75 MHz, CDCl$_3$) δ 156.86, 152.27, 148.40, 140.92, 139.70, 139.00, 138.35, 130.42, 129.13, 127.14, 126.27, 117.76, 110.01, 24.15.<br>MS (ESI) [M + H]$^+$ = 237 |
| 139 | $^1$H NMR (300 MHz, CDCl$_3$) δ 8.53 (s, 1H), 8.20 (d, J = 4.8, 1H), 8.04 (d, J = 8.3, 1H), 7.92 (d, J = 8.4, 1H), 7.87 (s, 1H), 7.79 (t, J = 7.6, 1H), 7.60 (t, J = 7.6, 1H), 6.88 (d, J = 4.7, 1H), 2.46 (s, 3H) |
| 140 | $^1$H NMR (300 MHz, CDCl$_3$) δ 9.93 (s, 1H), 8.19 (s, 1H), 8.05 (d, J = 8.1, 1H), 7.99 (s, 1H), 7.82 (d, J = 8.2, 1H), 7.69 (t, J = 7.6, 1H), 7.59 (t, J = 8.2, 1H), 2.53 (s, 4H) |
| 141 | $^1$H NMR (300 MHz, CDCl$_3$) δ 9.72 (s, 1H), 9.35 (s, 1H), 8.30 (d, J = 5.0, 1H), 8.05 (d, J = 7.7, 1H), 7.87 (d, J = 7.0, 1H), 7.66 (dd, J = 7.4, 16.9, 3H), 6.92 (d, J = 4.9, 1H), 2.58 (s, 3H) |
| 143 | $^1$H NMR (300 MHz, DMSO) δ 8.85 (s, 1H), 8.42 (d, J = 5.3, 1H), 7.96 (d, J = 9.1, 1H), 7.44 (s, 1H), 7.30 (s, 4H), 7.28-7.21 (m, 2H), 6.66 (d, J = 5.3, 1H), 2.99 (s, 6H) |

TABLE II-continued

| Ex | Characterizations |
|---|---|
| | $^{13}$C NMR (75 MHz, DMSO) δ 156.82, 150.25, 149.69, 143.79, 141.71, 125.95, 122.33, 118.88, 117.37, 115.95, 109.39, 104.92, 43.57<br>MS (ESI) [M + H]+ = 348 |
| 144 | MS (ESI) [M + H]$^+$ = 390 |
| 145 | MS (ESI) [M + H]$^+$ = 252 |
| 146 | $^1$H NMR (300 MHz, DMSO) δ 9.34 (s, 1H), 8.59 (d, J = 5.2, 1H), 8.53 (s, 1H), 8.13 (d, J = 5.1, 1H), 7.98 (d, J = 9.0, 1H), 7.66 (d, J = 9.1, 1H), 6.80 (d, J = 5.2, 1H), 6.76 (s, 1H), 6.69 (d, J = 4.9, 1H), 4.00 (s, 3H), 2.26 (s, 3H)<br>$^{13}$C NMR (75 MHz, DMSO) δ 161.31, 155.67, 151.63, 150.25, 147.77, 147.01, 142.97, 121.56, 119.16, 116.61, 114.75, 112.60, 111.41, 98.91, 55.78, 20.66.<br>MS (ESI) [M + H]$^+$ = 266 |
| 147 | MS (ESI) [M + H]$^+$ = 279 |
| 149 | MS (ESI) [M + H]$^+$ = 318 |
| 150 | MS (ESI) [M + H]$^+$ = 280 |
| 151 | $^1$H NMR (300 MHz, CDCl$_3$) δ 8.35 (s, 1H), 8.04 (d, J = 8.3, 1H), 7.82 (d, J = 8.9, 1H), 7.74 (d, J = 8.9, 1H), 7.60 (t, J = 7.8, 2H), 7.50 (dd, J = 2.3, 8.9, 1H), 7.36 (d, J = 8.9, 1H), 6.79 (d, J = 7.4, 1H), 2.75 (q, J = 7.6, 2H), 1.30 (t, J = 7.6, 3H).<br>MS (ESI) [M + H]$^+$ = 284 |
| 152 | $^1$H NMR (300 MHz, CDCl$_3$) δ 8.30 (d, J = 8.5, 1H), 8.08 (s, 1H), 7.90 (d, J = 9.0, 1H), 7.77 (d, J = 8.9, 1H), 7.65 (d, J = 2.2, 1H), 7.55 (td, J = 2.0, 8.8, 2H), 7.39 (d, J = 9.0, 1H), 2.31 (s, 3H).<br>MS (ESI) [M + H]$^+$ = 270 |
| 153 | $^1$H NMR (300 MHz, CDCl$_3$) δ 8.75 (s, 1H), 8.54 (s, 1H), 8.46 (d, J = 8.8, 1H), 7.91 (dd, J = 5.5, 14.5, 2H), 7.79 (d, J = 8.9, 1H), 7.67 (d, J = 2.1, 1H), 7.56 (dd, J = 2.3, 8.9, 1H), 7.35 (d, J = 8.9, 1H).<br>MS (ESI) [M + H]$^+$ = 324 |
| 154 | $^1$H NMR (300 MHz, DMSO) δ 9.08 (s, 1H), 8.12 (d, J = 8.4, 1H), 7.73 (d, J = 8.2, 2H), 7.66 (d, J = 10.0, 1H), 7.53 (s, 1H), 7.25 (s, 1H), 6.82 (s, 1H), 5.10 (s, 2H), 2.16 (s, 4H).<br>MS (ESI) [M + H]$^+$ = 285 |
| 155 | $^1$H NMR (300 MHz, CDCl$_3$) δ 7.68 (d, J = 8.3, 1H), 7.61 (s, 1H), 7.56 (d, J = 11.5, 2H), 7.44 (d, J = 8.3, 1H), 7.38 (d, J = 7.8, 1H), 7.13 (t, J = 7.4, 1H), 6.80 (d, J = 8.7, 2H), 3.85 (t, J = 6.5, 2H), 2.18 (s, 3H), 1.73-1.58 (m, 2H), 1.48-1.31 (m, 2H), 0.88 (t, J = 7.3, 3H)<br>MS (ESI) [M + H]$^+$ = 307 |
| 156 | $^1$H NMR (300 MHz, CDCl$_3$) δ 7.75 (d, J = 9.1, 1H), 7.62 (d, J = 8.9, 1H), 7.58 (d, J = 2.2, 1H), 7.48 (dd, J = 2.4, 8.9, 1H), 7.30 (d, J = 8.9, 2H), 6.86 (d, J = 9.0, 1H), 6.77 (d, J = 8.9, 2H), 6.71 (s, 1H), 2.97 (s, 6H)<br>MS (ESI) [M + H]$^+$ = 298 |
| 157 | $^1$H NMR (300 MHz, CDCl$_3$) δ 7.98 (d, J = 2.6, 1H), 7.89 (d, J = 8.9, 1H), 7.72 (d, J = 7.5, 1H), 7.62 (dd, J = 2.6, 8.8, 1H), 7.55 (d, J = 7.8, 1H), 7.20 (t, J = 7.8, 1H), 6.95 (d, J = 8.9, 1H), 6.84 (d, J = 8.9, 1H), 6.79 (s, 1H), 3.91 (s, 3H)<br>MS (ESI) [M + H]$^+$ = 319 |
| 158 | $^1$H NMR (300 MHz, CDCl$_3$) δ 7.89 (d, J = 9.0, 1H), 7.70 (dd, J = 1.2, 7.5, 1H), 7.56 (dd, J = 1.1, 8.0, 1H), 7.30 (d, J = 8.6, 1H), 7.20 (t, J = 7.8, 1H), 6.71 (t, J = 5.9, 2H), 6.64 (d, J = 9.5, 1H).<br>MS (ESI) [M + H]$^+$ = 354 |
| 159 | $^1$H NMR (300 MHz, CDCl$_3$) δ 8.80 (d, J = 2.6, 1H), 8.37 (d, J = 2.6, 1H), 8.01 (d, J = 8.1, 1H), 7.91 (dd, J = 1.6, 4.9, 1H), 7.78-7.70 (m, 1H), 7.58-7.43 (m, 2H), 7.09 (dd, J = 1.6, 7.6, 1H), 6.84 (dd, J = 4.9, 7.6, 1H), 6.69 (s, 1H), 3.82-3.07 (m, 2H). |
| 160 | $^1$H NMR (300 MHz, CDCl$_3$) δ 9.68-8.90 (m, 1H), 8.77 (s, 1H), 8.35 (s, 1H), 8.14 (d, J = 5.0, 1H), 7.96 (s, 1H), 7.79 (d, J = 8.8, 1H), 7.61 (d, J = 8.5, 1H), 6.88 (d, J = 4.8, 1H), 2.46 (s, 3H) |
| 161 | $^1$H NMR (300 MHz, CDCl$_3$) δ 9.98 (s, 1H), 8.70 (s, 1H), 8.45 (s, 1H), 8.27 (d, J = 5.2, 1H), 7.94 (d, J = 8.1, 1H), 7.84 (d, J = 8.2, 1H), 7.63 (t, J = 7.5, 1H), 7.48 (t, J = 7.5, 1H), 6.87 (d, J = 5.0, 1H), 2.74 (q, J = 7.6, 2H), 1.34 (t, J = 7.6, 3H).<br>MS (ESI) [M + H]$^+$ = 251 |
| 162 | $^1$H NMR (300 MHz, CDCl$_3$) δ 8.73 (s, 1H), 8.70-8.60 (m, 1H), 8.48 (s, 1H), 8.31 (s, 1H), 7.98 (d, J = 8.1, 1H), 7.86 (d, J = 7.9, 1H), 7.68 (t, J = 8.2, 1H), 7.54 (t, J = 8.1, 1H), 2.49 (s, 3H)<br>MS (ESI) [M + H]$^+$ = 315 |
| 163 | $^1$H NMR (300 MHz, CDCl$_3$) δ 8.75 (s, 1H), 8.68 (s, 1H), 8.01 (s, 1H), 7.95 (d, J = 8.2, 1H), 7.84 (d, J = 8.3, 1H), 7.64 (t, J = 8.2, 1H), 7.49 (t, J = 7.0, 1H), 6.69 (s, 1H), 2.45 (s, 3H), 2.38 (s, 3H)<br>MS (ESI) [M + H]$^+$ = 251 |
| 164 | $^1$H NMR (300 MHz, DMSO) δ 10.46 (s, 1H), 9.00 (s, 1H), 8.41 (s, 1H), 8.24 (d, J = 3.0, 1H), 7.90 (d, J = 8.2, 1H), 7.79 (d, J = 8.3, 1H), 7.69 (t, J = 7.0, 1H), 7.52 (t, J = 7.4, 1H), 6.98 (d, J = 4.8, 1H), 5.45 (q, J = 5.6, 1H), 4.58 (d, J = 5.7, 2H).<br>MS (ESI) [M + H]$^+$ = 253 |
| 165 | $^1$H NMR (300 MHz, CDCl$_3$) δ 9.07 (s, 1H), 8.79 (s, 1H), 8.51 (s, 1H), 8.18 (s, 1H), 8.09-8.01 (m, 1H), 7.94 (d, J = 8.4, 1H), 7.81-7.71 (m, 1H), 7.69-7.59 (m, 1H), 2.80 (s, 3H)<br>MS (ESI) [M + H]$^+$ = 282 |
| 166 | $^1$H NMR (300 MHz, CDCl$_3$) δ 8.49 (d, J = 5.0, 1H), 7.77 (d, J = 9.0, 1H), 7.32 (d, J = 2.0, 1H), 7.12 (d, J = 9.0, 2H), 6.99 (dd, J = 2.0, J = 9.0, 1H), 6.82 (d, J = 9.0, 2H), 6.57 (d, J = 5.0, 1H), 5.78 (s, 1H), 3.74 (s, 3H), 3.17 (s, 4H), 2.62 (s, 4H), 2.34 (s, 3H) |

TABLE II-continued

| Ex | Characterizations |
|---|---|
| 167 | MS (ESI) [M + H]+ = 335 |
| 168 | MS (ESI) [M + H]+ = 321 |

The following examples are provided as illustrations and in no way limit the scope of this disclosure.

The following examples illustrate in detail the preparation of some compounds according to the disclosure. The structures of the products obtained have been confirmed by NMR spectra.

EXAMPLES

According to route (A), the compound of formula (III) is placed in a protic solvent such as tert-butanol. The compound of formula (IV) is then added in a 1.1 molar ratio with respect to the compound of formula (III) in presence of $Cs_2CO_3$, in a 2.8 molar ratio, in the presence of Xantphos (4,5-Bis(diphenylphosphino)-9,9-dimethylxanthene), in a 2 mol % amount relative to the total amount of compound of formula (III), and in the presence of $Pd(OAc)_2$, in a 2 mol % amount relative to the total amount of compound of formula (III). The reaction mixture is then heated at 90° C., and stirred during 20 hours, under argon. The reaction mixture is concentrated under reduced pressure and the resulting residue is diluted with ethyl acetate. The organic phase is then washed twice with water, dried on magnesium sulphate, filtered and concentrated under reduced pressure. The residue could then be purified by column chromatography on silica gel to yield pure compounds (6), (43), (77), (80), (90), (112) and (136).

According to route (B), the compound of formula (V) is placed in a protic solvent such as tert-butanol. The compound of formula (VI) is then added in a 1.1 molar ratio with respect to the compound of formula (V) in presence of $Cs_2CO_3$ in a 2.8 molar ratio, in the presence of Xantphos (4,5-Bis(diphenylphosphino)-9,9-dimethylxanthene) in a 2 mol % amount relative to the total amount of compound of formula (V), and in the presence of a $Pd(OAc)_2$, in a 2 mol % amount relative to the total amount of compound of formula (V). The reaction mixture is then heated at 90° C., and stirred during 20 hours, under argon. The reaction mixture is concentrated under reduced pressure and the resulting residue is diluted with ethyl acetate. The organic phase is then washed twice with water, dried on magnesium sulphate, filtered and concentrated under reduced pressure. The residue could then be purified by column chromatography on silica gel to yield pure compound (106).

Example 1: Compound (6) of the Table I

According to route (A), a mixture of 2,8-dichloroquinoline (1.5 g) and 2-amino-4methylpyridine (904 mg), $Pd(OAc)_2$ (34 mg), XantPhos (88 mg) and $Cs_2CO_3$ (7.0 g) in 30 mL of t-BuOH gave compound (6) (1.3 g).

$^1$H NMR (300 MHz, DMSO) δ 10.23 (s, 1H), 8.96 (s, 1H), 8.18 (d, J=8.8, 2H), 7.78 (dd, J=7.7, 13.7, 2H), 7.46 (d, J=8.9, 1H), 7.31 (t, J=7.8, 1H), 6.86 (d, J=4.3, 1H), 2.37 (s, 3H).

$^{13}$C NMR (75 MHz, DMSO) δ 153.63, 153.61, 148.37, 147.32, 142.65, 137.52, 129.68, 129.47, 126.82, 125.06, 123.26, 118.36, 115.10, 113.31, 21.24.

MS (ESI) [M+H]+=270

Example 2: Compound (43) of the Table I

According to route (A), a mixture of 2,8-dichloroquinoline (394 mg) and 2-amino-5fluoropyridine (246 mg), $Pd(OAc)_2$ (9 mg), XantPhos (23 mg) and $Cs_2CO_3$ (1.8 g) in 8 mL of t-BuOH gave compound (43) (320 mg).

$^1$H NMR (300 MHz, DMSO) δ 10.41 (s, 1H), 9.08 (dd, J=4.1, 9.3, 1H), 8.31 (d, J=2.9, 1H), 8.20 (d, J=8.9, 1H), 7.88-7.70 (m, 3H), 7.44 (d, J=8.9, 1H), 7.32 (t, J=7.8, 1H).

$^{13}$C NMR (75 MHz, DMSO) δ 156.30, 153.32, 153.04, 150.17, 142.55, 137.73, 135.06, 134.74, 129.58, 129.49, 126.86, 125.29, 125.14, 125.04, 123.36, 114.91, 113.36.

MS (ESI) [M+H]+=274

Example 3: Compound (77) of the Table I

According to route (A), a mixture of 2,8-dichloroquinoline (985 mg) and p-anisidine (677 mg), $Pd(OAc)_2$ (22 mg), XantPhos (58 mg) and $Cs_2CO_3$ (4.6 g) in 20 mL of t-BuOH gave compound (77) (629 mg).

$^1$H NMR (300 MHz, $CDCl_3$) δ 7.83 (d, J=8.8, 1H), 7.70 (d, J=7.6, 1H), 7.59 (d, J=8.6, 2H), 7.52 (d, J=7.3, 1H), 7.16 (t, J=7.7, 1H), 6.94 (d, J=8.4, 3H), 6.86 (d, J=8.8, 1H), 3.82 (s, 3H).

$^{13}$C NMR (75 MHz, $CDCl_3$) δ 156.40, 155.54, 144.29, 138.09, 132.96, 130.44, 129.99, 126.61, 125.22, 123.29, 122.66, 114.73, 112.16, 55.74.

MS (ESI) [M+H]+=285

Example 4: Compound (80) of the Table I

According to route (A), a mixture of 2-chloro-3methylquinoline (885 mg) and 4-(trifluoromethoxy)aniline (743 µL), $Pd(OAc)_2$ (22 mg), XantPhos (58 mg) and $Cs_2CO_3$ (4.6 g) in 20 mL of t-BuOH gave compound (80) (1.3 g).

$^1$H NMR (300 MHz, $CDCl_3$) δ 7.92 (d, J=8.9 Hz, 2H), 7.84 (d, J=8.3 Hz, 1H), 7.78 (s, 1H), 7.62 (d, J=8.0 Hz, 1H), 7.57 (t, J=7.7 Hz, 1H), 7.32 (t, J=7.4 Hz, 1H), 7.24 (d, J=8.7 Hz, 2H), 6.53 (s, 1H), 2.42 (s, 3H).

$^{13}$C NMR (75 MHz, $CDCl_3$) δ 152.46, 146.25, 143.86, 139.33, 136.83, 128.93, 126.96, 126.71, 124.75, 123.56, 121.88, 120.44, 119.95, 17.77.

MS (ESI) [M+H]+=319

Example 5: Compound (90) of the Table I

According to route (A), a mixture of 2,8-dichloroquinoline (984 mg) and 4-(trifluoromethoxy)aniline (743 µL), $Pd(OAc)_2$ (22 mg), XantPhos (58 mg) and $Cs_2CO_3$ (4.6 g) in 20 mL of t-BuOH gave compound (90) (1.1 g).

$^1$H NMR (300 MHz, $CDCl_3$) δ 7.84 (d, J=9.1, 2H), 7.79 (d, J=8.9, 1H), 7.67 (dd, J=1.2, 7.6, 1H), 7.48 (dd, J=1.1, 8.0, 1H), 7.18 (s, 3H), 6.89 (s, 1H), 6.75 (d, J=8.9, 1H).

$^{13}$C NMR (75 MHz, $CDCl_3$) δ 153.88, 144.30, 143.91, 139.00, 138.25, 131.13, 130.13, 126.55, 125.42, 123.45, 122.50, 122.17, 120.49, 119.10, 113.24.

MS (ESI) [M+H]+=339

Example 6: Compound (106) of the Table I

According to route (B), a mixture of 3-aminoquinoline (316 mg) and 2-chloro-3nitropyridine (315 mg), $Pd(OAc)_2$ (22 mg), XantPhos (58 mg) and $Cs_2CO_3$ (4.6 g) in 20 mL of t-BuOH gave compound (106) (374.1 mg).

¹H NMR (300 MHz, DMSO) δ 10.24 (s, 1H), 9.06 (d, J=2.3, 1H), 8.65 (d, J=1.8, 1H), 8.60 (d, J=8.3, 1H), 8.56 (d, J=4.5, 1H), 7.97 (dd, J=8.2, 14.4, 2H), 7.69 (t, J=6.9, 1H), 7.59 (t, J=7.4, 1H), 7.08 (dd, J=4.6, 8.3, 1H).
MS (ESI) [M+H]⁺=267

Example 7: Compound (112) of the Table I

According to route (A), a mixture of 2,8-dichloroquinoline (958 mg) and aminopyrazine (522 mg), Pd(OAc)₂ (22 mg), XantPhos (58 mg) and Cs₂CO₃ (4.6 g) in 20 mL of t-BuOH gave compound (112) (728 mg).
¹H NMR (300 MHz, DMSO) δ 10.58 (s, 1H), 10.26 (s, 1H), 8.36 (s, 1H), 8.27 (s, 2H), 7.91-7.74 (m, 2H), 7.50 (d, J=8.8, 1H), 7.37 (t, J=7.6, 1H).
¹³C NMR (75 MHz, DMSO) δ 152.94, 150.19, 142.48, 142.18, 138.20, 137.55, 135.74, 129.71, 126.99, 125.35, 123.84, 114.75.
MS (ESI) [M+H]⁺=255

Example 7: Compound (136) of the Table I

According to route (A), a mixture of 2-chloroquinoxaline (82.0 mg) and 2-amino-4methylpyridine (59.4 mg), Pd(OAc)₂ (2.2 mg), XantPhos (5.8 mg) and Cs₂CO₃ (456 mg) in 2 mL of t-BuOH gave compound (136) (35.4 mg).
¹H NMR (300 MHz, CDCl₃) δ 9.02 (s, 1H), 8.70 (s, 1H), 8.30 (s, 1H), 8.20 (d, J=5.1, 1H), 7.94 (d, J=8.1, 1H), 7.84 (d, J=8.2, 1H), 7.64 (t, J=7.6, 1H), 7.49 (t, J=8.1, 1H), 6.83 (d, J=5.0, 1H), 2.43 (s, 3H).
¹³C NMR (75 MHz, CDCl₃) δ 153.28, 150.20, 148.55, 147.40, 140.93, 139.83, 138.35, 130.44, 129.16, 127.18, 126.28, 119.70, 113.75, 21.87.
MS (ESI) [M+H]⁺=237

Example 8: Method for Synthesizing the Compounds of the Present Disclosure

Typical Procedure for Pd-Catalyzed Aminations
To a solution of halogeno compound (0.5 mmol, 1 equiv) in tert-butanol (2 mL) were added the amino moiety (0.55 mmol, 1.1 equiv), Cs₂CO₃ (456 mg, 1.4 mmol, 2.8 equiv), Xantphos (4,5-Bis(diphenylphosphino)-9,9-dimethylxanthene) (5.8 mg, 0.01 mmol, 2 mol %), Pd(OAc)₂ (2.2 mg, 0.01 mmol, 2 mol %). The reaction mixture was heated at 90° C. and stirred for 20 h under argon. The reaction mixture was concentrated under reduced pressure. The residue was purified by column chromatography on silica gel to yield pure compounds.

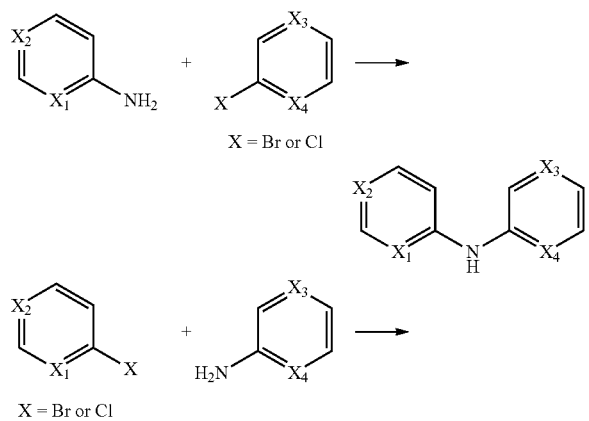

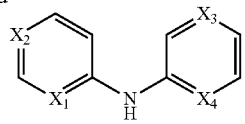

For example this procedure permitted to synthetize the following compounds:

Isoquinolin-5-yl-(3-methoxy-pyridin-2-yl)-amine

¹H NMR (300 MHz, CDCl₃) δ 9.24 (s, 1H), 8.66 (dd, J=1.7, 6.8, 1H), 8.55 (d, J=6.0, 1H), 7.85 (d, J=5.0, 1H), 7.76 (d, J=6.0, 1H), 7.69-7.58 (m, 2H), 7.53 (s, 1H), 7.06 (d, J=7.7, 1H), 6.78 (dd, J=5.1, 7.8, 1H), 3.99 (s, 3H).
¹³C NMR (75 MHz, CDCl₃) δ 153.23, 146.60, 142.97, 142.79, 138.53, 134.82, 129.53, 129.13, 127.95, 121.66, 119.82, 115.18, 115.05, 114.09, 100.15, 55.80.

(8-Chloro-quinolin-2-yl)-(4-methyl-pyridin-2-yl)-amine: (6) of the table I

¹H NMR (300 MHz, CDCl3) δ 8.82 (s, 1H), 8.17 (d, J=5.1, 1H), 8.09 (s, 1H), 7.98 (d, J=8.9, 1H), 7.76 (dd, J=1.2, 7.6, 1H), 7.61 (dd, J=1.0, 8.0, 1H), 7.26 (t, J=7.8, 2H), 7.15 (d, J=8.7, 1H), 6.83 (d, J=5.0, 1H), 2.46 (s, 3H).
¹³C NMR (75 MHz, CDCl3) δ 153.52, 153.14, 149.90, 147.43, 143.68, 138.08, 131.37, 129.98, 126.56, 125.58, 123.58, 119.17, 114.52, 114.02, 21.84.

(3-Methoxy-pyridin-2-yl)-quinolin-3-yl-amine: (10) of the table I

¹H NMR (300 MHz, DMSO) δ 9.17 (d, J=2.5, 1H), 8.97 (d, J=2.4, 1H), 8.79 (s, 1H), 7.94-7.79 (m, 3H), 7.58-7.46 (m, 2H), 7.31 (d, J=7.9, 1H), 6.88 (dd, J=5.0, 7.9, 1H), 3.94 (s, 3H).

Pharmalogical Data
The compounds of the disclosure have been the subject of pharmacological tests which have demonstrated their relevance as active substances in therapy and in particular for preventing or treating the infection of an individual, preferably a human, by a retrovirus and/or for preventing, inhibiting or treating a disease caused by retroviruses.

Example 9: Development of IDC16 Derivative Compounds

The inventors have shown that compound IDC16 (BAKKOUR et al., cited above, 2007) interacts functionally with the SF2/ASF complex and thus contributes to blocking alternative splicing during HIV replication, leading to the termination of the production of Tat protein.
Accordingly, the family of polycyclic indoles, to which compound IDC16 belongs, is known to exhibit the properties of DNA intercalating agents. Such compounds thus present a risk in terms of undesirable side effects.
The inventors thus sought to develop novel molecules exhibiting activity comparable to IDC16, in terms of activity inhibiting HIV splicing, but while not exhibiting the characteristics of DNA intercalating agents.
In their initial hypothesis, the inventors considered that the two polar heterocycles at the two ends of compound IDC16 were associated with its activity and that the two median rings were of less importance.

Based on this hypothesis, the inventors considered that:
the nitrogen of the indoline and of the D ring of IDC16 might act as acceptors of hydrogen bonds;
the N-methylated 4-pyridinone motif might be preserved in the analogues;
the flat tetracyclic geometry was not optimal and it might be wise to replace the B and C rings by other motifs to limit DNA intercalating properties.

Example 10: Inhibition of HTLV-1

The Human T-lymphotropic virus (HTLV) is a human RNA retrovirus that is known to cause a type of cancer. HLTV undergoes splicing to replicate.

To determine whether the compounds described above could act as HTLV inhibitors, a screen was performed on HUT102 (HTLV-1 chronically infected) cells.

Cells were plated at a density of 150 000 cells per well in 96 wells plates and treated daily with 10 µM of compounds for three days.

Cells were then harvested and an aliquot was used for cytotoxicity evaluation with Cell Titer (Promega).

The remaining cells was washed in phosphate buffer saline (PBS) and lysed for protein quantification with Bradford Assay (Sigma).

Then, HTLV Tax-1 protein expression was evaluated from 30 µg of total proteins by western blotting analysis.

Tax-1 expression was normalised by tubulin expression and related to control (DMSO treated) cells. Each compound was tested in triplicate.

Using the above described assay, compound 166 reduced Tax-1 expression by 80% when compared to control, suggesting that compound 166 has effective HTLV-1 inhibition capacity.

In certain aspects, the compounds described above can be included in pharmaceutical compositions. For example, these pharmaceutical compositions may comprise at least one compound of formula (Ib) or (Ie) or anyone of compounds (8), (75), (77)-(84), (86)-(104), (109)-(117), (155)-(158) and their pharmaceutically acceptable salts, such as hydrobromide, tartrate, citrate, trifluoroacetate, ascorbate, hydrochloride, tartrate, triflate, maleate, mesylate, formate, acetate and fumarate and, optionally, a pharmaceutically acceptable support.

As examples of pharmaceutically acceptable supports, the composition can include emulsions, microemulsions, oil in water emulsions, anhydrous lipids and water in oil emulsions or other types of emulsions.

The compositions described herein can further include one or more additives such as diluents, excipients, stabilizers and preservatives. Such additives are well known to those skilled in the art and are described notably in "*Ullmann's Encyclopedia of Industrial Chemistry*, 6$^{th}$ Ed." (various editors, 1989-1998, Marcel Dekker) and in "*Pharmaceutical Dosage Forms and Drug Delivery Systems*" (ANSEL et al., 1994, WILLIAMS & WILKINS).

The aforementioned excipients are selected according to the dosage form and the desired mode of administration.

In this context they can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

Still a further object consists of the use of at least one compound of formula (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, and compounds (1) to (168) as defined above, or one of its pharmaceutically acceptable salts according to the present disclosure in preparing a drug to treat, in a subject, a disease resulting from at least one splicing anomaly.

Therefore, the present disclosure relates to a compound of formula (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, and compounds (1) to (168) as defined above, or one of its pharmaceutically acceptable salts according to the present disclosure for preparing a drug to treat, in a subject, a disease resulting from at least one splicing anomaly.

As used in the present application, the term "subject" refers to a mammal such as a rodent, cat, dog, primate or human, preferably said subject is a human.

Preferably, the compounds described herein have the ability to inhibit pre-messenger RNA splicing processes that are either constitutive or, more specifically, dependent on regulating sequences known as an ESE (exonic splicing enhancer), ISE (intronic splicing enhancer), ESS (exonic splicing silencer) and ISS (intronic splicing silencer).

In a particularly preferred way, splicing processes are either constitutive and/or or dependent on ESE regulating sequences.

Preferably, the present disclosure relates to the use of the at least one compound of formula (I), (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, or one of its pharmaceutically acceptable salts according to the present disclosure, and more particularly of formula (Ia), (Ib), (Ic), (Ie) and (Io) as described above for preparing a drug to treat, in a subject, the infection by a retrovirus or a disease caused by retroviruses described herein.

Therefore, the present disclosure relates to a one of said compounds, and more particularly to a compound (1) to (168) or one of its acceptable salts for treating the infection by a retrovirus or a disease caused by retroviruses described herein. Another object of the disclosure relates to a therapeutic method for treating a subject for a genetic disease resulting from splicing anomalies comprising the administration of a therapeutically effective quantity of a compound of formula (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, more particularly of formula (Ia), (Ib), (Ic), (Ie) and (Io) as described above, and even more particularly of at least one compound (1) to (168) or one of its acceptable salts.

A "therapeutically effective quantity" means a quantity that induces inhibition of the splicing of the pre-mRNAs of interest. Those skilled in the art will be able to determine said therapeutically effective quantity based on their general knowledge and on the methods described in the examples.

The compounds can be administered by any mode of administration such as, for example, by intramuscular, intravenous or oral route, etc.

In one embodiment according to the disclosure, said composition further includes an excipient making it possible to formulate the inventive compounds in such a way that said composition is provided in solid or liquid form to be prepared and administered by intravenous route.

The inventive compounds preferably will be administered by intravenous route at a concentration of 80-100 mg/m$^2$. The concentration will be chosen by those skilled in the art according to the organ or tissue to be treated, the state of advancement of the disease and the targeting mode used.

The invention claimed is:
1. A method for inhibiting RNA splicing of HTLV-1 comprising administering a compound to a subject in need thereof, at least one compound of formula (I):

(I)

wherein:

is an aromatic ring wherein V is C or N and when V is N, V is in an ortho, meta or para position with respect to Z such that the ring respectively forms a pyridazine, a pyrimidine or a pyrazine,
R independently represents a hydrogen atom, a halogen atom or a group chosen among a —CN group, a hydroxyl group, a —COOR$_1$ group, a ($C_1$-$C_3$)fluoroalkyl group, a ($C_1$-$C_3$)fluoroalkoxy group, a —NO$_2$ group, a —NR$_1$R$_2$ group, a ($C_1$-$C_4$)alkoxy group, a phenoxy group and a ($C_1$-$C_3$)alkyl group, said alkyl group being optionally mono-substituted by a hydroxyl group,
R$_1$ and R$_2$ are independently a hydrogen atom or a ($C_1$-$C_3$)alkyl group,
n is 1, 2 or 3,
n' is 1 or 2,
R' is a hydrogen atom, a halogen atom or a group chosen among a ($C_1$-$C_3$)alkyl group, a hydroxyl group, a —COOR$_1$ group, a —NO$_2$ group, a —NR$_1$R$_2$ group, a morpholinyl or a morpholino group, a N-methylpiperazinyl group, a ($C_1$-$C_3$)fluoroalkyl group, a ($C_1$-$C_4$) alkoxy group and a —CN group,
R" is a hydrogen atom or a ($C_1$-$C_4$)alkyl group,
Z is N or C,
Y is N or C,
X is N or C,
W is N or C,
T is N or C,
U is N or C,
and wherein at most four of the groups V, T, U, Z, Y, X and W are N,
and at least one of the groups T, U, Y, X and W is N,
or a pharmaceutically acceptable salt thereof.
2. The method of claim 1, wherein
Z is N, V is C, Y is N, X is C, T is C, U is C and W is C,
Z is C, V is C, Y is N, X is C, T is C, U is C and W is C,
Z is N, V is C, Y is C, X is N, T is C, U is C and W is C,
Z is N, V is C, Y is C, X is C, T is C, U is C and W is N,
Z is N, V is N and is in the para position with respect to Z, Y is N, X is C, T is C, U is C and W is C
Z is C, V is N and is in the para position with respect to Z, Y is C, X is N, T is C, U is C and W is C,
Z is C, V is N and is in the meta position with respect to Z and is in a para position with respect to the bond linked to NR", Y is N, X is C, T is C, U is C and W is C,
Z is C, V is N and is in the meta position with respect to Z and is in the para position with respect to the bond linked to NR", Y is C, X is N, T is C, U is C and W is C,
Z is C, V is C, Y is C, X is N, T is C, U is C and W is C,
Z is C, V is C, Y is N, X is N, T is C, U is C and W is C,
Z is N, V is N and is in the meta position with respect to Z and in an ortho position with respect to the bond linked to NR", Y is N, X is C, T is C, U is C and W is C,
Z is N, V is N and is in the para position with respect to Z, Y is C, X is C, T is C, U is C and W is N,
Z is N, V is N and is in the para position with respect to Z, Y is C, X is N, T is C, U is C and W is C,
Z is N, V is C, Y is N, X is N, T is C, U is C and W is C,
Z is N, V is N and is in the meta position with respect to Z and is in the ortho position with respect to the bond linked to NR", Y is N, X is N, T is C, U is C and W is C,
Z is C, V is C, Y is C, X is C, T is N, U is C and W is C,
Z is N, V is C, Y is C, X is C, T is N, U is C and W is C, or
Z is N, V is C, Y is C, X is C, T is C, U is N and W is C.
3. The method of claim 1, wherein
Z is N, V is C, Y is N, X is C, T is C, U is C and W is C,
Z is C, V is C, Y is N, X is C, T is C, U is C and W is C,
Z is N, V is C, Y is C, X is N, T is C, U is C and W is C,
Z is N, V is N and is in the para position with respect to Z, Y is N, X is C, T is C, U is C and W is C, or
Z is N, V is C, Y is N, X is N, T is C, U is C and W is C.
4. The method of claim 1, wherein the compound of formula (I) is selected from the group consisting of:

(1)

(Ia)

wherein:
R independently represents a hydrogen atom, a halogen atom or a group chosen among a ($C_1$-$C_3$)alkyl group, a —CN group, a hydroxyl group, a —COOR$_1$ group, a ($C_1$-$C_3$)fluoroalkyl group, a —NO$_2$ group, a —NR$_1$R$_2$ group and a ($C_1$-$C_3$)alkoxy group,
R' is a hydrogen atom, a halogen atom or a group chosen among a ($C_1$-$C_3$)alkyl group, a —NO$_2$ group, a ($C_1$-$C_3$)alkoxy group and a —NR$_1$R$_2$ group,
R$_1$ and R$_2$ are a hydrogen atom or a ($C_1$-$C_3$)alkyl group, (2)

(Ib)

wherein:
R independently represents a hydrogen atom, a halogen atom or a group chosen among a ($C_1$-$C_3$)alkyl group, a —NR₁R₂ group, a (C₁-C₃)fluoroalkoxy group, a —NO₂ group, a phenoxy group and a (C₁-C₄)alkoxy group, R₁ and R₂ are independently a hydrogen atom or a (C₁-C₃)alkyl group, R' is a hydrogen atom, a halogen atom or a group chosen among a (C₁-C₃)alkyl group and a (C₁-C₄)alkoxy group, (3)

(Ic)

wherein:

R independently represents a hydrogen atom or a group chosen among a (C₁-C₃)alkyl group, a (C₁-C₃)fluoroalkyl group, a —NR₁R₂ group, a —COOR₁ group, a —NO₂ group and a (C₁-C₃)alkoxy group, R' is a hydrogen atom, R₁ and R₂ are independently a hydrogen atom or a (C₁-C₃)alkyl group, (4)

(Id)

wherein:

R independently represents a hydrogen atom or a group chosen among a (C₁-C₃)alkyl group, a (C₁-C₃)fluoroalkyl group and a (C₁-C₃)alkoxy group, R' is a hydrogen atom, (5)

(Ie)

wherein:

R is a hydrogen atom,

R' is a hydrogen atom, a halogen atom or a group chosen among a (C₁-C₃)alkyl group and a (C₁-C₃)alkoxy group, (6)

(If)

wherein:

R is a hydrogen atom,

R' is a hydrogen atom, (7)

(Ig)

wherein:

R is a hydrogen atom,

R' is a hydrogen atom or a halogen atom, (8)

(Ih)

wherein:

R is a hydrogen atom,

R' is a hydrogen atom, (9)

(Ii)

wherein:

R independently represents a hydrogen atom or a group chosen among a (C₁-C₃)fluoroalkoxy group and a (C₁-C₃)alkoxy group, R' is a hydrogen atom, (10)

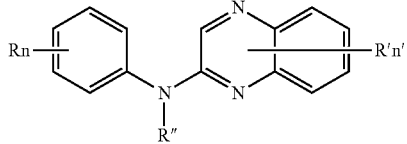
(Ij)

wherein:
R independently represents a hydrogen atom or a group chosen among a $(C_1-C_3)$fluoroalkoxy group and a $(C_1-C_3)$alkyl group,
R' is a hydrogen atom, (11)

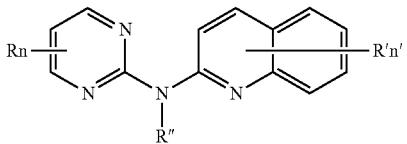
(Ik)

wherein:
R is a hydrogen atom,
R' is a hydrogen atom, a halogen atom or a $(C_1-C_3)$alkyl group, (12)

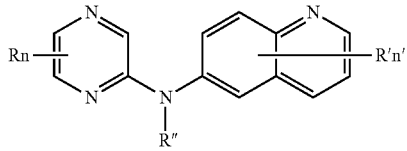
(Il)

wherein:
R is a hydrogen atom,
R' is a hydrogen atom, (13)

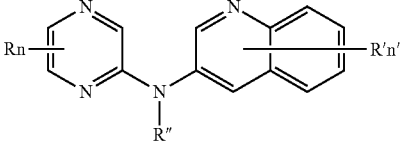
(Im)

wherein:
R is a hydrogen atom,
R' is a hydrogen atom, (14)

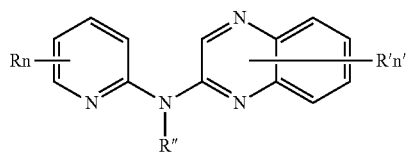
(Io)

wherein:
R independently represents a hydrogen atom, a halogen atom or a group chosen among, a —NO$_2$ group, a —CN group and a $(C_1-C_3)$alkyl group, said alkyl being optionally mono-substituted by a hydroxyl group,
R' is a hydrogen atom, a halogen atom or a $(C_1-C_3)$ fluoroalkyl group, (15)

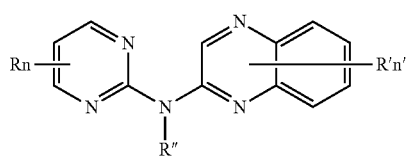
(Ip)

wherein:
R is a hydrogen atom,
R' is a hydrogen atom, (16)

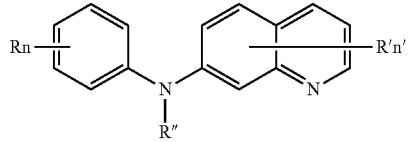
(Iq)

wherein:
R independently represents a hydrogen atom, a $(C_1-C_3)$ alkoxy group or a $(C_1-C_3)$fluoroalkoxy group,
R' is a hydrogen atom or a group chosen among a —NR$_1$R$_2$ group, a N-methylpiperazinyl group, a $(C_1-C_3)$alkoxy group and a morpholino group,
R$_1$ and R$_2$ are independently a hydrogen atom or a $(C_1-C_3)$alkyl group, (17)

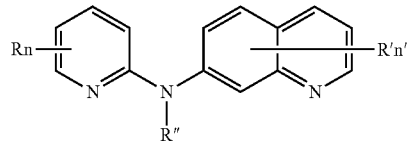
(Ir)

wherein:
R independently represents a hydrogen atom or a $(C_1-C_3)$ alkyl group,
R' is a hydrogen atom or a group chosen among a —NR$_1$R$_2$ group, a morpholino group and a $(C_1-C_3)$ alkoxy group, $R_1$ and $R_2$ are independently a hydrogen atom or a $(C_1-C_3)$alkyl group, (18)

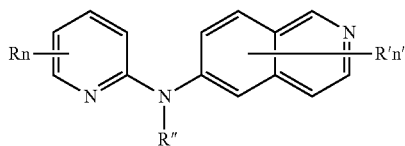
(Iee)

wherein:
R independently represents a hydrogen atom, a $(C_1-C_3)$ alkyl group or a $(C_1-C_3)$fluoroalkyl group,
R' is a hydrogen atom or a $(C_1-C_3)$alkyl group,
and (19) a pharmaceutically acceptable salt thereof.

5. The method of claim 1, wherein the compound of formula (I) is selected from the group consisting of:

(1)

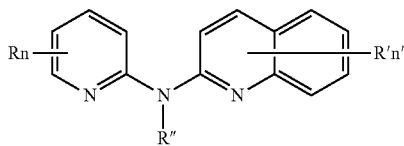
(Ia)

wherein:
R independently represents a hydrogen atom, a halogen atom or a group chosen among a $(C_1-C_3)$alkyl group, a $(C_1-C_3)$fluoroalkyl group, a hydroxyl group, a —CN group, a —COOH group and a $(C_1-C_3)$alkoxy group,
R' is a hydrogen atom, a halogen atom, a —NO$_2$ group or a $(C_1-C_3)$alkyl group, (2)

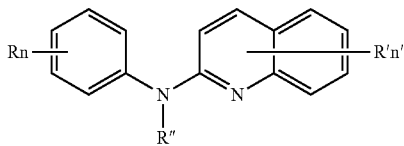
(Ib)

wherein:
R independently represents a hydrogen atom, a halogen atom, a group chosen among a $(C_1-C_3)$alkyl group, a —NR$_1$R$_2$ group, a $(C_1-C_3)$alkoxy group and a $(C_1-C_3)$ fluoroalkoxy group,
$R_1$ and $R_2$ are independently a hydrogen atom or a $(C_1-C_3)$alkyl group,
R' is a hydrogen atom, halogen atom or a $(C_1-C_3)$alkyl group, (3)

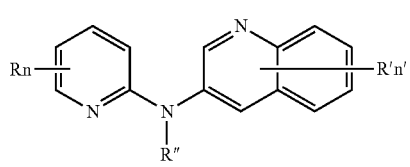
(Ic)

wherein:
R independently represents a hydrogen atom or a group chosen among a $(C_1-C_3)$fluoroalkyl group, a —NO$_2$ group and a $(C_1-C_3)$alkoxy group,
R' is a hydrogen atom, (4)

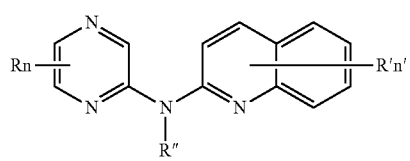
(Ie)

wherein:
R is a hydrogen atom,
R' is a hydrogen atom or a halogen atom, (5)

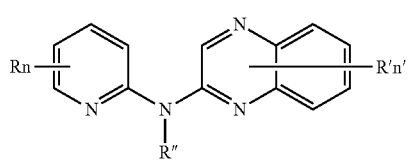
(Io)

wherein:
R independently represents a hydrogen atom, a halogen atom or a group chosen among a $(C_1-C_3)$alkyl group and a —NO$_2$ group,
n is 1, 2 or 3,
R' is a hydrogen atom or a $(C_1-C_3)$fluoroalkyl group,
and (6) a pharmaceutically acceptable salt thereof.

6. The method of claim 1, wherein the at least one compound is selected from the group consisting of
(1) (8-Chloro-quinolin-2-yl)-pyridin-2-yl-amine
(2) 2-(Quinolin-2-ylamino)-isonicotinic acid
(3) (4-Methyl-pyridin-2-yl)-quinolin-2-yl-amine
(4) Pyridin-2-yl-quinolin-2-yl-amine
(5) 2-(8-Chloro-quinolin-2-ylamino)-isonicotinic acid
(6) (8-Chloro-quinolin-2-yl)-(4-methyl-pyridin-2-yl)-amine
(7) 6-(Quinolin-2-ylamino)-nicotinonitrile
(8) Quinolin-2-yl-(4-trifluoromethoxy-phenyl)-amine
(9) Pyridin-2-yl-quinolin-3-yl-amine
(10) (3-Methoxy-pyridin-2-yl)-quinolin-3-yl-amine
(11) Quinolin-3-yl-(5-trifluoromethyl-pyridin-2-yl)-amine
(12) (5-Nitro-pyridin-2-yl)-quinolin-3-yl-amine
(13) (5-Methyl-pyridin-2-yl)-quinolin-3-yl-amine
(14) 2-(Quinolin-3-ylamino)-isonicotinic acid

(15) Quinolin-6-yl-(5-trifluoromethyl-pyridin-2-yl)-amine
(16) (6-Methyl-pyridin-2-yl)-quinolin-6-yl-amine
(17) N-(6-methylpyridin-2-yl)quinolin-2-amine
(18) 8-chloro-N-(6-methylpyridin-2-yl)quinolin-2-amine
(19) 4-methyl-N-(pyridin-2-yl)quinolin-2-amine
(20) 4-methyl-N-(4-methylpyridin-2-yl)quinolin-2-amine
(21) 3-methyl-N-(4-methylpyridin-2-yl)quinolin-2-amine
(22) 3-methyl-N-(pyridin-2-yl)quinolin-2-amine
(23) 6-((4-methylquinolin-2-yl)amino)nicotinonitrile
(24) 6-((3-methylquinolin-2-yl)amino)nicotinonitrile
(25) 6-chloro-N-(4-methylpyridin-2-yl)quinolin-2-amine
(26) 6-chloro-N-(6-methylpyridin-2-yl)quinolin-2-amine
(27) 4-methyl-N-(5-nitropyridin-2-yl)quinolin-2-amine
(28) N-(3-nitropyridin-2-yl)quinolin-2-amine
(29) 8-chloro-N-(3-nitropyridin-2-yl)quinolin-2-amine
(30) 2-((4-methylquinolin-2-yl)amino)nicotinonitrile
(31) N-(3-methylpyridin-2-yl)quinolin-2-amine
(32) N-(5-methylpyridin-2-yl)quinolin-2-amine
(33) 2-(quinolin-2-ylamino)isonicotinonitrile
(34) N-(5-(trifluoromethyl)pyridin-2-yl)quinolin-2-amine
(35) 8-chloro-N-(3-methylpyridin-2-yl)quinolin-2-amine
(36) 8-chloro-N-(5-methylpyridin-2-yl)quinolin-2-amine
(37) 8-chloro-N-(5-(trifluoromethyl)pyridin-2-yl)quinolin-2-amine
(38) N-(3-methoxypyridin-2-yl)quinolin-2-amine
(39) N-(5-nitropyridin-2-yl)quinolin-2-amine
(40) 6-((8-chloroquinolin-2-yl)amino)nicotinonitrile
(41) N-(5-fluoropyridin-2-yl)quinolin-2-amine
(42) N-(6-(trifluoromethyl)pyridin-2-yl)quinolin-2-amine
(43) 8-chloro-N-(5-fluoropyridin-2-yl)quinolin-2-amine
(44) 2-((8-chloroquinolin-2-yl)amino)nicotinic acid
(45) 4-methyl-N-(6-methylpyridin-2-yl)quinolin-2-amine
(46) 3-methyl-N-(6-methylpyridin-2-yl)quinolin-2-amine
(47) 5-cyano-2-(quinolin-2-ylamino)pyridin-1-ium chloride
(48) 2-((8-chloroquinolin-2-yl)amino)-4-methylpyridin-1-ium chloride
(49) 8-chloro-N-(4-ethylpyridin-2-yl)quinolin-2-amine
(50) 8-chloro-N-(6-ethylpyridin-2-yl)quinolin-2-amine
(51) 8-chloro-N-(4,6-dimethylpyridin-2-yl)quinolin-2-amine
(52) 6-((8-chloroquinolin-2-yl)amino)-2-methylnicotinonitrile
(53) 8-chloro-N-(4-chloropyridin-2-yl)quinolin-2-amine
(54) 8-methyl-N-(4-methylpyridin-2-yl)quinolin-2-amine
(55) N-(5-bromo-4-methylpyridin-2-yl)-8-chloroquinolin-2-amine
(56) 8-chloro-N-(3-ethyl-6-methylpyridin-2-yl)quinolin-2-amine
(57) 8-fluoro-N-(4-methylpyridin-2-yl)quinolin-2-amine
(58) 8-bromo-N-(4-methylpyridin-2-yl)quinolin-2-amine
(59) methyl 6-(quinolin-2-ylamino)nicotinate
(60) methyl 6-[(8-chloroquinolin-2-yl)amino]pyridine-3-carboxylate
(61) methyl 6-[(3-methylquinolin-2-yl)amino]pyridine-3-carboxylate
(62) methyl 2-[(8-chloroquinolin-2-yl)amino]pyridine-3-carboxylate
(63) 8-methoxy-N-(4-methylpyridin-2-yl)quinolin-2-amine
(64) N-(4-methylpyridin-2-yl)-5-nitroquinolin-2-amine
(65) 2-N-(4-methylpyridin-2-yl)quinoline-2,8-diamine
(66) N-(4-methylpyridin-2-yl)-5-aminoquinolin-2-amine
(67) methyl 6-[(4-methylquinolin-2-yl)amino]pyridine-3-carboxylate
(68) 8-chloro-N-[4-(trifluoromethyl)pyridin-2-yl]quinolin-2-amine
(69) 2-[(8-chloroquinolin-2-yl)amino]pyridin-3-ol
(70) 8-chloro-N-[6-(trifluoromethyl)pyridin-2-yl]quinolin-2-amine
(71) 6-chloro-N-(5-fluoropyridin-2-yl)quinolin-2-amine
(72) N-(6-ethylpyridin-2-yl)-3-methylquinolin-2-amine
(73) N-(5-fluoropyridin-2-yl)-3-methylquinolin-2-amine
(74) 3-methyl-N-[5-(trifluoromethyl)pyridin-2-yl]quinolin-2-amine
(75) 4-N-(8-chloroquinolin-2-yl)-1-N, 1-N-dimethylbenzene-1,4-diamine
(76) N-(4-methoxyphenyl)quinolin-2-amine
(77) 8-chloro-N-(4-methoxyphenyl)quinolin-2-amine
(78) 4-methyl-N-[4-(trifluoromethoxy)phenyl]quinolin-2-amine
(79) N-(4-methoxyphenyl)-3-methylquinolin-2-amine
(80) 3-methyl-N-[4-(trifluoromethoxy)phenyl]quinolin-2-amine
(81) 1-N, 1-N-dimethyl-4-N-(3-methylquinolin-2-yl)benzene-1,4-diamine
(82) N-[2-methyl-4-(trifluoromethoxy)phenyl]quinolin-2-amine
(83) N-[3-(trifluoromethoxy)phenyl]quinolin-2-amine
(84) N-[2-(trifluoromethoxy)phenyl]quinolin-2-amine
(85) N-(4-nitrophenyl)quinolin-2-amine
(86) N-(3-fluorophenyl)quinolin-2-amine
(87) 8-chloro-N-[3-(trifluoromethoxy)phenyl]quinolin-2-amine
(88) 8-chloro-N-(3-fluorophenyl)quinolin-2-amine
(89) 2-{[4-(trifluoromethoxy)phenyl]amino}quinolin-1-ium chloride
(90) 8-chloro-N-[4-(trifluoromethoxy)phenyl]quinolin-2-amine
(91) 3-methyl-N-[2-methyl-4-(trifluoromethoxy)phenyl]quinolin-2-amine
(92) 3-methyl-N-[3-(trifluoromethoxy)phenyl]quinolin-2-amine
(93) 3-methyl-N-[2-(trifluoromethoxy)phenyl]quinolin-2-amine
(94) 8-chloro-N-[2-methyl-4-(trifluoromethoxy)phenyl]quinolin-2-amine
(95) 3-methyl-2-{[4-(trifluoromethoxy)phenyl]amino}quinolin-1-ium chloride
(96) 6-chloro-N-(4-(trifluoromethoxy)phenyl)quinolin-2-amine
(97) 4-methyl-2-{[4-(trifluoromethoxy)phenyl]amino}quinolin-1-ium chloride
(98) 8-bromo-N-[4-(trifluoromethoxy)phenyl]quinolin-2-amine
(99) 8-fluoro-N-[4-(trifluoromethoxy)phenyl]quinolin-2-amine
(100) 8-methyl-N-[4-(trifluoromethoxy)phenyl]quinolin-2-amine
(101) N-(4-butoxyphenyl)-8-chloroquinolin-2-amine
(102) N-(4-phenoxyphenyl)quinolin-2-amine
(103) 8-methoxy-N-[4-(trifluoromethoxy)phenyl]quinolin-2-amine
(104) 8-chloro-N-[3-chloro-4-(trifluoromethoxy)phenyl]quinolin-2-amine
(105) N-(6-methylpyridin-2-yl)quinolin-3-amine
(106) N-(3-nitropyridin-2-yl)quinolin-3-amine
(107) N-(5-methylpyridin-2-yl)quinolin-6-amine
(108) N-(3-methoxypyridin-2-yl)quinolin-6-amine
(109) 6-chloro-N-(pyrazin-2-yl)quinolin-2-amine
(110) 8-bromo-N-(pyrazin-2-yl)quinolin-2-amine
(111) 8-methyl-N-(pyrazin-2-yl)quinolin-2-amine (112) 8-chloro-N-(pyrazin-2-yl)quinolin-2-amine
(113) N-(pyrazin-2-yl)quinolin-2-amine
(114) 4-methyl-N-(pyrazin-2-yl)quinolin-2-amine
(115) 3-methyl-N-(pyrazin-2-yl)quinolin-2-amine
(116) 8-fluoro-N-(pyrazin-2-yl)quinolin-2-amine
(117) 8-methoxy-N-(pyrazin-2-yl)quinolin-2-amine
(118) N-(pyridin-3-yl)quinolin-3-amine
(119) 8-chloro-N-(pyridin-4-yl)quinolin-2-amine
(120) N-(pyridin-4-yl)quinolin-2-amine
(121) N-(pyridin-4-yl)quinolin-3-amine
(122) N-[4-(trifluoromethoxy)phenyl]quinolin-3-amine
(123) N-(4-methoxyphenyl)quinolin-3-amine
(124) N-[4-(trifluoromethoxy)phenyl]quinoxalin-2-amine
(125) N-[2-methyl-4-(trifluoromethoxy)phenyl]quinoxalin-2-amine
(126) N-[3-(trifluoromethoxy)phenyl]quinoxalin-2-amine
(127) N-[2-(trifluoromethoxy)phenyl]quinoxalin-2-amine
(128) N-(pyrimidin-2-yl)quinolin-2-amine
(129) 8-chloro-N-(pyrimidin-2-yl)quinolin-2-amine
(130) 4-methyl-N-(pyrimidin-2-yl)quinolin-2-amine
(131) N-(pyrazin-2-yl)quinolin-6-amine
(132) N-(pyrazin-2-yl)quinolin-3-amine
(133) 6-methyl-N-(naphthalen-2-yl)pyridin-2-amine
(134) N-(naphthalen-2-yl)pyridin-2-amine
(135) N-(pyridin-2-yl)quinoxalin-2-amine
(136) N-(4-methylpyridin-2-yl)quinoxalin-2-amine
(137) 6-(quinoxalin-2-ylamino)pyridine-3-carbonitrile
(138) N-(6-methylpyridin-2-yl)quinoxalin-2-amine
(139) N-(4-methylpyridin-2-yl)-3-(trifluoromethyl)quinoxalin-2-amine
(140) N-(3,5-dichloro-4-methylpyridin-2-yl)quinoxalin-2-amine
(141) N-(4-methyl-3-nitropyridin-2-yl)quinoxalin-2-amine
(142) N-(pyrimidin-2-yl)quinoxalin-2-amine
(143) 4-N,4-N-dimethyl-7-N-[4-(trifluoromethoxy)phenyl]quinoline-4,7-diamine
(144) 4-(morpholin-4-yl)-N-[4-(trifluoromethoxy)phenyl]quinolin-7-amine
(145) 4-methoxy-N-(pyridin-2-yl)quinolin-7-amine
(146) 4-methoxy-N-(4-methylpyridin-2-yl)quinolin-7-amine
(147) 4-N,4-N-dimethyl-7-N-(4-methylpyridin-2-yl)quinoline-4,7-diamine
(148) 5,8-dimethyl-N-(5-methylpyridin-2-yl)isoquinolin-6-amine
(149) 5,8-dimethyl-N-(5-trifluoromethylpyridin-2-yl)isoquinolin-6-amine
(150) N-(4-methylpyridin-2-yl)-8-nitroquinolin-2-amine
(151) 6-chloro-N-(6-ethylpyridin-2-yl)quinolin-2-amine
(152) 6-chloro-N-(5-methylpyridin-2-yl)quinolin-2-amine
(153) 6-chloro-N-[5-(trifluoromethyl)pyridin-2-yl]quinolin-2-amine
(154) N2-(8-chloroquinolin-2-yl)-4-methylpyridine-2,3-diamine
(155) N-(4-butoxyphenyl)-3-methylquinolin-2-amine
(156) 4-N-(6-chloroquinolin-2-yl)-1-N, 1-N-dimethylbenzene-1,4-diamine
(157) 8-chloro-N-(3-chloro-4-methoxyphenyl)quinolin-2-amine
(158) N1-(8-chloroquinolin-2-yl)-4-(trifluoromethoxy)benzene-1,2-diamine
(159) N-(3-aminopyridin-2-yl)quinolin-3-amine
(160) 6-chloro-N-(4-methylpyridin-2-yl)quinoxalin-2-amine
(161) N-(4-ethylpyridin-2-yl)quinoxalin-2-amine
(162) N-(5-bromo-4-methylpyridin-2-yl)quinoxalin-2-amine
(163) N-(4,6-dimethylpyridin-2-yl)quinoxalin-2-amine
(164) [2-(quinoxalin-2-ylamino)pyridin-4-yl]methanol
(165) N-(4-methyl-5-nitropyridin-2-yl)quinoxalin-2-amine
(166) N-(4-methoxyphenyl)-4-(4-methylpiperazin-1-yl)quinolin-7-amine
(167) 4-methoxy-N-[4-(trifluoromethoxy)phenyl]quinolin-7-amine
(168) N-(4-methylpyridin-2-yl)-4-(morpholin-4-yl)quinolin-7-amine and a pharmaceutically acceptable salt thereof.

7. A method for treating a retroviral infection or a disease caused by the retroviral infection due to human leukemia viruses HTLV-1 comprising administering an effective amount of a pharmaceutical composition to a subject in need thereof, wherein the pharmaceutical composition comprises at least one compound of formula (I):

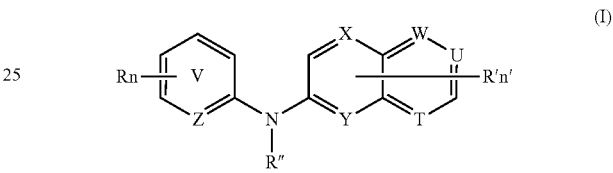

wherein:

is an aromatic ring wherein V is C or N and when V is N, V is in an ortho, meta or para position with respect to Z such that the ring respectively forms a pyridazine, a pyrimidine or a pyrazine, R independently represents a hydrogen atom, a halogen atom or a group chosen among a —CN group, a hydroxyl group, a —COOR$_1$ group, a (C$_1$-C$_3$)fluoroalkyl group, a (C$_1$-C$_3$)fluoroalkoxy group, a —NO$_2$ group, a —NR$_1$R$_2$ group, a (C$_1$-C$_4$)alkoxy group, a phenoxy group and a (C$_1$-C$_3$)alkyl group, said alkyl group being optionally mono-substituted by a hydroxyl group, R$_1$ and R$_2$ are independently a hydrogen atom or a (C$_1$-C$_3$)alkyl group, n is 1, 2 or 3, n' is 1 or 2, R' is a hydrogen atom, a halogen atom or a group chosen among a (C$_1$-C$_3$)alkyl group, a hydroxyl group, a —COOR$_1$ group, a —NO$_2$ group, a —NR$_1$R$_2$ group, a morpholinyl or a morpholino group, a N-methylpiperazinyl group, a (C$_1$-C$_3$)fluoroalkyl group, a (C$_1$-C$_4$) alkoxy group and a —CN group, R" is a hydrogen atom or a (C$_1$-C$_4$)alkyl group, Z is N or C, Y is N or C, X is N or C, W is N or C, T is N or C, U is N or C, and wherein at most four of the groups V, T, U, Z, Y, X and W are N,
and at least one of the groups T, U, Y, X and W is N,
or a pharmaceutically acceptable salt thereof.

8. The method of claim 7, wherein
Z is N, V is C, Y is N, X is C, T is C, U is C and W is C,
Z is C, V is C, Y is N, X is C, T is C, U is C and W is C,
Z is N, V is C, Y is C, X is N, T is C, U is C and W is C,
Z is N, V is C, Y is C, X is C, T is C, U is C and W is N,
Z is N, V is N and is in the para position with respect to Z, Y is N, X is C, T is C, U is C and W is C
Z is C, V is N and is in the para position with respect to Z, Y is C, X is N, T is C, U is C and W is C,
Z is C, V is N and is in the meta position with respect to Z and is in a para position with respect to the bond linked to NR", Y is N, X is C, T is C, U is C and W is C,
Z is C, V is N and is in the meta position with respect to Z and is in the para position with respect to the bond linked to NR", Y is C, X is N, T is C, U is C and W is C,
Z is C, V is C, Y is C, X is N, T is C, U is C and W is C,
Z is C, V is C, Y is N, X is N, T is C, U is C and W is C,
Z is N, V is N and is in the meta position with respect to Z and in an ortho position with respect to the bond linked to NR", Y is N, X is C, T is C, U is C and W is C,
Z is N, V is N and is in the para position with respect to Z, Y is C, X is C, T is C, U is C and W is N,
Z is N, V is N and is in the para position with respect to Z, Y is C, X is N, T is C, U is C and W is C,
Z is N, V is C, Y is N, X is N, T is C, U is C and W is C,
Z is N, V is N and is in the meta position with respect to Z and is in the ortho position with respect to the bond linked to NR", Y is N, X is N, T is C, U is C and W is C,
Z is C, V is C, Y is C, X is C, T is N, U is C and W is C,
Z is N, V is C, Y is C, X is C, T is N, U is C and W is C, or
Z is N, V is C, Y is C, X is C, T is C, U is N and W is C.

9. The method of claim 7, wherein
Z is N, V is C, Y is N, X is C, T is C, U is C and W is C,
Z is C, V is C, Y is N, X is C, T is C, U is C and W is C,
Z is N, V is C, Y is C, X is N, T is C, U is C and W is C,
Z is N, V is N and is in the para position with respect to Z, Y is N, X is C, T is C, U is C and W is C, or
Z is N, V is C, Y is N, X is N, T is C, U is C and W is C.

10. The method of claim 7, wherein the at least one compound of formula (I) is selected from the group consisting of:

(1)

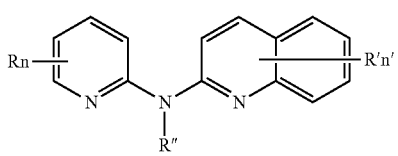
(Ia)

wherein:
R independently represents a hydrogen atom, a halogen atom or a group chosen among a $(C_1-C_3)$alkyl group, a —CN group, a hydroxyl group, a —COOR$_1$ group, a $(C_1-C_3)$fluoroalkyl group, a —NO$_2$ group, a —NR$_1$R$_2$ group and a $(C_1-C_3)$alkoxy group,
R' is a hydrogen atom, a halogen atom or a group chosen among a $(C_1-C_3)$alkyl group, a —NO$_2$ group, a $(C_1-C_3)$alkoxy group and a —NR$_1$R$_2$ group,
R$_1$ and R$_2$ are a hydrogen atom or a $(C_1-C_3)$alkyl group, (2)

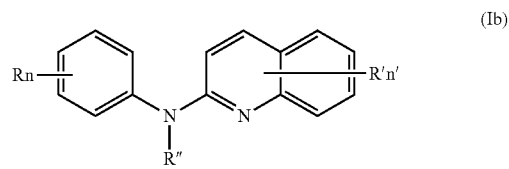
(Ib)

wherein:
R independently represents a hydrogen atom, a halogen atom or a group chosen among a $(C_1-C_3)$alkyl group, a —NR$_1$R$_2$ group, a $(C_1-C_3)$fluoroalkoxy group, a —NO$_2$ group, a phenoxy group and a $(C_1-C_4)$alkoxy group,
R$_1$ and R$_2$ are independently a hydrogen atom or a $(C_1-C_3)$alkyl group,
R' is a hydrogen atom, a halogen atom or a group chosen among a $(C_1-C_3)$alkyl group and a $(C_1-C_4)$alkoxy group, (3)

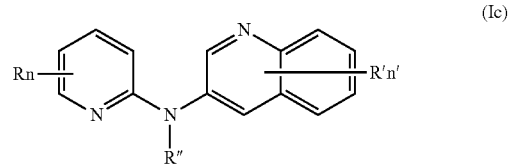
(Ic)

wherein:
R independently represents a hydrogen atom or a group chosen among a $(C_1-C_3)$alkyl group, a $(C_1-C_3)$fluoroalkyl group, a —NR$_1$R$_2$ group, a —COOR$_1$ group, a —NO$_2$ group and a $(C_1-C_3)$alkoxy group,
R' is a hydrogen atom,
R$_1$ and R$_2$ are independently a hydrogen atom or a $(C_1-C_3)$alkyl group, (4)

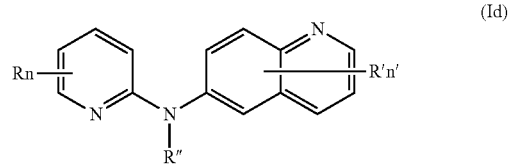
(Id)

wherein:
R independently represents a hydrogen atom or a group chosen among a $(C_1-C_3)$alkyl group, a $(C_1-C_3)$fluoroalkyl group and a $(C_1-C_3)$alkoxy group,
R' is a hydrogen atom, (5)

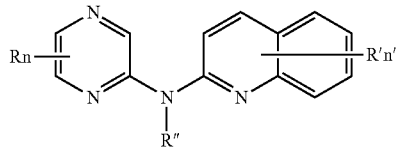
(Ie)

wherein:
R is a hydrogen atom,
R' is a hydrogen atom, a halogen atom or a group chosen among a $(C_1-C_3)$alkyl group and a $(C_1-C_3)$alkoxy group, (6)

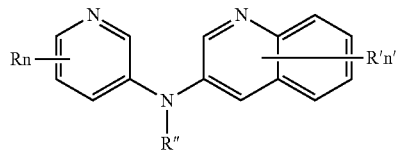
(If)

wherein:
R is a hydrogen atom,
R' is a hydrogen atom, (7)

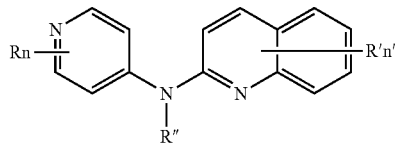
(Ig)

wherein:
R is a hydrogen atom,
R' is a hydrogen atom or a halogen atom, (8)

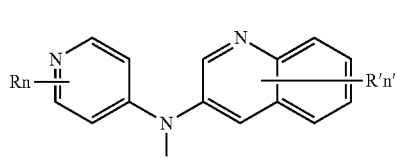
(Ih)

wherein:
R is a hydrogen atom,
R' is a hydrogen atom, (9)

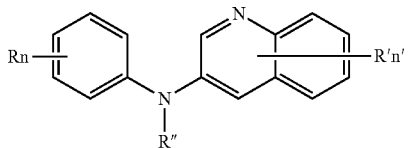
(Ii)

wherein:
R independently represents a hydrogen atom or a group chosen among a $(C_1-C_3)$fluoroalkoxy group and a $(C_1-C_3)$alkoxy group,
R' is a hydrogen atom, (10)

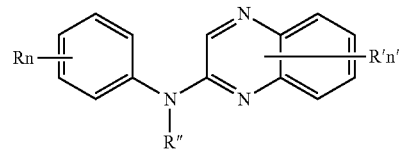
(Ij)

wherein:
R independently represents a hydrogen atom or a group chosen among a $(C_1-C_3)$fluoroalkoxy group and a $(C_1-C_3)$alkyl group,
R' is a hydrogen atom, (11)

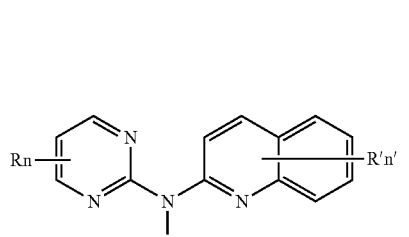
(Ik)

wherein:
R is a hydrogen atom,
R' is a hydrogen atom, a halogen atom or a $(C_1-C_3)$alkyl group, (12)

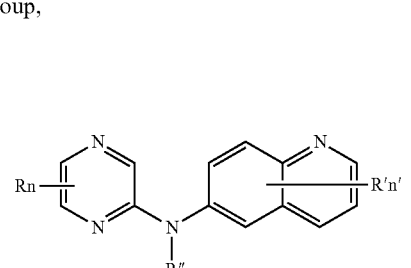
(Il)

wherein:
R is a hydrogen atom,
R' is a hydrogen atom, (13)

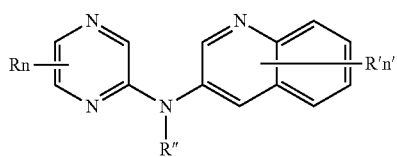
(Im)

wherein:
R is a hydrogen atom,
R' is a hydrogen atom, (14)

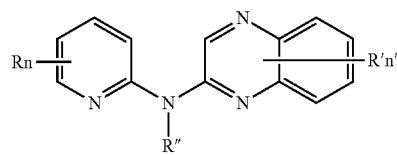
(Io)

wherein:
R independently represents a hydrogen atom, a halogen atom or a group chosen among, a —NO$_2$ group, a —CN group and a (C$_1$-C$_3$)alkyl group, said alkyl being optionally mono-substituted by a hydroxyl group,
R' is a hydrogen atom, a halogen atom or a (C$_1$-C$_3$) fluoroalkyl group, (15)

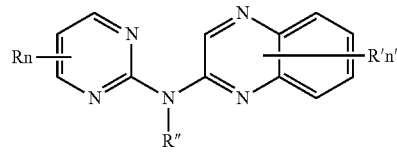
(Ip)

wherein:
R is a hydrogen atom,
R' is a hydrogen atom, (16)

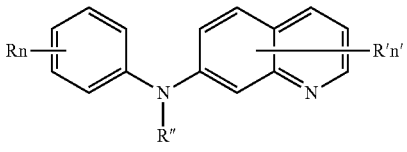
(Iq)

wherein:
R independently represents a hydrogen atom, a (C$_1$-C$_3$) alkoxy group or a (C$_1$-C$_3$)fluoroalkoxy group,
R' is a hydrogen atom or a group chosen among a —NR$_1$R$_2$ group, a N-methylpiperazinyl group, a (C$_1$-C$_3$)alkoxy group and a morpholino group,
R$_1$ and R$_2$ are independently a hydrogen atom or a (C$_1$-C$_3$)alkyl group, (17)

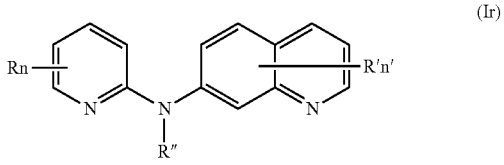
(Ir)

wherein:
R independently represents a hydrogen atom or a (C$_1$-C$_3$) alkyl group,
R' is a hydrogen atom or a group chosen among a —NR$_1$R$_2$ group, a morpholino group and a (C$_1$-C$_3$) alkoxy group,
R$_1$ and R$_2$ are independently a hydrogen atom or a (C$_1$-C$_3$)alkyl group, (18)

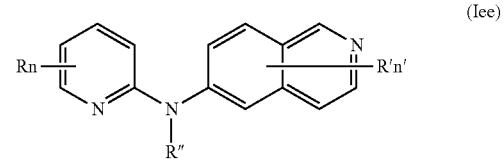
(Iee)

wherein:
R independently represents a hydrogen atom, a (C$_1$-C$_3$) alkyl group or a (C$_1$-C$_3$)fluoroalkyl group,
R' is a hydrogen atom or a (C$_1$-C$_3$)alkyl group,
and (19) a pharmaceutically acceptable salt thereof.

11. The method of claim 7, wherein the at least one compound of formula (I) is selected from the group consisting of:

(1)

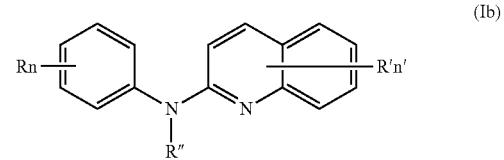
(Ia)

wherein:
R independently represents a hydrogen atom, a halogen atom or a group chosen among a (C$_1$-C$_3$)alkyl group, a (C$_1$-C$_3$)fluoroalkyl group, a hydroxyl group, a —CN group, a —COOH group and a (C$_1$-C$_3$)alkoxy group,
R' is a hydrogen atom, a halogen atom, a —NO$_2$ group or a (C$_1$-C$_3$)alkyl group, (2)

(Ib)

wherein:
R independently represents a hydrogen atom, a halogen atom, a group chosen among a $(C_1\text{-}C_3)$alkyl group, a —$NR_1R_2$ group, a $(C_1\text{-}C_3)$alkoxy group and a $(C_1\text{-}C_3)$ fluoroalkoxy group,
$R_1$ and $R_2$ are independently a hydrogen atom or a $(C_1\text{-}C_3)$alkyl group,
R' is a hydrogen atom, halogen atom or a $(C_1\text{-}C_3)$alkyl group, (3)

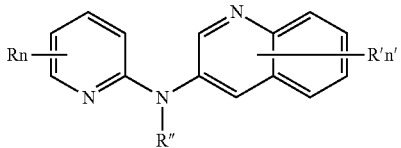

(Ic)

wherein:
R independently represents a hydrogen atom or a group chosen among a $(C_1\text{-}C_3)$fluoroalkyl group, a —$NO_2$ group and a $(C_1\text{-}C_3)$alkoxy group,
R' is a hydrogen atom, (4)

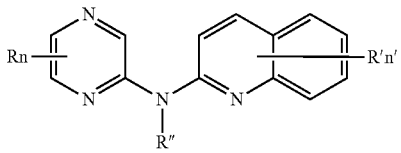

(Ie)

wherein:
R is a hydrogen atom,
R' is a hydrogen atom or a halogen atom, (5)

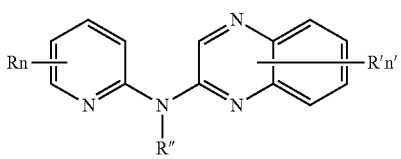

(Io)

wherein:
R independently represents a hydrogen atom, a halogen atom or a group chosen among a $(C_1\text{-}C_3)$alkyl group and a —$NO_2$ group,
n is 1, 2 or 3,
R' is a hydrogen atom or a $(C_1\text{-}C_3)$fluoroalkyl group,
and (6) a pharmaceutically acceptable salt thereof.

12. The method of claim 7, wherein the at least one compound is selected from the group consisting of
(1) (8-Chloro-quinolin-2-yl)-pyridin-2-yl-amine
(2) 2-(Quinolin-2-ylamino)-isonicotinic acid
(3) (4-Methyl-pyridin-2-yl)-quinolin-2-yl-amine
(4) Pyridin-2-yl-quinolin-2-yl-amine
(5) 2-(8-Chloro-quinolin-2-ylamino)-isonicotinic acid
(6) (8-Chloro-quinolin-2-yl)-(4-methyl-pyridin-2-yl)-amine
(7) 6-(Quinolin-2-ylamino)-nicotinonitrile
(8) Quinolin-2-yl-(4-trifluoromethoxy-phenyl)-amine
(9) Pyridin-2-yl-quinolin-3-yl-amine
(10) (3-Methoxy-pyridin-2-yl)-quinolin-3-yl-amine
(11) Quinolin-3-yl-(5-trifluoromethyl-pyridin-2-yl)-amine
(12) (5-Nitro-pyridin-2-yl)-quinolin-3-yl-amine
(13) (5-Methyl-pyridin-2-yl)-quinolin-3-yl-amine
(14) 2-(Quinolin-3-ylamino)-isonicotinic acid
(15) Quinolin-6-yl-(5-trifluoromethyl-pyridin-2-yl)-amine
(16) (6-Methyl-pyridin-2-yl)-quinolin-6-yl-amine
(17) N-(6-methylpyridin-2-yl)quinolin-2-amine
(18) 8-chloro-N-(6-methylpyridin-2-yl)quinolin-2-amine
(19) 4-methyl-N-(pyridin-2-yl)quinolin-2-amine
(20) 4-methyl-N-(4-methylpyridin-2-yl)quinolin-2-amine
(21) 3-methyl-N-(4-methylpyridin-2-yl)quinolin-2-amine
(22) 3-methyl-N-(pyridin-2-yl)quinolin-2-amine
(23) 6-((4-methylquinolin-2-yl)amino)nicotinonitrile
(24) 6-((3-methylquinolin-2-yl)amino)nicotinonitrile
(25) 6-chloro-N-(4-methylpyridin-2-yl)quinolin-2-amine
(26) 6-chloro-N-(6-methylpyridin-2-yl)quinolin-2-amine
(27) 4-methyl-N-(5-nitropyridin-2-yl)quinolin-2-amine
(28) N-(3-nitropyridin-2-yl)quinolin-2-amine
(29) 8-chloro-N-(3-nitropyridin-2-yl)quinolin-2-amine
(30) 2-((4-methylquinolin-2-yl)amino)nicotinonitrile
(31) N-(3-methylpyridin-2-yl)quinolin-2-amine
(32) N-(5-methylpyridin-2-yl)quinolin-2-amine
(33) 2-(quinolin-2-ylamino)isonicotinonitrile
(34) N-(5-(trifluoromethyl)pyridin-2-yl)quinolin-2-amine
(35) 8-chloro-N-(3-methylpyridin-2-yl)quinolin-2-amine
(36) 8-chloro-N-(5-methylpyridin-2-yl)quinolin-2-amine
(37) 8-chloro-N-(5-(trifluoromethyl)pyridin-2-yl)quinolin-2-amine
(38) N-(3-methoxypyridin-2-yl)quinolin-2-amine
(39) N-(5-nitropyridin-2-yl)quinolin-2-amine
(40) 6-((8-chloroquinolin-2-yl)amino)nicotinonitrile
(41) N-(5-fluoropyridin-2-yl)quinolin-2-amine
(42) N-(6-(trifluoromethyl)pyridin-2-yl)quinolin-2-amine
(43) 8-chloro-N-(5-fluoropyridin-2-yl)quinolin-2-amine
(44) 2-((8-chloroquinolin-2-yl)amino)nicotinic acid
(45) 4-methyl-N-(6-methylpyridin-2-yl)quinolin-2-amine
(46) 3-methyl-N-(6-methylpyridin-2-yl)quinolin-2-amine
(47) 5-cyano-2-(quinolin-2-ylamino)pyridin-1-ium chloride
(48) 2-((8-chloroquinolin-2-yl)amino)-4-methylpyridin-1-ium chloride
(49) 8-chloro-N-(4-ethylpyridin-2-yl)quinolin-2-amine
(50) 8-chloro-N-(6-ethylpyridin-2-yl)quinolin-2-amine
(51) 8-chloro-N-(4,6-dimethylpyridin-2-yl)quinolin-2-amine
(52) 6-((8-chloroquinolin-2-yl)amino)-2-methylnicotinonitrile
(53) 8-chloro-N-(4-chloropyridin-2-yl)quinolin-2-amine
(54) 8-methyl-N-(4-methylpyridin-2-yl)quinolin-2-amine
(55) N-(5-bromo-4-methylpyridin-2-yl)-8-chloroquinolin-2-amine
(56) 8-chloro-N-(3-ethyl-6-methylpyridin-2-yl)quinolin-2-amine
(57) 8-fluoro-N-(4-methylpyridin-2-yl)quinolin-2-amine
(58) 8-bromo-N-(4-methylpyridin-2-yl)quinolin-2-amine
(59) methyl 6-(quinolin-2-ylamino)nicotinate
(60) methyl 6-[(8-chloroquinolin-2-yl)amino]pyridine-3-carboxylate
(61) methyl 6-[(3-methylquinolin-2-yl)amino]pyridine-3-carboxylate

(62) methyl 2-[(8-chloroquinolin-2-yl)amino]pyridine-3-carboxylate
(63) 8-methoxy-N-(4-methylpyridin-2-yl)quinolin-2-amine
(64) N-(4-methylpyridin-2-yl)-5-nitroquinolin-2-amine
(65) 2-N-(4-methylpyridin-2-yl)quinoline-2,8-diamine
(66) (4-methylpyridin-2-yl)-5-aminoquinolin-2-amine
(67) methyl 6-[(4-methylquinolin-2-yl)amino]pyridine-3-carboxylate
(68) 8-chloro-N-[4-(trifluoromethyl)pyridin-2-yl]quinolin-2-amine
(69) 2-[(8-chloroquinolin-2-yl)amino]pyridin-3-ol
(70) 8-chloro-N-[6-(trifluoromethyl)pyridin-2-yl]quinolin-2-amine
(71) 6-chloro-N-(5-fluoropyridin-2-yl)quinolin-2-amine
(72) N-(6-ethylpyridin-2-yl)-3-methylquinolin-2-amine
(73) N-(5-fluoropyridin-2-yl)-3-methylquinolin-2-amine
(74) 3-methyl-N-[5-(trifluoromethyl)pyridin-2-yl]quinolin-2-amine
(75) 4-N-(8-chloroquinolin-2-yl)-1-N, 1-N-dimethylbenzene-1,4-diamine
(76) N-(4-methoxyphenyl)quinolin-2-amine
(77) 8-chloro-N-(4-methoxyphenyl)quinolin-2-amine
(78) 4-methyl-N-[4-(trifluoromethoxy)phenyl]quinolin-2-amine
(79) N-(4-methoxyphenyl)-3-methylquinolin-2-amine
(80) 3-methyl-N-[4-(trifluoromethoxy)phenyl]quinolin-2-amine
(81) 1-N, 1-N-dimethyl-4-N-(3-methylquinolin-2-yl)benzene-1,4-diamine
(82) N-[2-methyl-4-(trifluoromethoxy)phenyl]quinolin-2-amine
(83) N-[3-(trifluoromethoxy)phenyl]quinolin-2-amine
(84) N-[2-(trifluoromethoxy)phenyl]quinolin-2-amine
(85) N-(4-nitrophenyl)quinolin-2-amine
(86) N-(3-fluorophenyl)quinolin-2-amine
(87) 8-chloro-N-[3-(trifluoromethoxy)phenyl]quinolin-2-amine
(88) 8-chloro-N-(3-fluorophenyl)quinolin-2-amine
(89) 2-{[4-(trifluoromethoxy)phenyl]amino}quinolin-1-ium chloride
(90) 8-chloro-N-[4-(trifluoromethoxy)phenyl]quinolin-2-amine
(91) 3-methyl-N-[2-methyl-4-(trifluoromethoxy)phenyl]quinolin-2-amine
(92) 3-methyl-N-[3-(trifluoromethoxy)phenyl]quinolin-2-amine
(93) 3-methyl-N-[2-(trifluoromethoxy)phenyl]quinolin-2-amine
(94) 8-chloro-N-[2-methyl-4-(trifluoromethoxy)phenyl]quinolin-2-amine
(95) 3-methyl-2-{[4-(trifluoromethoxy)phenyl]amino}quinolin-1-ium chloride
(96) 6-chloro-N-(4-(trifluoromethoxy)phenyl)quinolin-2-amine
(97) 4-methyl-2-{[4-(trifluoromethoxy)phenyl]amino}quinolin-1-ium chloride
(98) 8-bromo-N-[4-(trifluoromethoxy)phenyl]quinolin-2-amine
(99) 8-fluoro-N-[4-(trifluoromethoxy)phenyl]quinolin-2-amine
(100) 8-methyl-N-[4-(trifluoromethoxy)phenyl]quinolin-2-amine
(101) N-(4-butoxyphenyl)-8-chloroquinolin-2-amine
(102) N-(4-phenoxyphenyl)quinolin-2-amine
(103) 8-methoxy-N-[4-(trifluoromethoxy)phenyl]quinolin-2-amine
(104) 8-chloro-N-[3-chloro-4-(trifluoromethoxy)phenyl]quinolin-2-amine
(105) N-(6-methylpyridin-2-yl)quinolin-3-amine
(106) N-(3-nitropyridin-2-yl)quinolin-3-amine
(107) N-(5-methylpyridin-2-yl)quinolin-6-amine
(108) N-(3-methoxypyridin-2-yl)quinolin-6-amine
(109) 6-chloro-N-(pyrazin-2-yl)quinolin-2-amine
(110) 8-bromo-N-(pyrazin-2-yl)quinolin-2-amine
(111) 8-methyl-N-(pyrazin-2-yl)quinolin-2-amine
(112) 8-chloro-N-(pyrazin-2-yl)quinolin-2-amine
(113) N-(pyrazin-2-yl)quinolin-2-amine
(114) 4-methyl-N-(pyrazin-2-yl)quinolin-2-amine
(115) 3-methyl-N-(pyrazin-2-yl)quinolin-2-amine
(116) 8-fluoro-N-(pyrazin-2-yl)quinolin-2-amine
(117) 8-methoxy-N-(pyrazin-2-yl)quinolin-2-amine
(118) N-(pyridin-3-yl)quinolin-3-amine
(119) 8-chloro-N-(pyridin-4-yl)quinolin-2-amine
(120) N-(pyridin-4-yl)quinolin-2-amine
(121) N-(pyridin-4-yl)quinolin-3-amine
(122) N-[4-(trifluoromethoxy)phenyl]quinolin-3-amine
(123) N-(4-methoxyphenyl)quinolin-3-amine
(124) N-[4-(trifluoromethoxy)phenyl]quinoxalin-2-amine
(125) N-[2-methyl-4-(trifluoromethoxy)phenyl]quinoxalin-2-amine
(126) N-[3-(trifluoromethoxy)phenyl]quinoxalin-2-amine
(127) N-[2-(trifluoromethoxy)phenyl]quinoxalin-2-amine
(128) N-(pyrimidin-2-yl)quinolin-2-amine
(129) 8-chloro-N-(pyrimidin-2-yl)quinolin-2-amine
(130) 4-methyl-N-(pyrimidin-2-yl)quinolin-2-amine
(131) N-(pyrazin-2-yl)quinolin-6-amine
(132) N-(pyrazin-2-yl)quinolin-3-amine
(133) 6-methyl-N-(naphthalen-2-yl)pyridin-2-amine
(134) N-(naphthalen-2-yl)pyridin-2-amine
(135) N-(pyridin-2-yl)quinoxalin-2-amine
(136) N-(4-methylpyridin-2-yl)quinoxalin-2-amine
(137) 6-(quinoxalin-2-ylamino)pyridine-3-carbonitrile
(138) N-(6-methylpyridin-2-yl)quinoxalin-2-amine
(139) N-(4-methylpyridin-2-yl)-3-(trifluoromethyl)quinoxalin-2-amine
(140) N-(3,5-dichloro-4-methylpyridin-2-yl)quinoxalin-2-amine
(141) N-(4-methyl-3-nitropyridin-2-yl)quinoxalin-2-amine
(142) N-(pyrimidin-2-yl)quinoxalin-2-amine
(143) 4-N,4-N-dimethyl-7-N-[4-(trifluoromethoxy)phenyl]quinoline-4,7-diamine
(144) 4-(morpholin-4-yl)-N-[4-(trifluoromethoxy)phenyl]quinolin-7-amine
(145) 4-methoxy-N-(pyridin-2-yl)quinolin-7-amine
(146) 4-methoxy-N-(4-methylpyridin-2-yl)quinolin-7-amine
(147) 4-N,4-N-dimethyl-7-N-(4-methylpyridin-2-yl)quinoline-4,7-diamine
(148) 5,8-dimethyl-N-(5-methylpyridin-2-yl)isoquinolin-6-amine
(149) 5,8-dimethyl-N-(5-trifluoromethylpyridin-2-yl)isoquinolin-6-amine
(150) N-(4-methylpyridin-2-yl)-8-nitroquinolin-2-amine
(151) 6-chloro-N-(6-ethylpyridin-2-yl)quinolin-2-amine
(152) 6-chloro-N-(5-methylpyridin-2-yl)quinolin-2-amine
(153) 6-chloro-N-[5-(trifluoromethyl)pyridin-2-yl]quinolin-2-amine
(154) N2-(8-chloroquinolin-2-yl)-4-methylpyridine-2,3-diamine
(155) N-(4-butoxyphenyl)-3-methylquinolin-2-amine (156) 4-N-(6-chloroquinolin-2-yl)-1-N, 1-N-dimethyl-benzene-1,4-diamine
(157) 8-chloro-N-(3-chloro-4-methoxyphenyl)quinolin-2-amine
(158) N1-(8-chloroquinolin-2-yl)-4-(trifluoromethoxy) benzene-1,2-diamine
(159) N-(3-aminopyridin-2-yl)quinolin-3-amine
(160) 6-chloro-N-(4-methylpyridin-2-yl)quinoxalin-2-amine
(161) N-(4-ethylpyridin-2-yl)quinoxalin-2-amine
(162) N-(5-bromo-4-methylpyridin-2-yl)quinoxalin-2-amine
(163) N-(4,6-dimethylpyridin-2-yl)quinoxalin-2-amine
(164) [2-(quinoxalin-2-ylamino)pyridin-4-yl]methanol
(165) N-(4-methyl-5-nitropyridin-2-yl)quinoxalin-2-amine
(166) N-(4-methoxyphenyl)-4-(4-methylpiperazin-1-yl)quinolin-7-amine
(167) 4-methoxy-N-[4-(trifluoromethoxy)phenyl]quinolin-7-amine
(168) N-(4-methylpyridin-2-yl)-4-(morpholin-4-yl)quinolin-7-amine
and a pharmaceutically acceptable salt thereof.

* * * * *